United States Patent
Taniguchi et al.

(10) Patent No.: US 9,513,234 B2
(45) Date of Patent: Dec. 6, 2016

(54) DEVICE AND METHOD FOR CAPTURING X-RAY IMAGE OF BONE-IN MEAT AND DEBONING SYSTEM OF BONE-IN MEAT INCLUDING THE DEVICE

(71) Applicant: MAYEKAWA MFG. CO., LTD., Tokyo (JP)

(72) Inventors: Akira Taniguchi, Tokyo (JP); Hiroyuki Sakurayama, Tokyo (JP); Osamu Goto, Tokyo (JP); Masaru Tokumoto, Tokyo (JP); Hiroaki Muranami, Tokyo (JP)

(73) Assignee: MAYEKAWA MFG. CO., LTD., Tokyo (JP)

(*) Notice: Subject to any disclaimer, the term of this patent is extended or adjusted under 35 U.S.C. 154(b) by 182 days.

(21) Appl. No.: 14/484,661

(22) Filed: Sep. 12, 2014

(65) Prior Publication Data

US 2014/0376693 A1  Dec. 25, 2014

Related U.S. Application Data

(63) Continuation of application No. PCT/JP2013/055299, filed on Feb. 28, 2013.

(30) Foreign Application Priority Data

Mar. 13, 2012 (JP) ................. 2012-056286

(51) Int. Cl.
- *G01N 23/04* (2006.01)
- *A22B 5/00* (2006.01)

(Continued)

(52) U.S. Cl.
CPC ............. *G01N 23/04* (2013.01); *A22B 5/007* (2013.01); *A22B 5/0035* (2013.01);

(Continued)

(58) Field of Classification Search
CPC ...... G01N 23/04; G01N 33/12; A22C 17/004; A22C 17/0093; A22C 17/0086; G21K 1/00; A22B 5/0035; A22B 5/007
See application file for complete search history.

(56) References Cited

U.S. PATENT DOCUMENTS

| 5,133,687 A | 7/1992 | Malloy |
| 5,462,477 A | 10/1995 | Ketels |

(Continued)

FOREIGN PATENT DOCUMENTS

| EP | 1591015 A1 | 11/2005 |
| EP | 2153727 A1 | 2/2010 |

(Continued)

OTHER PUBLICATIONS

Notice of Allowance mailed on Jan. 8, 2015 issued in related U.S. Appl. No. 14/484,759.

(Continued)

*Primary Examiner* — Courtney Thomas
(74) *Attorney, Agent, or Firm* — Rossi, Kimms & McDowell LLP

(57) ABSTRACT

An X-ray image capturing device of bone-in meat for capturing an X-ray image of the bone-in meat that is from an arm part or a thigh part of a livestock carcass in a state where the bone-in meat is suspended, comprises: an X-ray source for irradiating the bone-in meat with an X-ray; a shielding box for covering the bone-in meat while the X-ray image is captured; a sensor which is disposed in the shielding box and which detects the X-ray which passes through the bone-in meat; and a filter which is disposed between the bone-in meat and the X-ray source and which adjusts an intensity distribution of the X-ray with which the bone-in meat is irradiated.

5 Claims, 71 Drawing Sheets

(51) Int. Cl.
*A22C 17/00* (2006.01)
*G21K 1/00* (2006.01)
*G01N 33/12* (2006.01)

(52) U.S. Cl.
CPC ........ *A22C 17/004* (2013.01); *A22C 17/0086* (2013.01); *A22C 17/0093* (2013.01); *G01N 33/12* (2013.01); *G21K 1/00* (2013.01)

(56) References Cited

U.S. PATENT DOCUMENTS

| | | | |
|---|---|---|---|
| 6,059,648 | A | 5/2000 | Kodama et al. |
| 6,299,524 | B1 | 10/2001 | Janssen et al. |
| 6,354,933 | B1 | 3/2002 | Archambault et al. |
| 6,418,193 | B1 * | 7/2002 | Albagli ................ A61B 6/4035 348/E5.086 |
| 7,198,564 | B2 | 4/2007 | Hino et al. |
| 7,351,134 | B2 | 4/2008 | Mammoto et al. |
| 8,070,567 | B2 | 12/2011 | Umino et al. |
| 8,292,702 | B2 | 10/2012 | Bolte et al. |
| 8,376,814 | B2 | 2/2013 | Hattori et al. |
| 2002/0067797 | A1 | 6/2002 | Safai et al. |
| 2003/0065414 | A1 | 4/2003 | Van Den Nieuwelaar et al. |
| 2007/0207242 | A1 | 9/2007 | Carlsen |
| 2008/0020693 | A1 | 1/2008 | Toyoshima et al. |
| 2009/0270021 | A1 | 10/2009 | Umino et al. |
| 2010/0256952 | A1 * | 10/2010 | Dekker ................ G01G 9/005 702/180 |
| 2012/0295527 | A1 | 11/2012 | Hattori et al. |

FOREIGN PATENT DOCUMENTS

| | | |
|---|---|---|
| EP | 2277382 A1 | 1/2011 |
| EP | 2277384 A1 | 1/2011 |
| JP | 5547467 A | 4/1980 |
| JP | 63108251 A | 5/1988 |
| JP | 06324006 A | 11/1994 |
| JP | 2000189045 A | 7/2000 |
| JP | 2002534069 A | 10/2002 |
| JP | 3728518 B2 | 12/2005 |
| JP | 2008099574 A | 5/2008 |
| WO | 2009139031 A1 | 11/2009 |
| WO | 2009139032 A1 | 11/2009 |
| WO | 2012056793 A1 | 5/2012 |

OTHER PUBLICATIONS

Notice of Allowance issued in U.S. Appl. No. 14/484,947, dated Jan. 20, 2015.
International Search Report issued in PCT/JP2013/055299, dated May 7, 2013. English translation provided.
International Search Report issued in PCT/JP2013/055301, dated Jun. 11, 2013. English translation provided.
International Search Report issued in PCT/JP2013/055298, dated Jun. 11, 2013. English translation provided.
International Search Report issued in PCT/JP2013/055300, dated Jun. 11, 2013. English translation provided.
Written Opinion issued in PCT/JP2013/055298 mailed Jun. 11, 2013. English translation provided.
International Preliminary Report on Patentability issued in PCT/JP2013/055298 mailed Sep. 25, 2014. English translation provided.
Written Opinion issued in PCT/JP2013/055299 mailed May 7, 2013. English translation provided.
International Preliminary Report on Patentability issued in PCT/JP2013/055299 mailed Sep. 25, 2014. English translation provided.
Written Opinion issued in PCT/JP2013/055300 mailed Jun. 11, 2013. English translation provided.
International Preliminary Report on Patentability issued in PCT/JP2013/055300 mailed Sep. 25, 2014. English translation provided.
Written Opinion issued in PCT/JP2013/055301 mailed Jun. 11, 2013. English translation provided.
International Preliminary Report on Patentability issued in PCT/JP2013/055301 mailed Sep. 25, 2014. English translation provided.
European Search Report issued in European counterpart application No. EP13761113.3, dated Oct. 22, 2015.
European Search Report issued in European counterpart application No. EP13760623.2, dated Oct. 13, 2015.
Extended European Search Report issued in EP13760554.9, mailed Nov. 11, 2015.
Extended European Search Report issued in EP137616322, mailed Nov. 11, 2015.

* cited by examiner

Fig.17
(a) 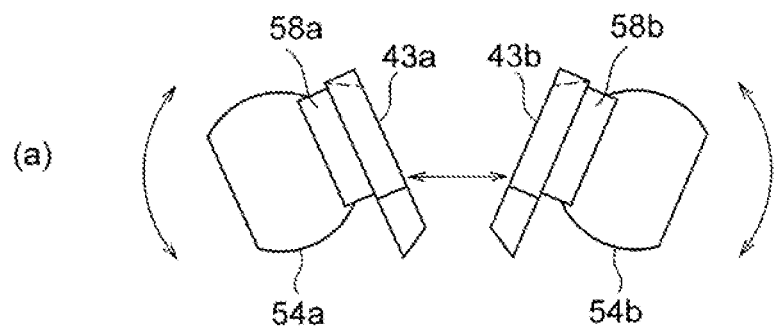
(b) 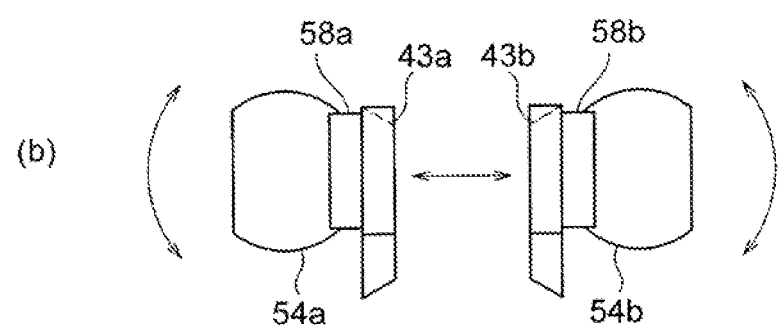

Fig.43
(a) 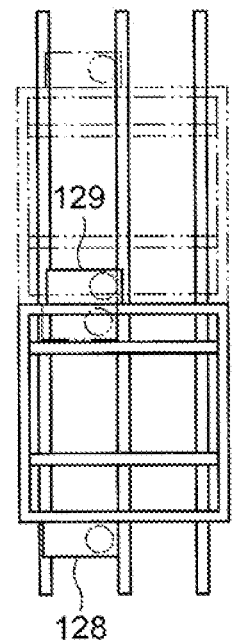
(b) 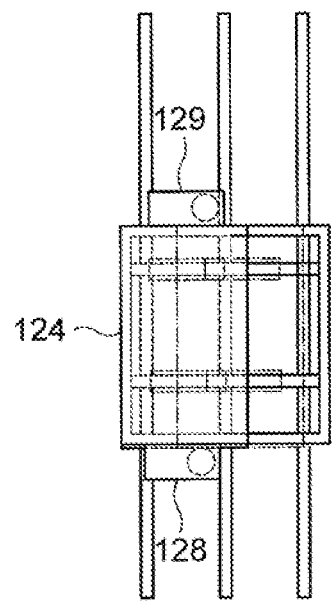

Fig.55
(a)
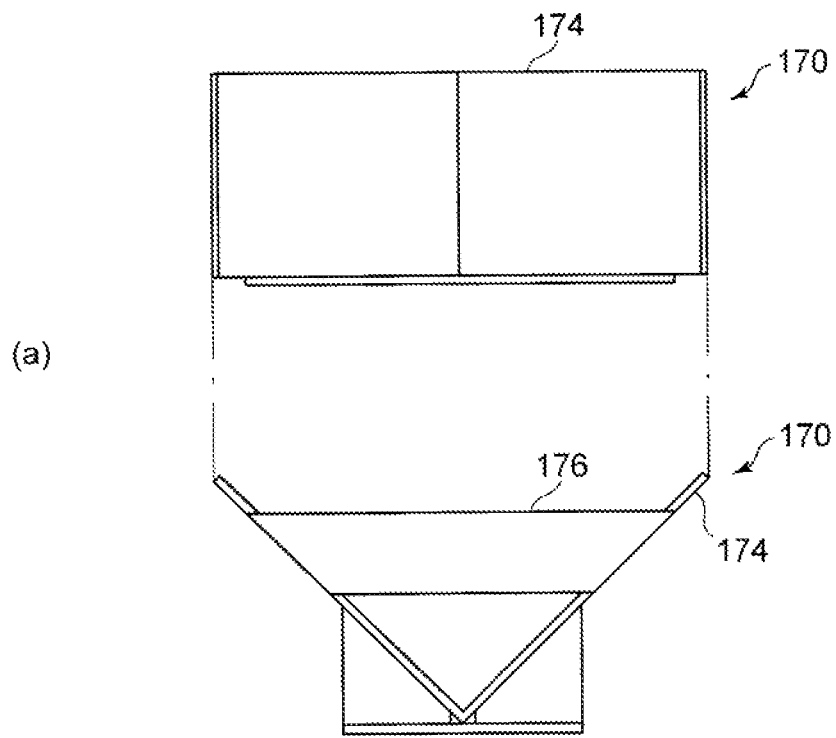
(b)
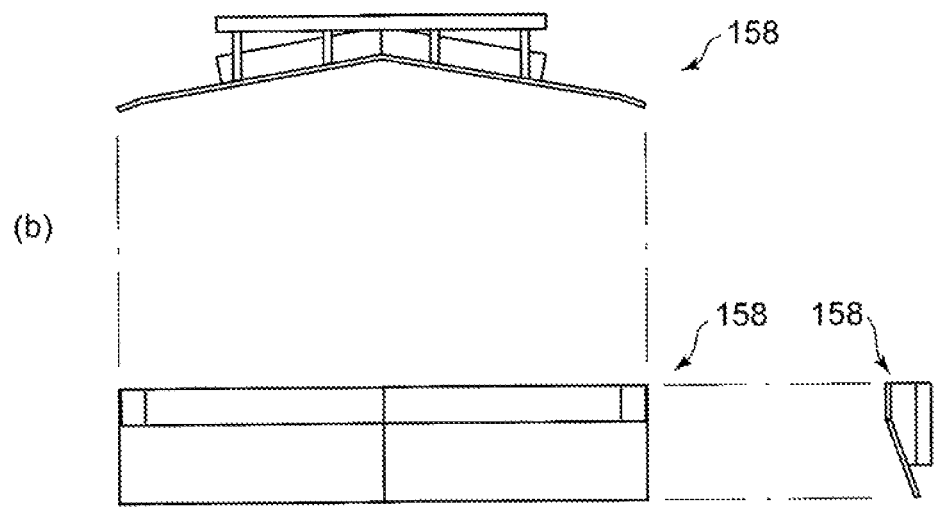

DEVICE AND METHOD FOR CAPTURING X-RAY IMAGE OF BONE-IN MEAT AND DEBONING SYSTEM OF BONE-IN MEAT INCLUDING THE DEVICE

CROSS-REFERENCE TO RELATED APPLICATIONS

This application is a continuation of International Application No. PCT/JP2013/055299, filed on Feb. 28, 2013, and is based on and claims priority to Japanese Patent Application No. JP 2012-056286, filed on Mar. 13, 2012. The disclosure of the Japanese priority application and the PCT application in their entirety, including the drawings, claims, and the specification thereof, are incorporated herein by reference.

BACKGROUND

1. Field of the Invention

The present invention relates to a device and a method for capturing x-ray image of bone-in meat from an arm part or a thigh part of a livestock carcass, and a deboning system of bone-in meat including the device.

2. Discussion of the Background

A carcass of livestock such as a pig, a cow, or a sheep is served as meat. A deboning method of bone-in meat (hereinafter referred to as a "work") from an arm part or a thigh part of the livestock carcass roughly has a pre-processing step, an incision making step, and a meat separation step. In the pre-processing step, a hip bone and the like are removed. In the incision making step, an incision is made along a forearm bone and an upper arm bone of the work in the case where the work is the arm part, and an incision is made along a lower thigh bone and a thigh bone of the work in the case where the work is the thigh part. In the meat separation step, meat is torn from bones of the work.

The present inventors propose a deboning system in which the incision making step and the meat separation step are automatically performed.

For example, in the deboning system disclosed in Japanese Patent Application Laid-open No. 2008-99574 (Patent Document 1), the work in which incision making of the forearm bone is manually performed in the pre-processing step is supplied. The supplied work is suspended from a clamp manually, and is sent to a robot arm which performs the incision making step.

A cutter tool is attached to the robot arm, and the cutter tool executes the incision making with a predetermined course using the robot arm. The length of the work is measured by using a photoelectric sensor in advance and the course of the incision making is determined on the basis of the measurement result. During the incision making step, the work is held by a work holding mechanism while being suspended by the clamp.

In addition, in the meat separation step of the deboning system, the work is lifted while being rotated in a state where a cutter is in contact with the work, and the forearm bone and the upper arm bone are thereby removed the work. The lift amount of the work is also determined on the basis of the measurement result of the length of the work.

Thereafter, a shoulder blade is removed from the work. Specifically, after the work from which the forearm bone and the arm bone have been removed is transferred to a belt conveyor, the work is rested at a predetermined position by a V-shaped guide. Subsequently, incision making is performed along the shoulder blade of the work. After the incision making, the work is conveyed again by the belt conveyor. When the work reached a predetermined conveyance position, the belt conveyor is stopped, and the shoulder blade of the work is chucked and removed by a chuck cutter and a U-shaped cutter.

Japanese Patent Application Laid-open No. 1994-324006 (Patent Document 2) discloses the processing equipment of meat tissue. This processing equipment acquires a position information related to a sinew, a tendon, a born, or the like of bone-in meat by using an X-ray irradiation device, and cuts the sinew, the tendon, the born, or the like based on the acquired position information. Specifically, the bone-in meat on the mounting table is irradiated with the X-ray in a vertical direction.

SUMMARY

The processing equipment described in Patent Document 2 irradiates the bone-in meat on the mounting table with the X-ray in the vertical direction. In a case where the X-ray image picked up with the stereotypical arrangement is used, it is difficult to acquire accurate information related to a position of the bone or a shape of the bone in the bone-in meat. If an incision making is performed based on inaccurate information, a yield rate decreases because the trajectory of the cutter deviates from the bone and the meat remains on the bone, or an excessive load is applied to the cutter because the cutter cuts into the bone.

Specifically, in a case where the incision making is performed in a state where a work moves at high speed, the decrease of the yield rate or the excessive load of the cutter becomes remarkable. Thus, it is necessary to slow down a moving speed of the work, and, as a result, ability of processing decreases.

Embodiments of the present invention provide a device and a method for capturing a clear x-ray image of bone-in meat from an arm part or a thigh part of a livestock carcass, and a deboning system of bone-in meat including the device.

According to an aspect of the present invention, there is provided an X-ray image capturing device of bone-in meat for capturing an X-ray image of the bone-in meat including an arm part or a thigh part of a livestock carcass in a state where the bone-in meat is suspended, including: an X-ray source for irradiating the bone-in meat with an X-ray; a shielding box for covering the bone-in meat while the X-ray image is picked up; a sensor which is disposed in the shielding box and which detects the X-ray which passes through the bone-in meat; and a filter which is disposed between the bone-in meat and the X-ray source and which adjusts an intensity distribution of the X-ray with which the bone-in meat is irradiated.

According to the X-ray image capturing device of the bone-in meat, the filter adjusts the intensity distribution of the X-ray with which the bone-in meat is irradiated, and hence the clear X-ray image can be picked up. Consequently, when the incision making is performed on the bone-in meat based on the X-ray image, the trajectory of the incision making is accurately conforms to the shape of the bone. Thus, yields can be improved and application of an excessive load to the cutter is prevented.

Preferably, the bone-in meat is suspended from a clamp going around an endless track, and the X-ray image capturing device further includes a rotation mechanism for rotating the clamp so that the bone-in meat rotates about a vertical axis in a rotation direction corresponding to a right or a left of the bone-in meat in order to capture the X-ray image.

According to the above configuration, the bone-in meat rotates about the vertical axis in the rotation direction corresponding to the right or the left of the bone-in meat, and hence the X-ray image which is suitable for decision about the trajectory of the incision making can be picked up. Consequently, in performing the incision making based on the X-ray image, yields can be further improved and application of an excessive load to the cutter is prevented more effectively.

Preferably, the rotation mechanism rotates the clamp such that an incident angle of the X-ray relative to a cut surface of the bone-in meat separated from the body is more than 30° and less than 45°.

According to the above configuration, it is possible to reliably capture an X-ray image suitable for decision of the trajectory of the incision making by rotating the clamp such that an incident angle of the X-ray relative to a cut surface of the bone-in meat separated from the trunk is more than 30° and less than 45°.

Preferably, the X-ray image capturing device of bone-in meat further includes a shielding-box movement mechanism which moves the shielding box in a direction along the endless track and a direction orthogonal to the endless track in synchronization with the clamp.

According to the above configuration, the X-ray image can be picked up while the clamp moves. Consequently, when the X-ray image capturing device of bone-in meat is applied to a deboning system, the X-ray image can be picked up without decreasing an ability of processing of the deboning system.

According to an aspect of the present invention, there is provided a deboning system including an incision making device which performs incision making on the bone-in meat based on the X-ray image picked up by any one of the above-described X-ray image capturing devices.

According to the above configuration, since the incision making is performed based on the clear X-ray image, the meat which remains on the bone can be reduced and the yield rate can be increased. Further, the cutting of the cutter into the bone can be prevented, and the excessive load on the cutter can be prevented.

According to an aspect of the present invention, there is provided an X-ray image capturing method for capturing an X-ray image of the bone-in meat including an arm part or a thigh part of a livestock carcass in a state where the bone-in meat is suspended, including the steps of: irradiating the bone-in meat with an X-ray from an X-ray source; covering the bone-in meat with a shielding box in which a sensor for detecting the X-ray passing through the bone-in meat is disposed; and disposing a filter between the bone-in meat and the X-ray source, the filter being configured to adjust an intensity distribution of the X-ray with which the bone-in meat is irradiated.

According to the X-ray image capturing method of the bone-in meat, the filter adjusts the intensity distribution of the X-ray with which the bone-in meat is irradiated, and hence the clear X-ray image can be picked up. Consequently, when the incision making is performed on the bone-in meat based on the X-ray image, the trajectory of the incision making is accurately conforms to the shape of the bone. Thus, yields can be improved and application of an excessive load to the cutter is prevented.

According to the present invention, there are provided a device and a method for capturing a clear x-ray image of bone-in meat from an arm part or a thigh part of a livestock carcass, and a deboning system of bone-in meat including the device.

BRIEF DESCRIPTION OF DRAWINGS

FIG. 17(a) shows the disposition of the hooking member when the hooking member is stuck into the work, and FIG. 17(b) shows the disposition of the hooking member when the work is detached;

FIGS. 43(a) and 43(b) are views for explaining the configuration of a drive mechanism of a shielding box;

FIGS. 49(a) and 49(b) are front views schematically showing a support device of the first incision making station, in which FIG. 49(a) shows an operation state and FIG. 49(b) shows a wait state;

FIG. 55(a) includes a top view and a front view of the bottom holder, and FIG. 55(b) includes a top view, a front view, and a side view of the upper side support member;

DETAILED DESCRIPTION

Figure 1:
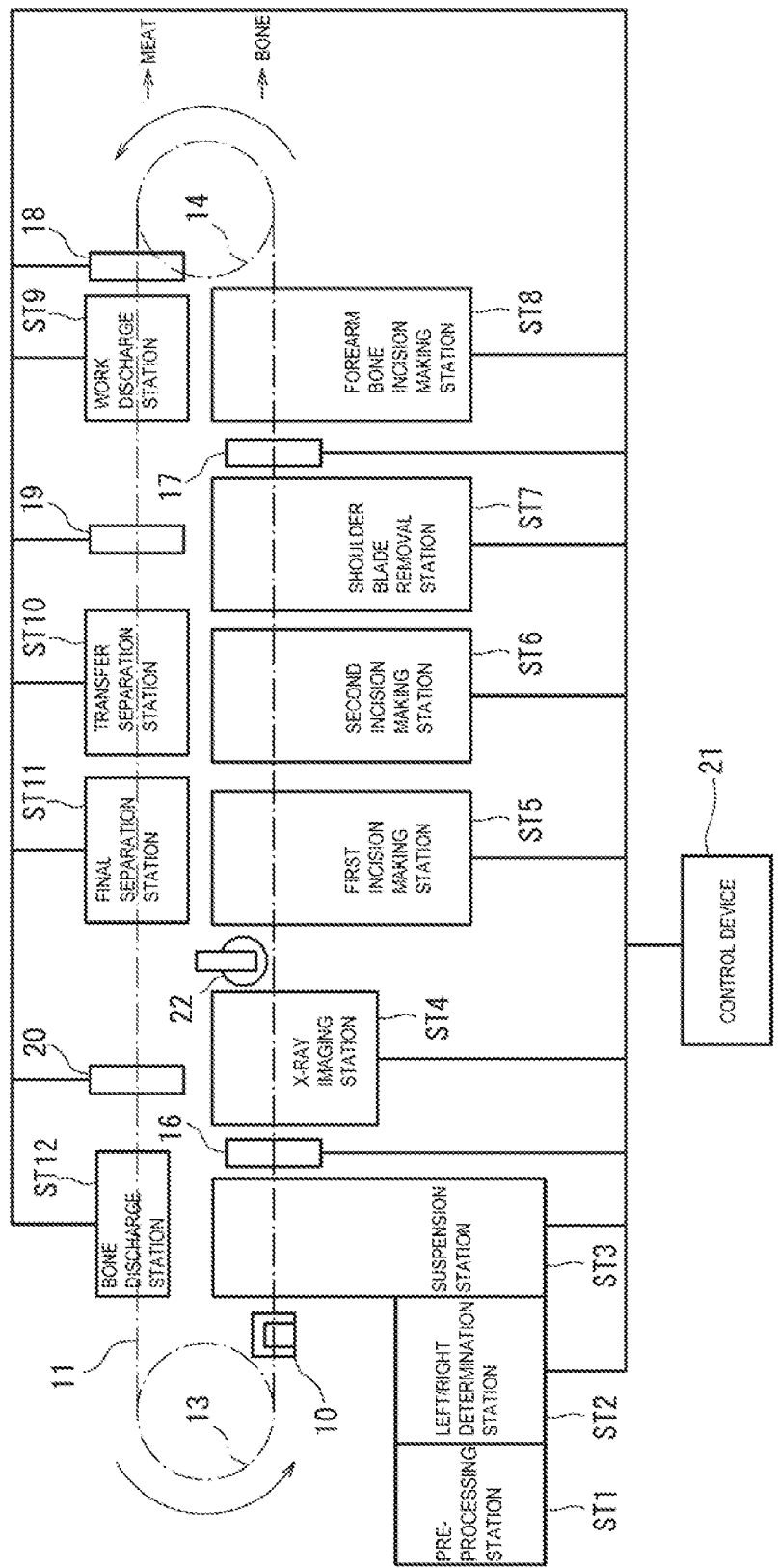
FIG. 1 is a view schematically showing the entire configuration of a deboning system of bone-in meat of an embodiment of the present invention.

The present invention will be described in detail by using embodiments shown in the drawings. However, it is to be noted that the scope of the present invention is not limited only to dimensions, materials, shapes, and relative arrangements of components described in the embodiments unless specifically described.

[Entire Configuration of Deboning System]

FIG. 1 shows the schematic configuration of a deboning system of bone-in meat (hereinafter also referred to as a deboning system) of an embodiment of the present invention.

The deboning system has a pre-processing station ST1, a left/right determination station ST2, a suspension station ST3, an X-ray imaging station ST4, a first incision making station ST5, a second incision making station ST6, a shoulder blade removal station ST7, a forearm-bone incision making station ST8, a work discharge station ST9, a transfer separation station ST10, a final separation station ST11, and a bone discharge station ST12.

In addition, the deboning system has a plurality of clamps 10 which convey a work W in a state in which the work W is suspended from the clamp 10, and each clamp 10 goes around an endless track 11. Specifically, the clamps 10 are coupled to a chain, and the chain is rotated using sprockets 13 and 14 along the endless track 11. Note that, although not shown in the drawing, a plurality of belt conveyors are disposed along the endless track 11, and meat and bones separated from each other are separately conveyed to the outside of the deboning system.

The suspension station ST3, the X-ray imaging station ST4, the first incision making station ST5, the second incision making station ST6, the shoulder blade removal station ST7, the forearm-bone incision making station ST8, the work discharge station ST9, the transfer separation station ST10, the final separation station ST11, and the bone discharge station ST12 are provided in this order along the endless track 11.

In addition, in order to rotate the clamp 10 by a predetermined angle, a first clamp rotation device 16, a second clamp rotation device 17, a third clamp rotation device 18, a fourth clamp rotation device 19, and a fifth clamp rotation device 20 are provided in this order along the endless track 11.

The first clamp rotation device 16 is positioned between the suspension station ST3 and the X-ray imaging station ST4, and the second clamp rotation device 17 is positioned between the shoulder blade removal station ST7 and the forearm-bone incision making station ST8.

The third clamp rotation device 18 is positioned between the forearm-bone incision making station ST8 and the work discharge station ST9, and the fourth clamp rotation device 19 is positioned between the work discharge station ST9 and the transfer separation station ST10. The fifth clamp rotation device 20 is positioned between the final separation station ST11 and the bone discharge station ST12.

Further, the deboning system has a control device 21 which controls the entire operation. The control device 21 is configured by, e.g., a computer including a central processing unit, a memory, an external storage device, an input device, and an output device. Preferably, the control device 21 is connected to all of the stations ST2 to ST12 except the pre-processing station ST, and the first to fifth clamp rotation devices 16, 17, 18, 19, and 20.

Furthermore, the deboning system has a round blade cutter device 22 which is positioned between the X-ray imaging station ST4 and the first incision making station S5, and is provided along the endless track.

[Deboning Method]

Figure 2:
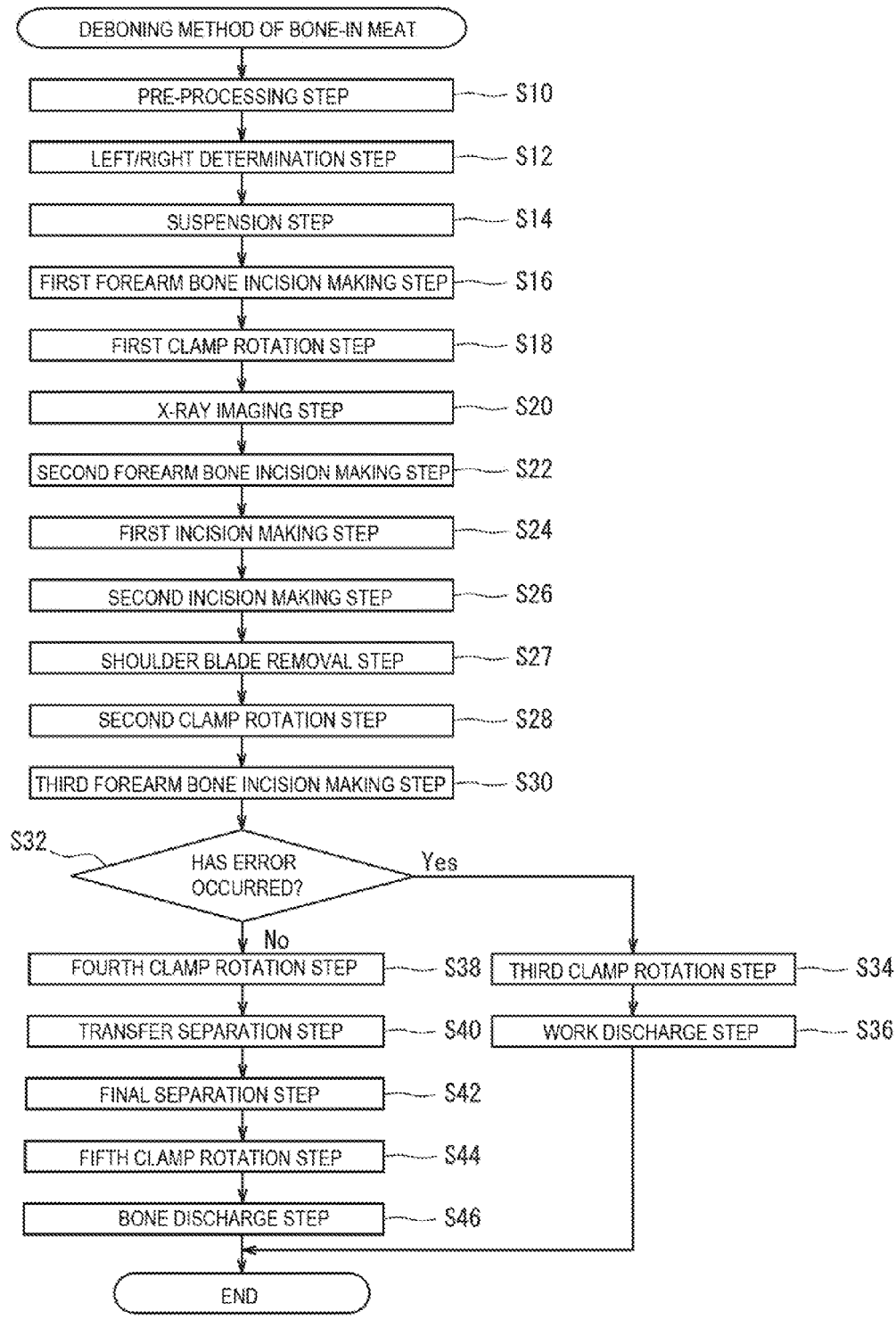
FIG. 2 is a flowchart showing processing procedures of a deboning method executed by the deboning system of FIG. 1.

FIG. 2 is a flowchart schematically showing processing procedures of a deboning method of bone-in meat executed by the deboning system.

The deboning method includes a pre-processing step S10, a left/right determination step S12, a suspension step S14, a first forearm-bone incision making step S16, a first clamp rotation step S18, an X-ray imaging step S20, a second forearm-bone incision making step S22, a first incision making step S24, a second incision making step S26, a shoulder blade removal step S27, a second clamp rotation step S28, a third forearm-bone incision making step S30, an error occurrence determination step S32, a third clamp rotation step S34, a work discharge step S36, a fourth clamp rotation step S38, a transfer separation step S40, a final separation step S42, a fifth clamp rotation step S44, and a bone discharge step S46.

Hereinbelow, the individual steps will be described together with the configurations of devices used in the steps.

[Pre-Processing Step/Pre-Processing Station]

Figure 3:
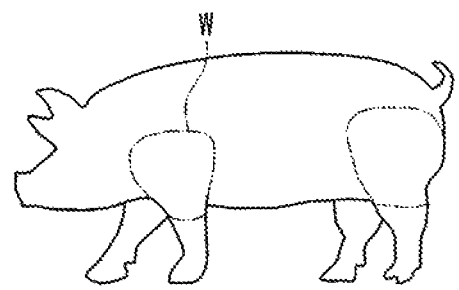
FIG. 3 is a view for explaining an arm part and a thigh part of a pig.

In the pre-processing step S10, pre-processing is manually performed on bone-in meat from an arm part of a pig schematically shown in FIG. 3 (hereinafter also referred to as a work and is designated by a reference numeral W). In the deboning method of FIG. 2, only the pre-processing step S10 is performed manually.

The deboning system is capable of deboning irrespective of whether the arm part is a left arm or a right arm. Note that, although the deboning system is suitable for deboning of the arm part, the deboning system can be applied to a thigh part, and can also be applied to the arm part and the thigh part of a cow or a sheep.

Figure 4:
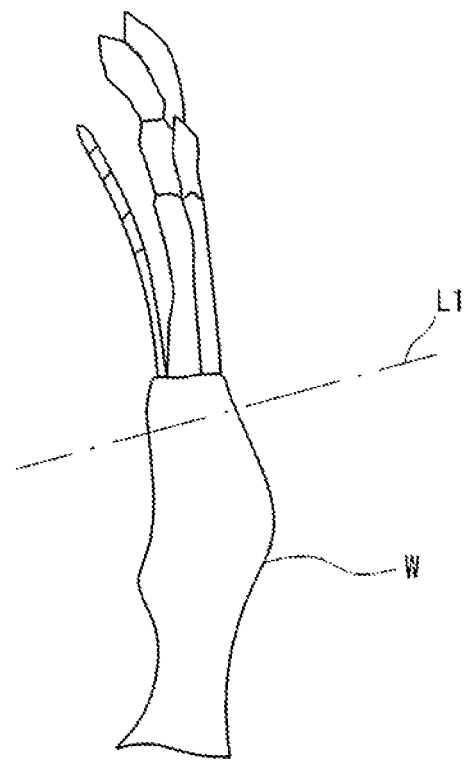
FIG. 4 is a view for explaining a pre-processing step in FIG. 2.
Figure 5:
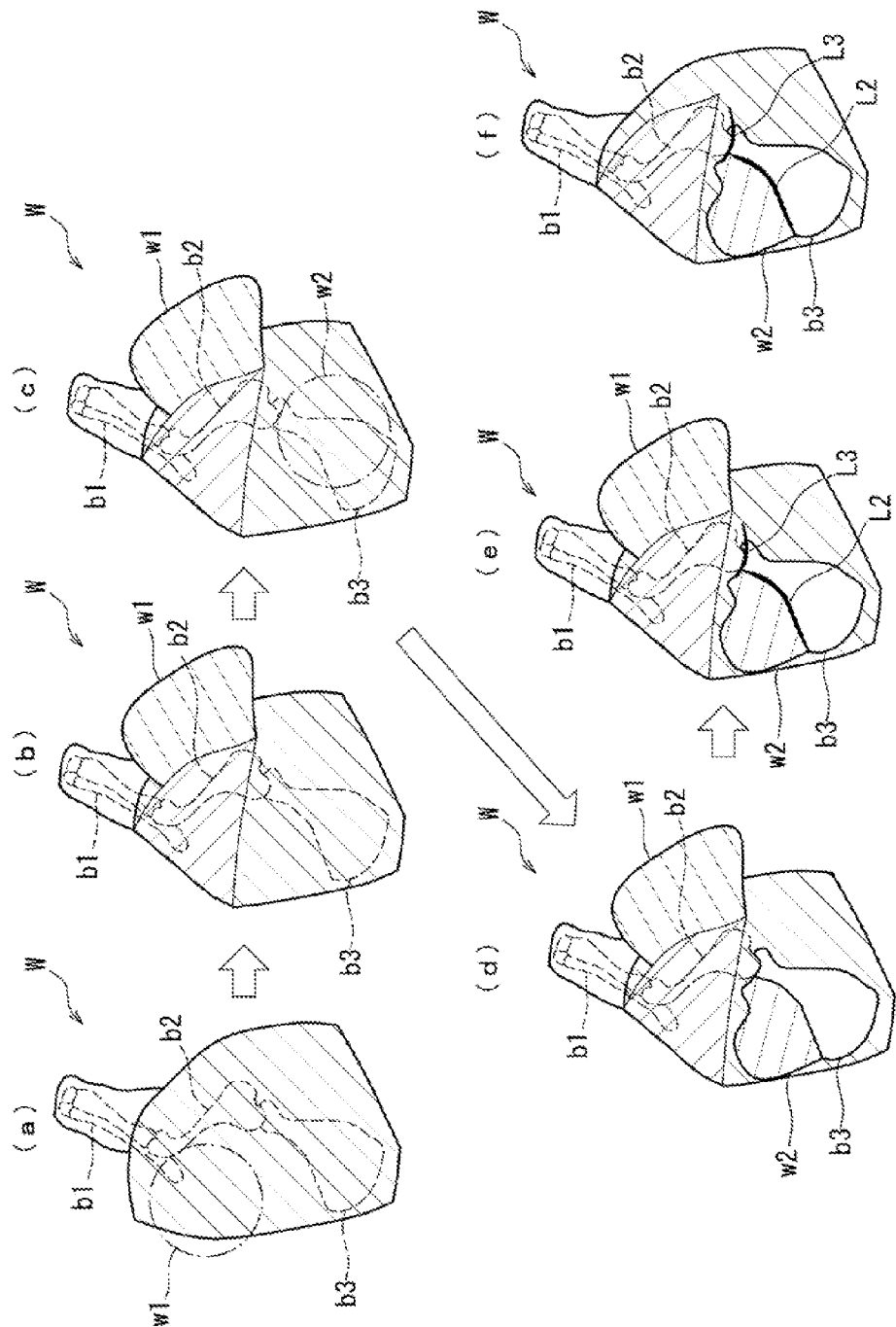
FIGS. 5(a), 5(b), 5(c), 5(d), 5(e), and 5(f) are views for explaining the pre-processing step in FIG. 2.

In the pre-processing step S10, a foot part is cut off along a line L1 in FIG. 4. In addition, in the pre-processing step S10, as shown in FIGS. 5(a) and 5(b), ribs (belly) w1 is turned over. Note that the work W of FIGS. 5(a), 5(b), 5(c), 5(d), 5(e), and 5(f) is a right arm (right work) and includes a forearm bone b1, an upper arm bone b2, and a shoulder blade b3 as bones.

Next, as shown in FIGS. 5(c) and 5(d), an upper meat w2 of the shoulder blade b1 is torn. As indicated by a line L2 in FIG. 5(e), incision making is performed along the shoulder blade b3, incision making is also performed on a joint between the shoulder blade b3 and the upper arm bone b2 as indicated by a line L3, and the pre-processing step S10 is ended.

Note that, in the pre-processing step S10, as shown in FIG. 5(f), the ribs w1 may also be cut off.

Figure 6:
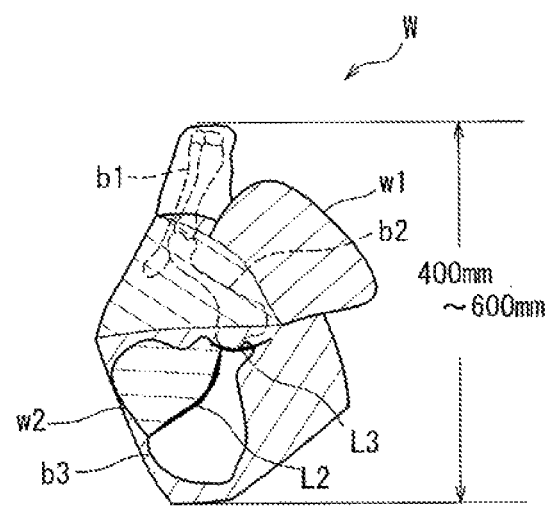
FIG. 6 is a view for explaining the size of a work after the pre-processing step in FIG. 2.
Figure 7:
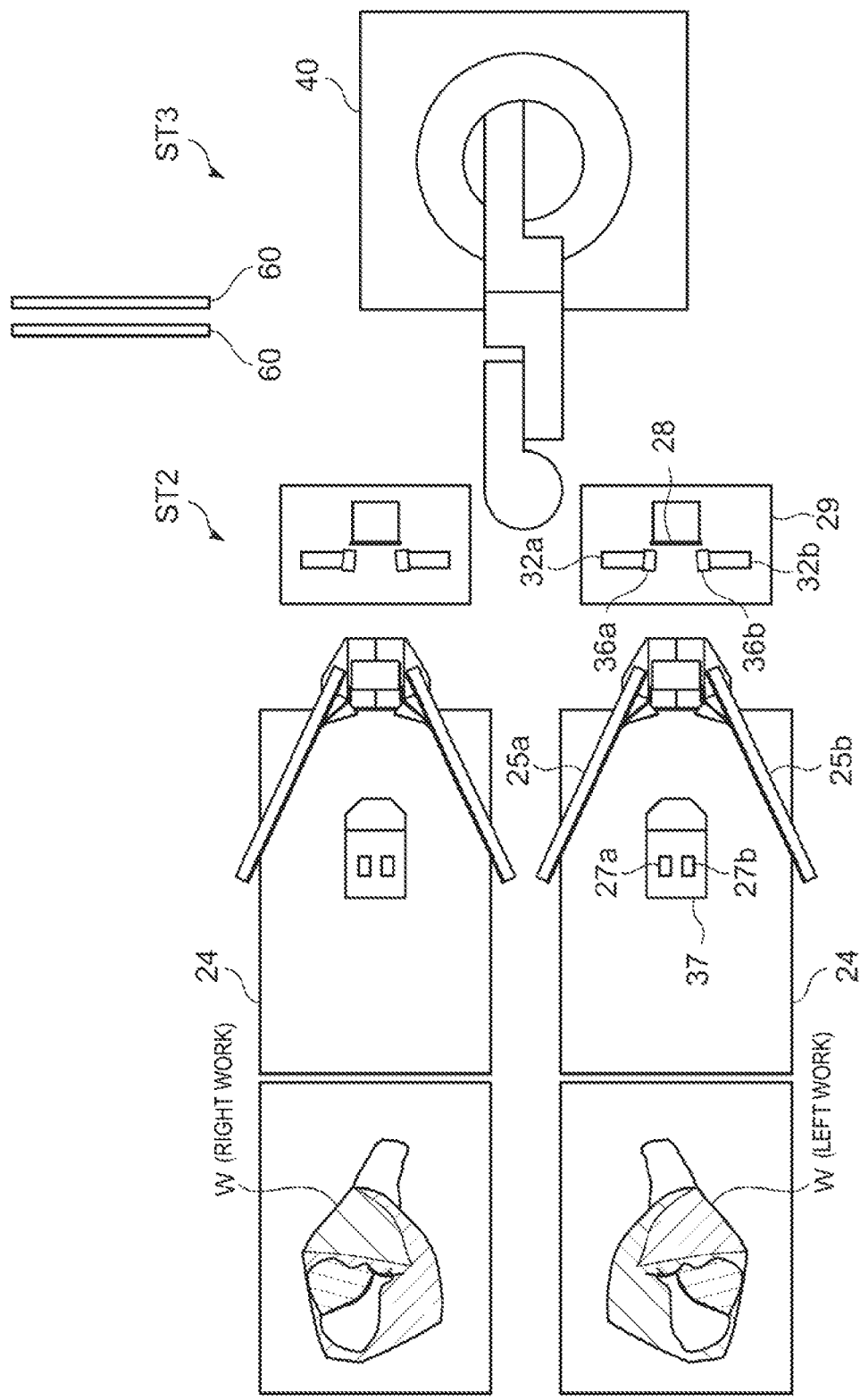
FIG. 7 is a plan view schematically showing the configuration of a left/right determination station together with a part of a suspension station.
Figure 8:
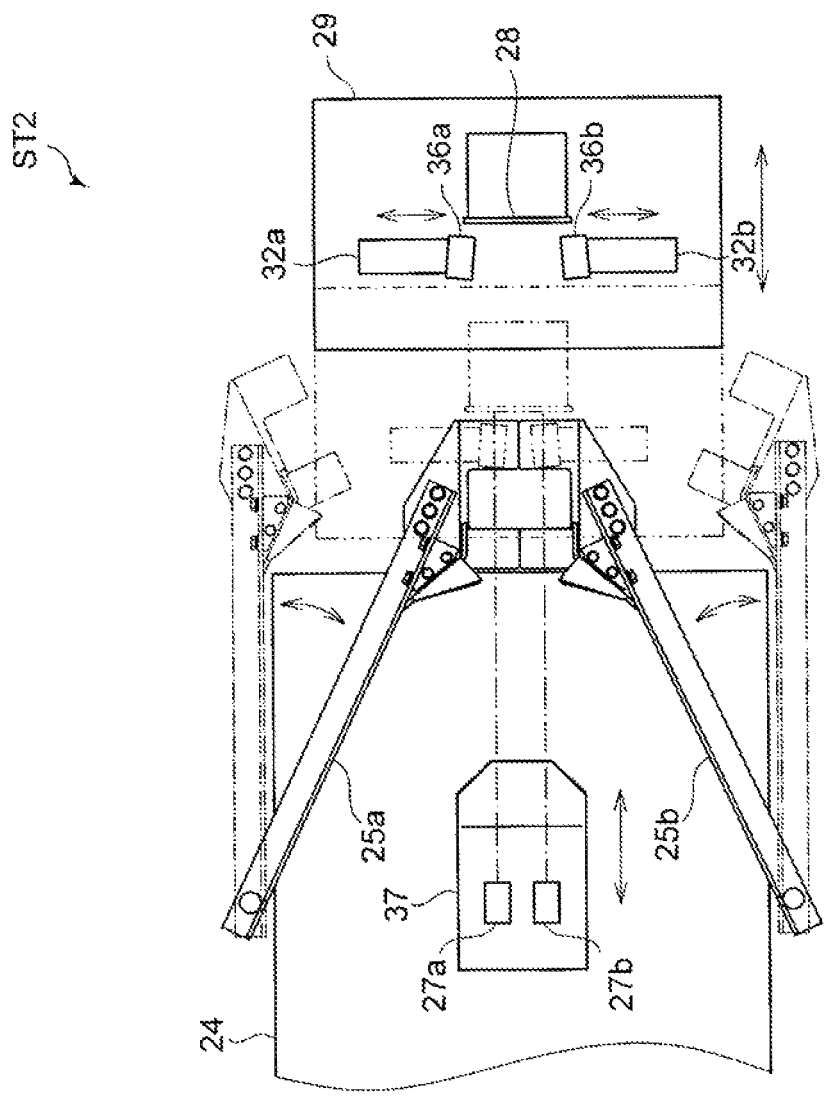
FIG. 8 is a plan view schematically showing the configuration of the left/right determination station.
Figure 9:
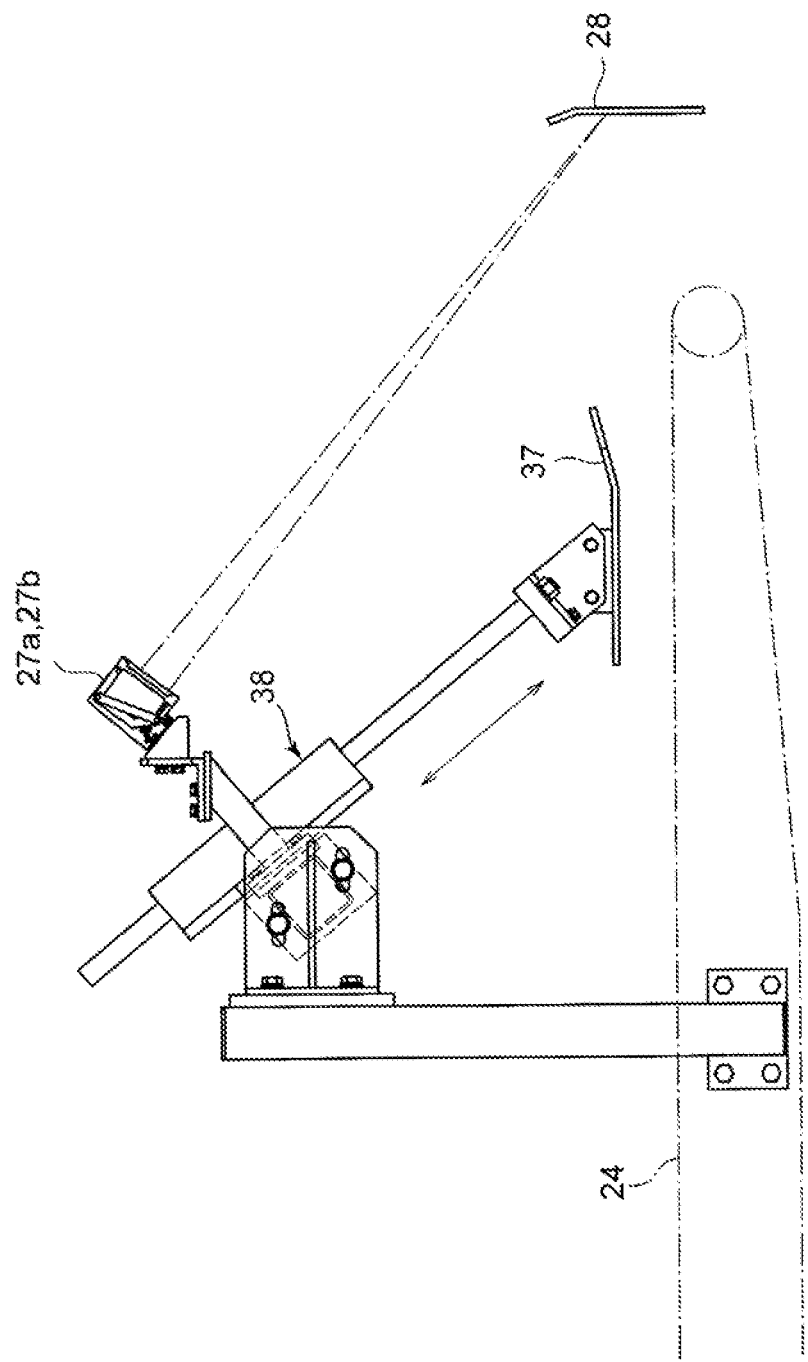
FIG. 9 is a side view for explaining the disposition of a photoelectric sensor.
Figure 10:
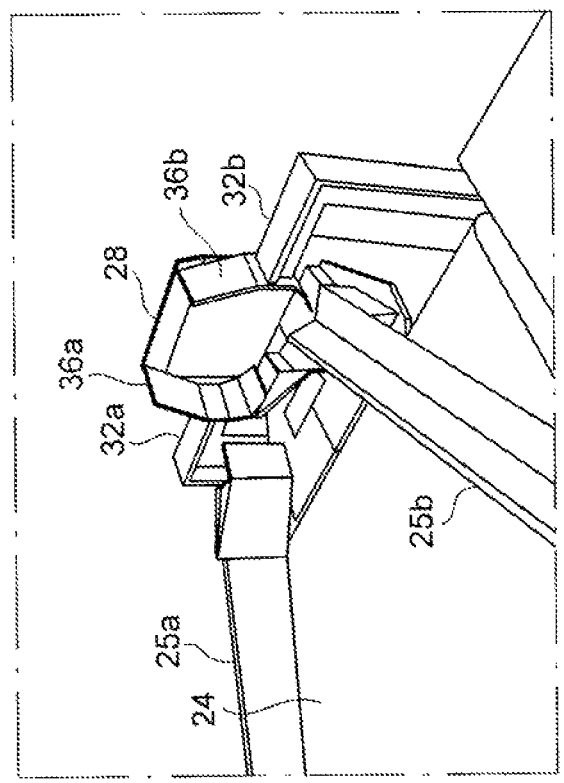
FIG. 10 is a perspective view schematically showing a part around a tip of a movement regulation bar.
Figure 11:
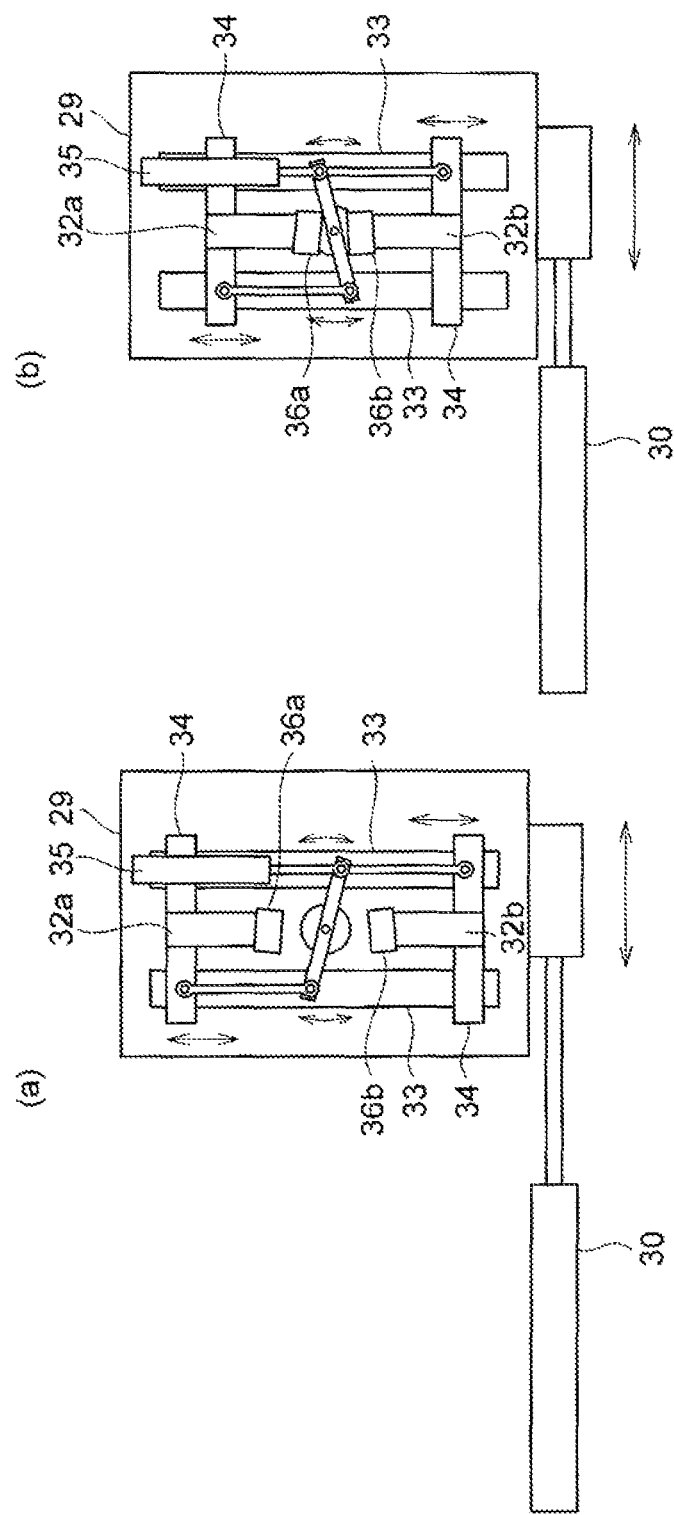
FIGS. 11(a) and 11(b) are views for explaining the operation of a clamp arm.
Figure 12:
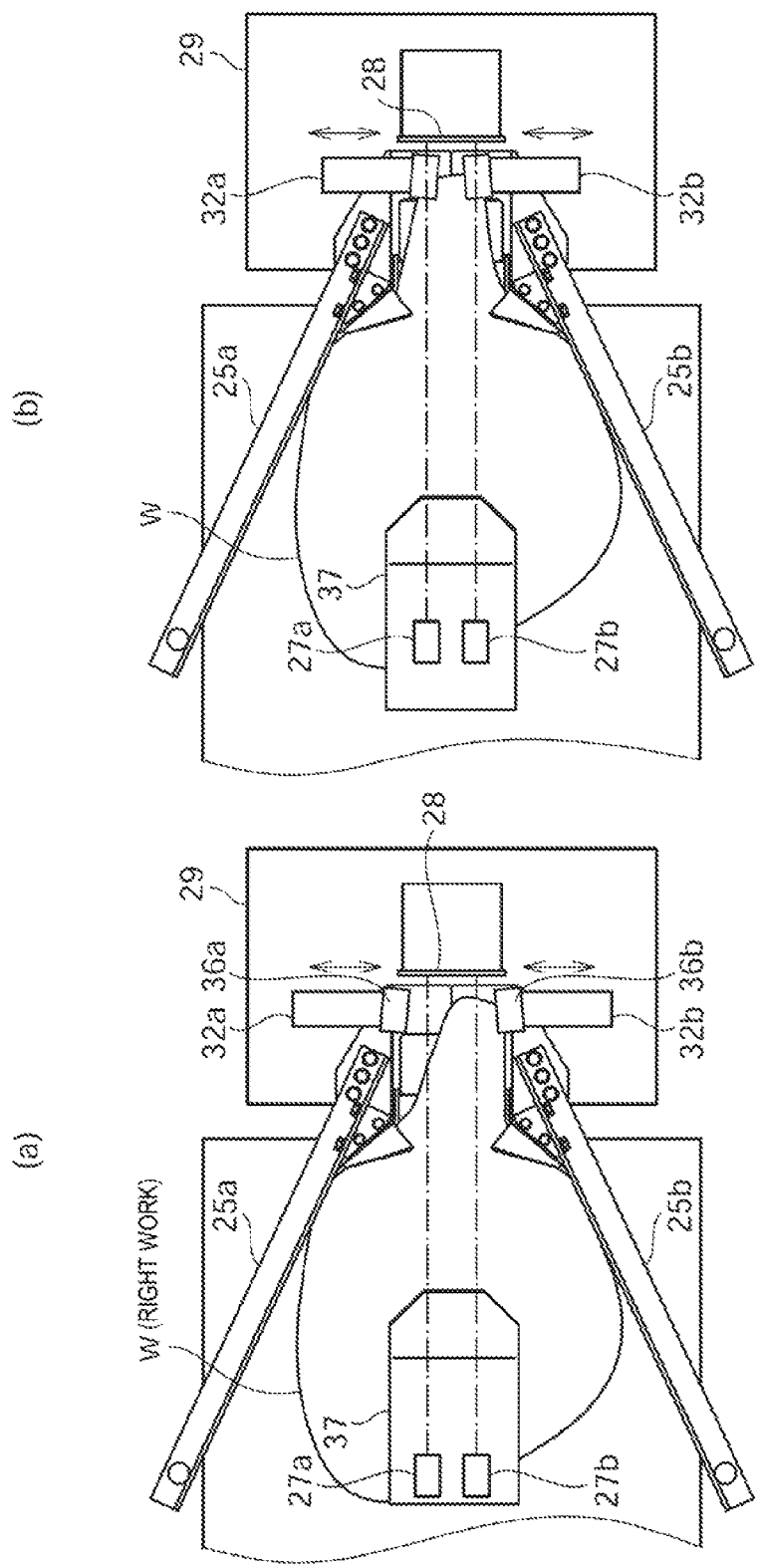
FIG. 12(a) is a view for explaining the posture of the work during left/right determination.
FIG. 12(b) is a view for explaining the posture of the work when a hooking member is stuck.
Figure 13:
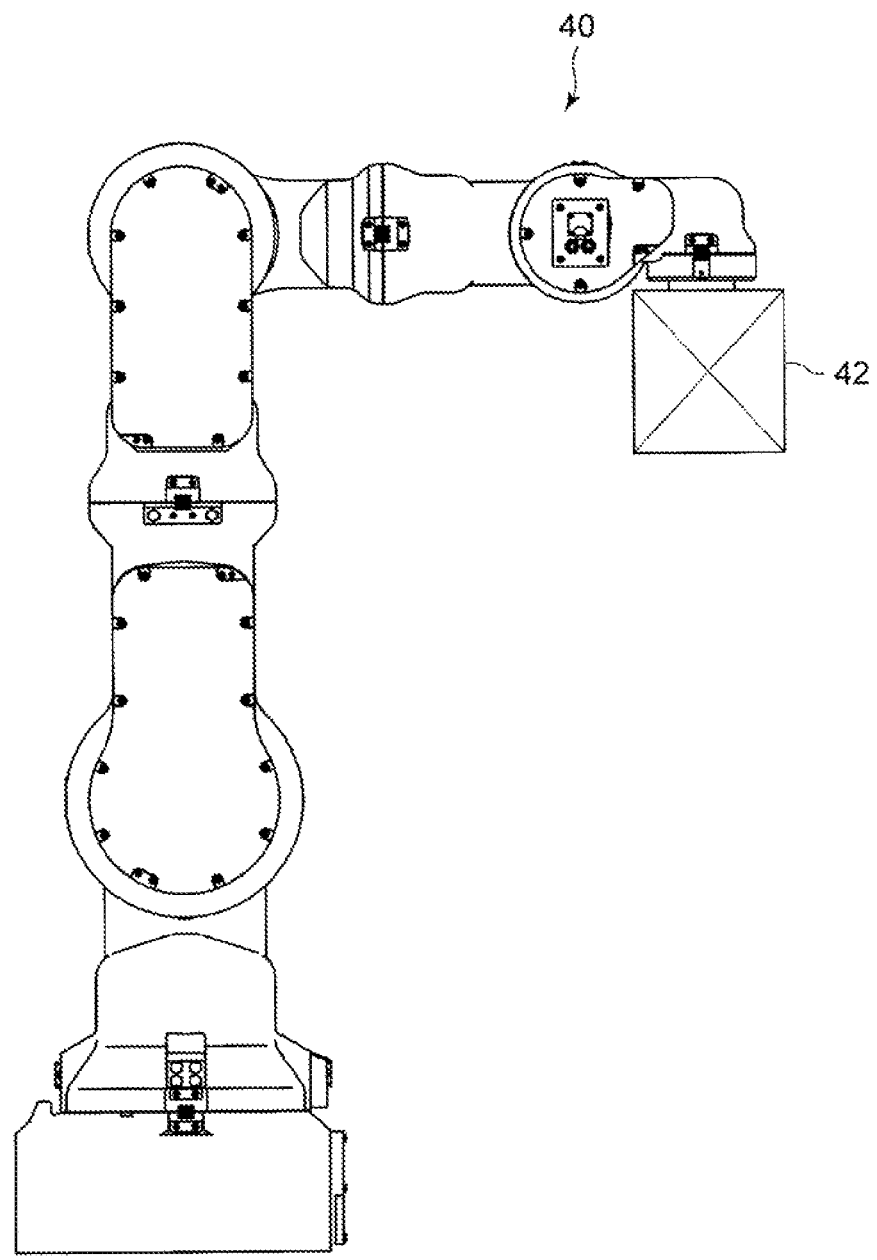
FIG. 13 is a side view schematically showing a robot arm.
Figure 14:
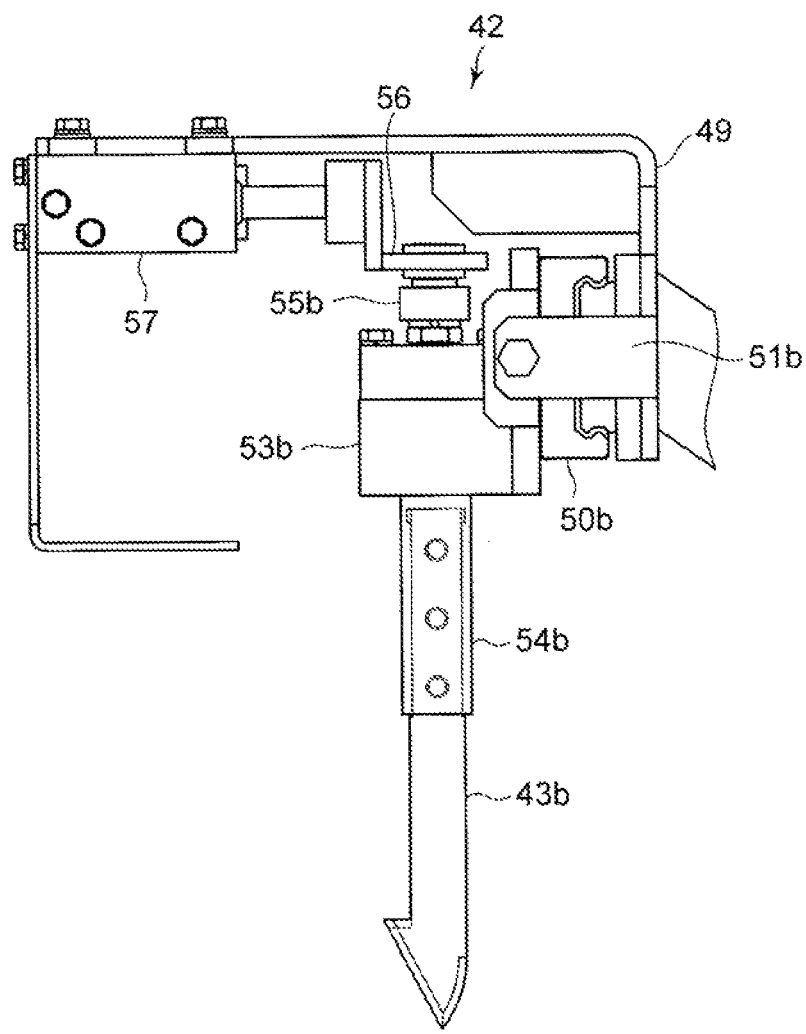
FIG. 14 is a side view schematically showing a hooking unit.
Figure 15:
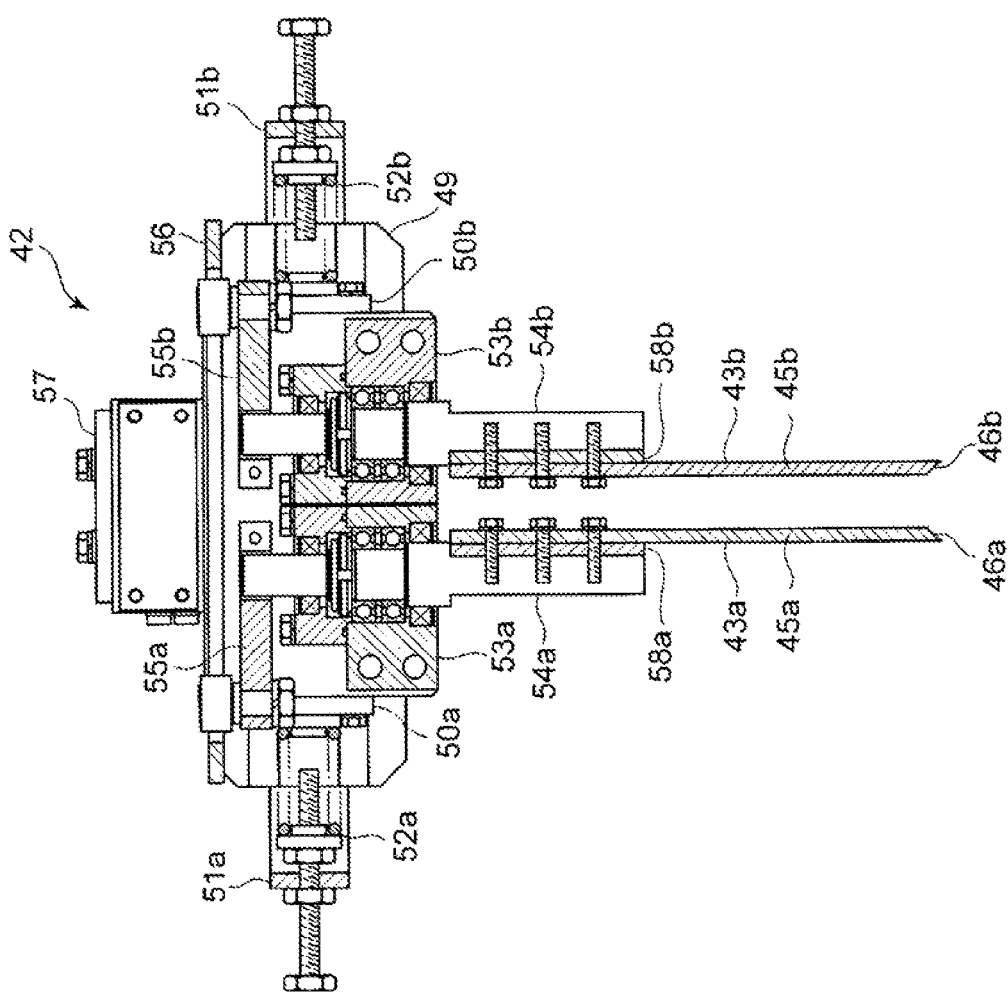
FIG. 15 is a schematic cross-sectional view of the hooking unit.
Figure 16:
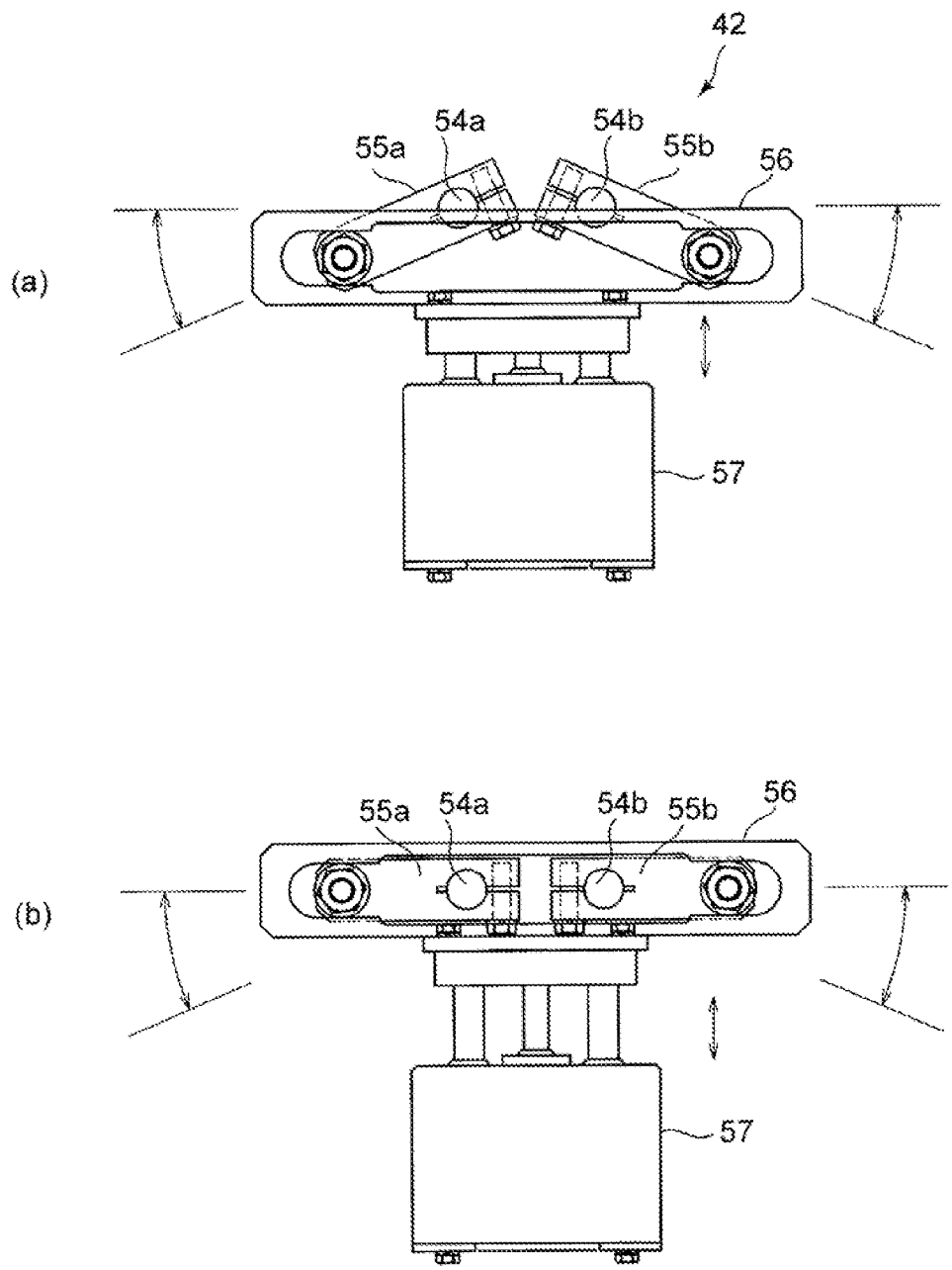
FIGS. 16(a) and 16(b) are views for explaining a rotation drive mechanism of the hooking member.
Figure 18:
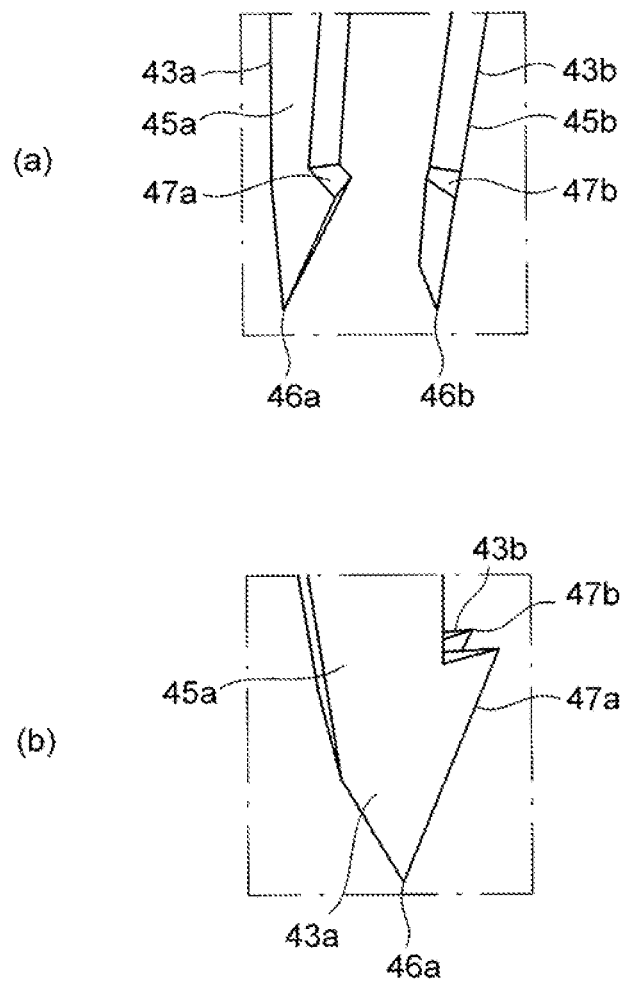
FIGS. 18(a) and 18(b) are perspective views of the tip side of the hooking member when viewed from different directions.
Figure 19:
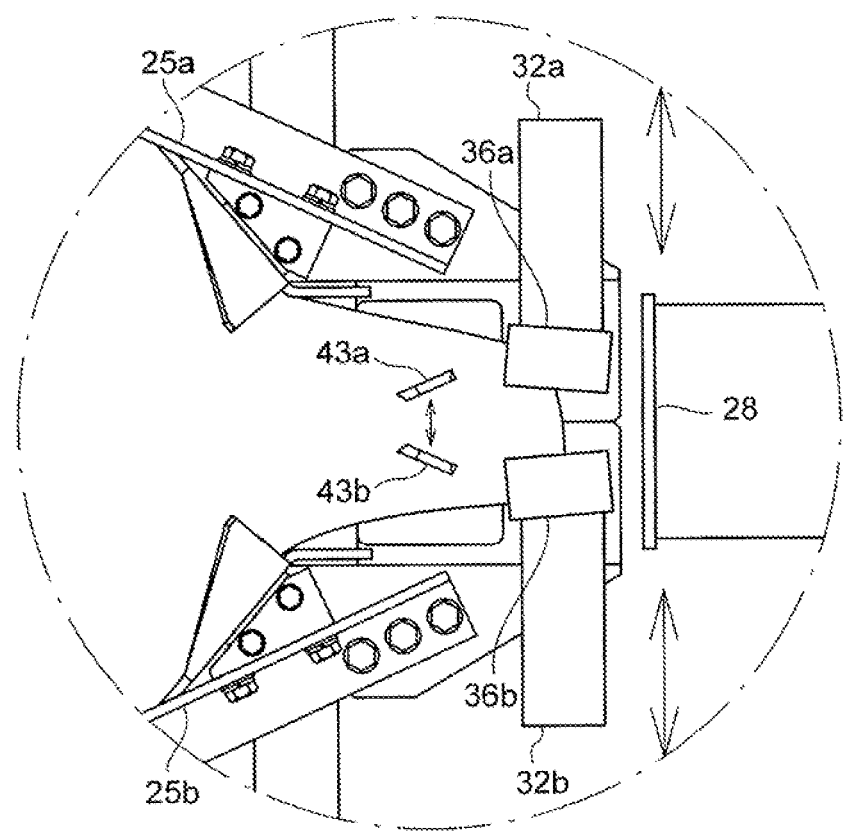
FIG. 19 is a view for explaining the disposition of the work and the hooking member when the hooking member is stuck into the work.
Figure 20:
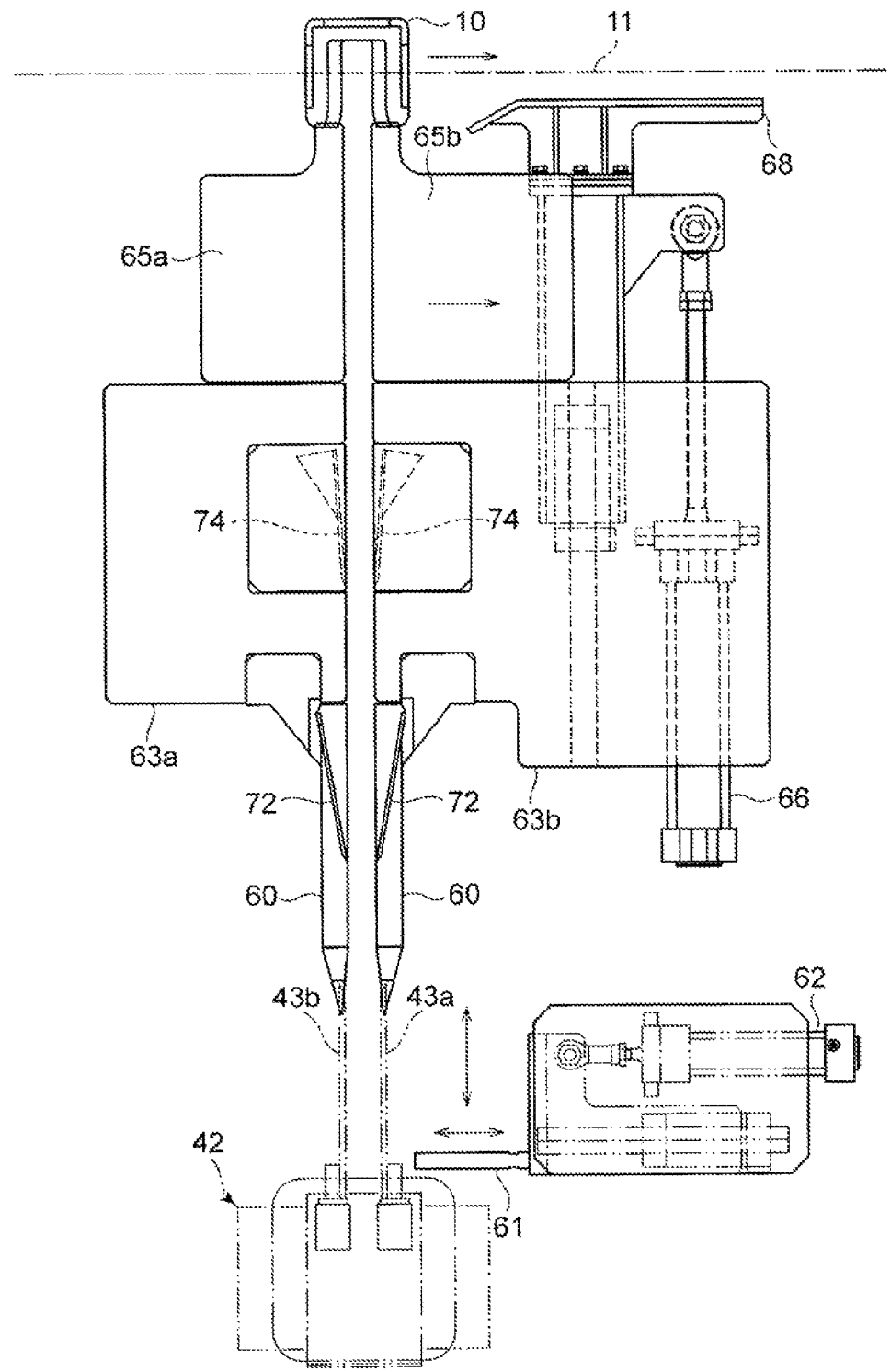
FIG. 20 is a plan view schematically showing a part of the suspension station.
Figure 21:
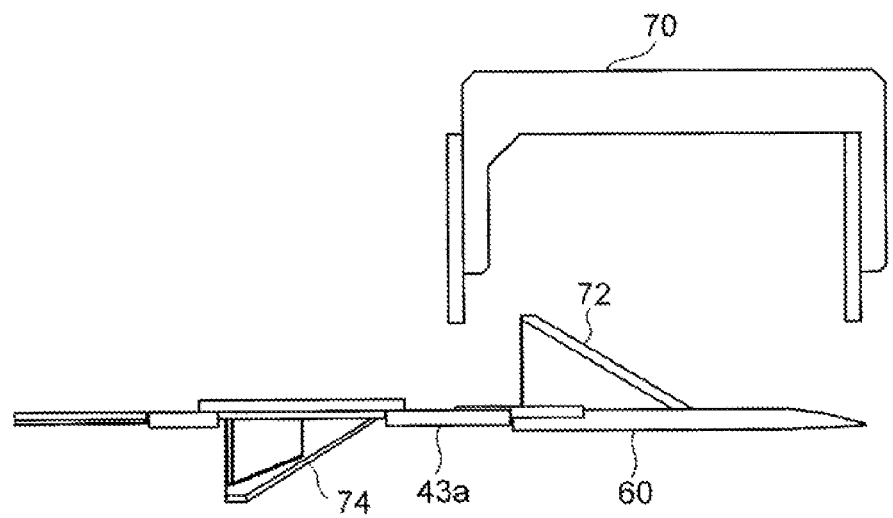
FIG. 21 is a side view schematically showing a part of the suspension station.
Figure 22:
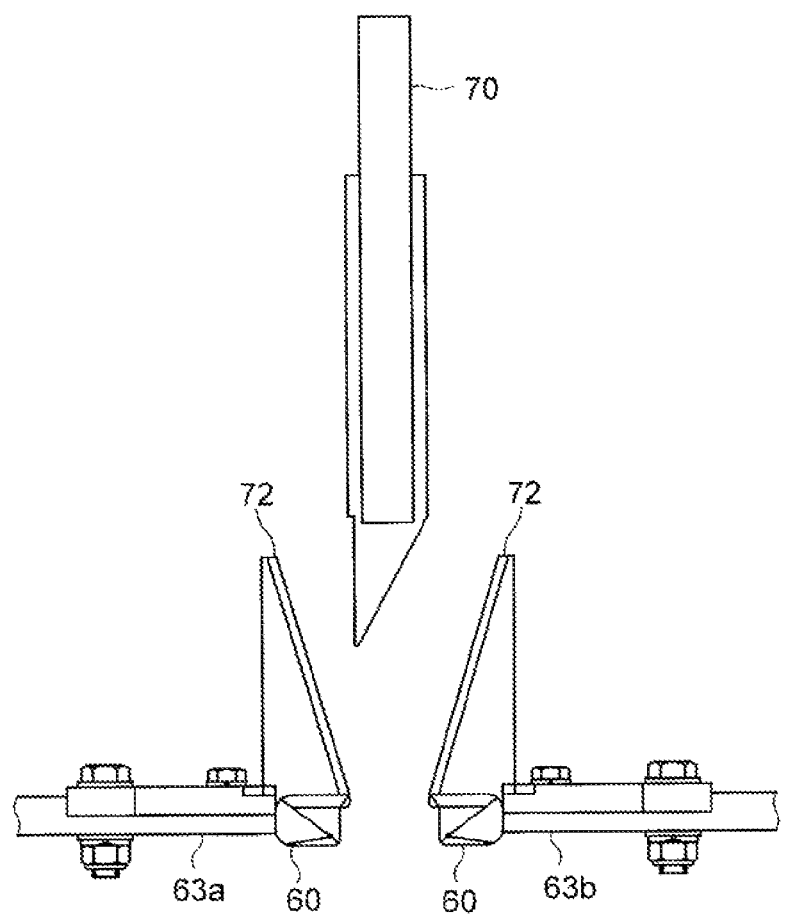
FIG. 22 is a front view schematically showing a part of the suspension station.
Figure 23:
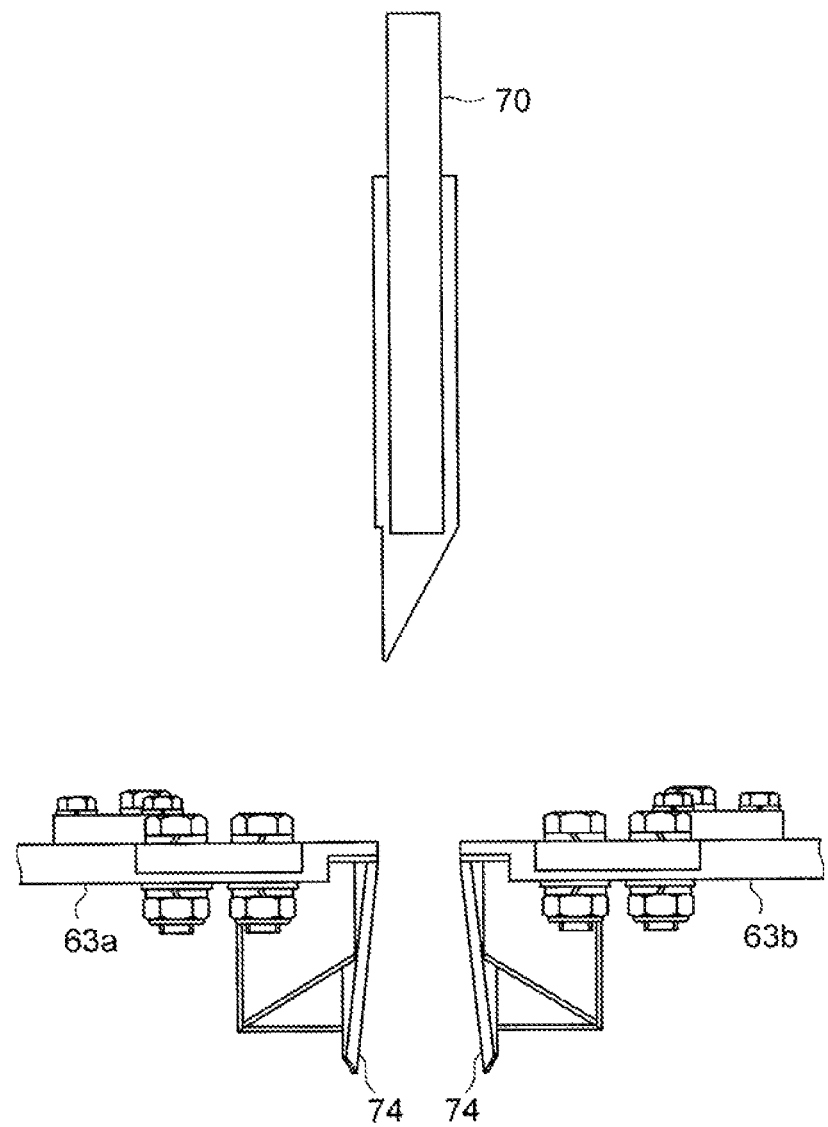
FIG. 23 is a front view schematically showing a part of the suspension station.
Figure 24:
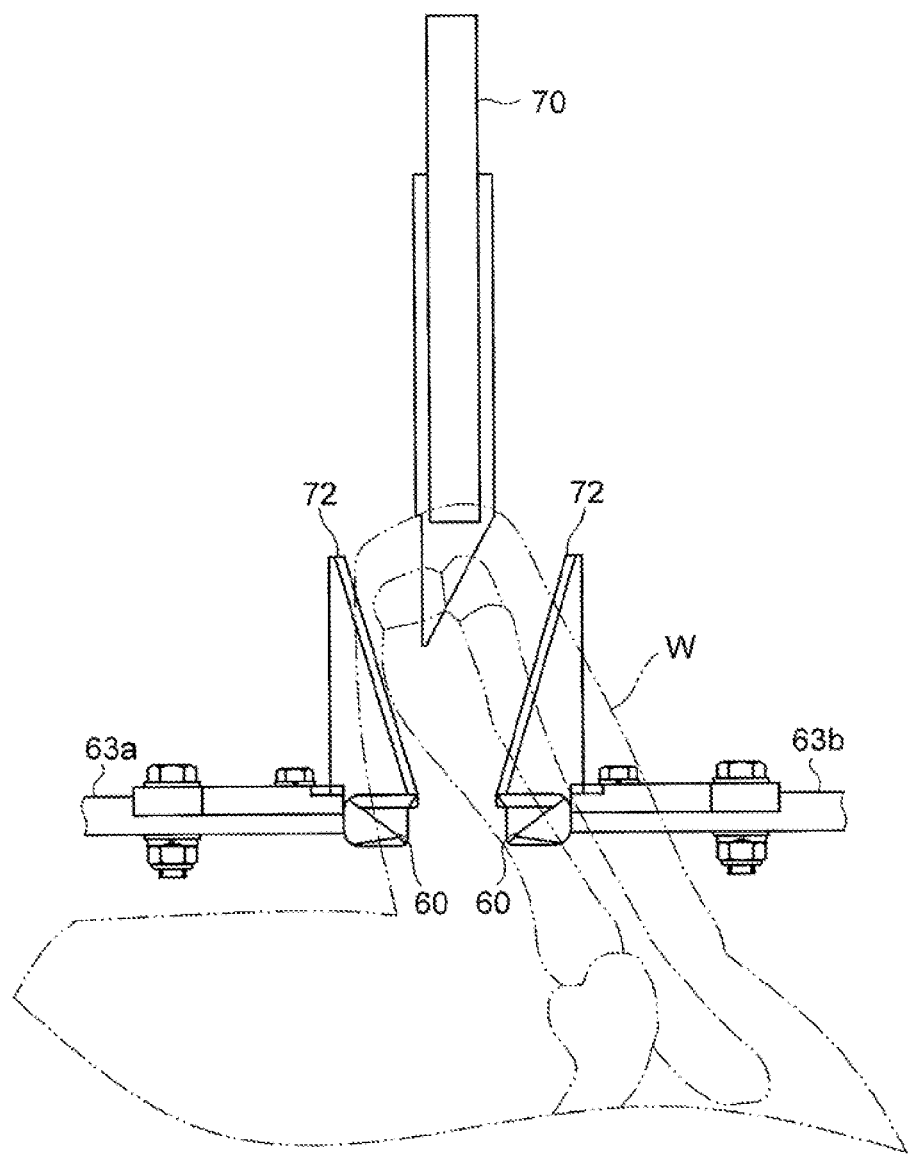
FIG. 24 is a view schematically showing a part of the suspension station together with the work.
Figure 25:
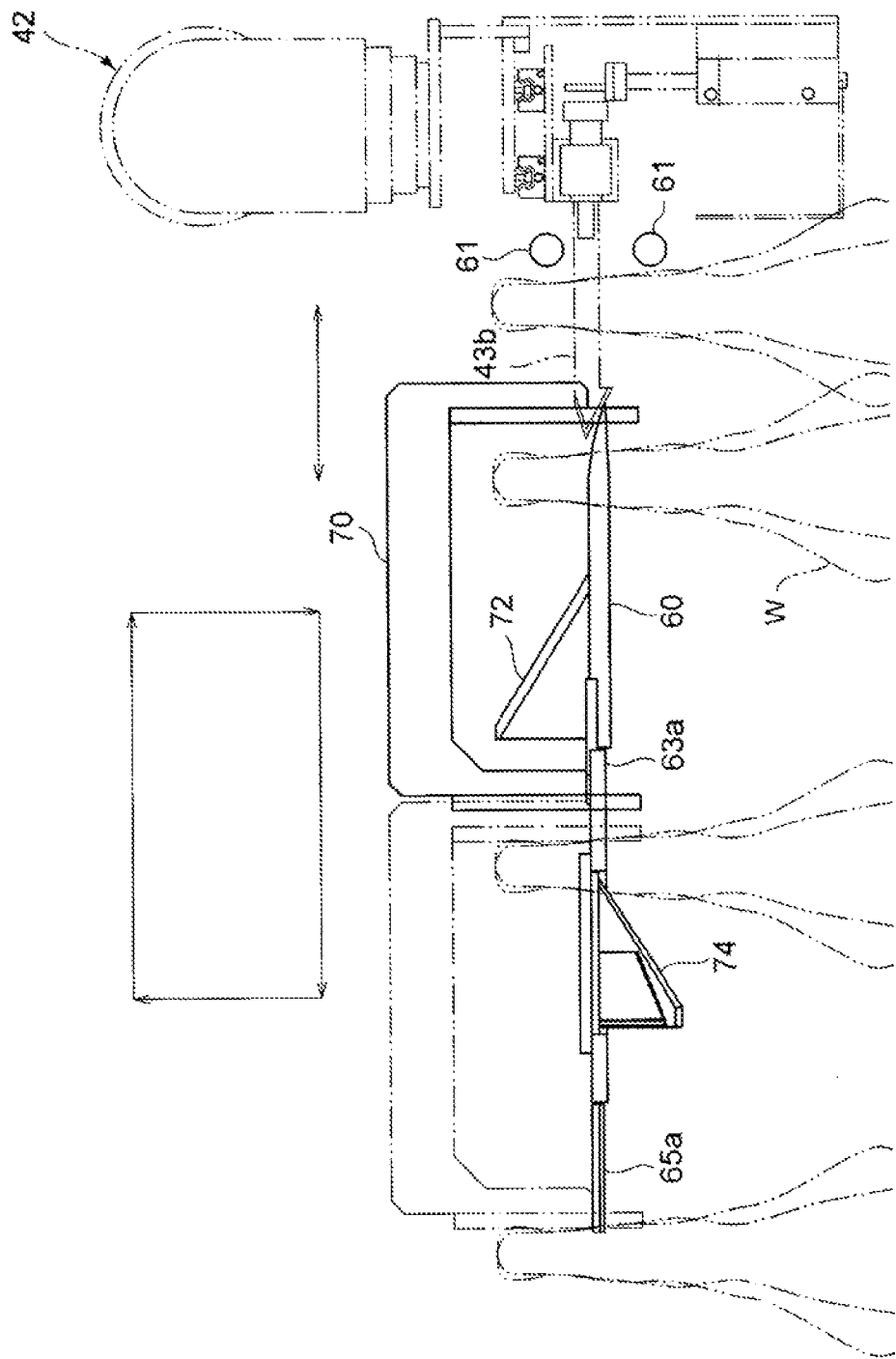
FIG. 25 is a side view schematically showing the state of the work which is conveyed in the suspension station.

FIG. 6 shows the work W after the pre-processing step S10, and the length of the work W deboned by the deboning system is, e.g., 400 mm to 600 mm.

[Left/Right Determination Step/Left/Right Determination Station]

FIGS. 7 to 12 are views for explaining the configuration of the left/right determination station ST2. Note that FIGS. 7 to 12 include the configuration of the suspension station ST3 partially.

The left/right determination station ST2 has belt conveyors 24 arranged in, e.g., two rows. The work W having been subjected to the pre-processing is disposed at the upstream end of each of the belt conveyors 24 by an operator, and is conveyed to the downstream end. Herein, the operator disposes the work W on the belt conveyor 24 such that the cut surface separated from the body of the work W is directed upward and the wrist side thereof is directed to the downstream side of the belt conveyor 24.

At the downstream end of the belt conveyor 24, a pair of movement regulation bars 25a and 25b are provided as a mechanism for regulating the movement of the work W. The movement regulation bars 25a and 25b can be opened and closed by an air cylinder which is not shown, and are closed during the execution of the left/right determination step S12.

The movement regulation bars 25a and 25b when they are closed form a substantially V-shape when viewed in two dimensions, and the interval between the movement regulation bars 25a and 25b is narrowed in a downstream direction in the direction of conveyance of the belt conveyor 24. At the top part of the V-shape, the movement regulation bars 25a and 25b are spaced apart from each other to form a gap. The movement of the work W is regulated in a state in which the tip part of the wrist side enters into the gap.

In addition, the left/right determination station ST has a left/right determination mechanism which determines whether the work W is a right arm (right work) or a left arm (left work) on the basis of the posture of the work W of which the movement is regulated. Specifically, the left/right determination mechanism is configured by a pair of photoelectric sensors 27a and 27b and a reflection plate 28.

The photoelectric sensors 27a and 27b are arranged side by side in the width direction of the belt conveyor 24 above the belt conveyor 24. The photoelectric sensors 27a and 27b are disposed so as to be capable of receiving reflected light from the reflection plate 28 when each of the photoelectric sensors 27a and 27b emits light toward the reflection plate 28. However, when the optical path is blocked by the tip part of the work W depending on the posture of the work W, one of the photoelectric sensors 27a and 27b cannot receive the reflected light. Consequently, the control device 21 can determine the left or the right of the work W on the basis of the light reception state of the reflected light by the photoelectric sensors 27a and 27b.

The reflection plate 28 is provided on a movable stage 29. The movable stage 29 can be brought close to or moved away from the downstream end of each of the belt conveyors 24 in the direction of conveyance of the belt conveyor 24 by an air cylinder 30.

Clamp arms 32a and 32b which fix the tip of the work W at the center of the gap between the movement regulation bars 25a and 25b are provided on the movable stage 29. The clamp arms 32a and 32b can be brought close to or moved away from the tip of the work W in the width direction of the belt conveyor 24.

Specifically, two rails 33 are provided on the movable stage 29 so as to be apart from each other, and sliders 34 are mounted on the rails 33. The slider 34 is slidable in the longitudinal direction of the rail 33, and the clamp arms 32a and 32b are fixed to the sliders 34. The sliders 34 are coupled to an air cylinder 35 via a link mechanism. Consequently, by controlling the air cylinder 35, it is possible to bring the clamp arms 32a and 32b close to or move them away from the tip of the work W.

Contact plate parts 36a and 36b which are bent so as to be depressed relative to the tip of the work W are provided at the tips of the clamp arms 32a and 32b, and the tip of the work W is reliably fixed by being pinched by the contact plate parts 36a and 36b.

In addition, a work holding member 37 is provided above the belt conveyor 24. The work holding member 37 can be brought close to or moved away from the work W of which the movement is regulated by a linear actuator 38. The work holding member 37 diagonally pushes the work W against the belt conveyor 24, and thereby pushes the work W toward the movement regulation bars 25a and 25b. The clamp arms 32a and 32b fix the tip of the work W held by the work holding member 37.

[Suspension Step First Forearm-Bone Incision Making Step/Suspension Station]

FIGS. 13 to 25 show the configuration of the suspension station ST3. The suspension station ST is a conveyance device which conveys the work W from the left/right determination station ST2 to the clamp 10 while involving posture change from a horizontally placed state to a suspended state. During the conveyance, the suspension station ST3 performs incision making on the forearm bone b1.

For the incision making, the suspension station ST3 has a robot arm 40 which can execute a predetermined operation. The robot arm 40 is, e.g., a 6-axis multi-joint robot, and a hooking unit 42 is attached to the tip of the robot arm 40 as an attachment.

Note that the first incision making station ST5, the second incision making station ST6, the shoulder blade removal station ST7, and the forearm-bone incision making station ST8 also have the robot arms 40 though the attachments are different.

The hooking unit 42 has two hooking members 43a and 43b. The robot arm 40 sticks the hooking members 43a and 43b into the tip part of the work W which is held by the movement regulation bars 25a and 25b, the clamp arms 32a and 32b, and the work holding member 37. That is, the movement regulation bars 25a and 25b, the clamp arms 32a and 32b, and the work holding member 37 constitute part of the suspension station ST3.

More specifically, the hooking members 43a and 43b have belt-like main body parts 45a and 45b, blade-like points 46a and 46b provided at ends on one side of the main body parts 45a and 45b, and barbs 47a and 47b provided on first sides of the main body parts 45a and 45b to be continuous with the points 46a and 46b.

In addition, the hooking unit 42 has a support mechanism for the hooking members 43a and 43b. The support mechanism supports the hooking members 43a and 43b such that the hooking members 43a and 43b are in parallel with each other with an elastically changeable interval therebetween, and are also rotatable about rotation axes along the longitudinal axes of the main body parts 45a and 45b.

Further, the hooking unit 42 has a rotation drive mechanism which rotates the hooking members 43a and 43b about the rotation axes. Note that the rotation axes are set such that the first sides of the main body parts 45a and 45b provided with the barbs 47a and 47b are brought close to or moved away from each other with the rotation.

Specifically, the hooking unit 42 has a main frame 49, and two movable stages 50a and 50b are attached to the main frame 49 via, e.g., a linear guide so as to be able to be brought close to or moved away from each other. Brackets 51a and 51b are attached to the main frame 49 so as to pinch the movable stages 50a and 50b, and compression coil springs 52a and 52b are provided between the brackets 51a and 51b and the movable stages 50a and 50b. Consequently, an elastic force acts on the movable stages 50a and 50b such that the movable stages 50a and 50b are moved close to each other.

Mount blocks 53a and 53b are fixed to the movable stages 50a and 50b, and the mount blocks 53a and 53b rotatably support rotary members 54a and 54b via bearings. Drive arms 55a and 55b are coupled to first ends of the rotary members 54a and 54b protruding from the mount blocks 53a and 53b, and the drive arms 55a and 55b are connected to oblong holes of a coupling plate 56 using pins. The coupling plate 56 is coupled to an air cylinder 57 fixed to the main frame 49.

On the other hand, to second ends of the rotary members 54a and 54b protruding from the mount blocks 53a and 53b, the hooking members 43a and 43b are fixed via spacers 58a and 58b on an as needed basis.

In the hooking unit 42, when the air cylinder 57 is extended or retracted, the drive arms 55a and 55b rotate, and the hooking members 43a and 43b are thereby rotated together with the rotary members 54a and 54b. That is, the air cylinder 57 constitutes an actuator for rotating the hooking members 43a and 43b, and the drive arms 55a and 55b and coupling plate 56 constitute a link which couples the actuator and the rotary members 54a and 54b.

In addition, the hooking unit 42 further has a swing regulation mechanism which regulates the swing of the work W during the movement of the work W. Specifically, the hooking unit 42 has a swing prevention plate 59 having an L-shaped cross section which is coupled to the main frame 49.

The robot arm 40 sticks the points 46a and 46b of the hooking members 43a and 43b into the tip part of the work W in the horizontally placed state such that the forearm bone b1 in the tip part is pinched. At this point, the rotation drive mechanism rotates the hooking members 43a and 43b such that the interval between the first sides of the main body parts 45a and 45b provided with the barbs 46a and 46b is narrower than the interval between the second sides thereof.

In addition, the robot arm 40 sticks the points 46a and 46b of the hooking members 43a and 43b into the tip part of the work W such that the first sides of the main body parts 45a and 45b provided with the barbs 47a and 47b are disposed on the elbow side of the work W, and the second sides of the main body parts 45a and 45b are disposed on the wrist side thereof.

Subsequently, the robot arm 40 moves the work W into which the hooking members 43a and 43b are stuck to the entrance of guide rails 60. The guide rails 60 are guide members that define a groove for conveying the suspended work W.

In the vicinity of the entrance of the guide rails 60, two push rods 61 for transferring the work W from the hooking unit 42 to the guide rails 60 are disposed. The push rods 61 extend in a horizontal direction orthogonal to the groove of the guide rails 60. The push rods 61 can be moved in a longitudinal direction thereof by an air cylinder 62, and can be moved in a direction parallel with the groove of the guide rails 60 by a drive mechanism which is not shown.

Note that, when the work W is detached from the hooking members 43a and 43b by the push rods 61, the rotation drive mechanism rotates the hooking members 43a and 43b such that the interval between the first sides of the main body parts 45 approaches or preferably matches the interval between the second sides thereof. At this point, the robot arm 40 disposes the hooking unit 42 such that the first sides of the main body parts 45, i.e., the barbs 47a and 47b are positioned on a lower side.

The guide rails 60 are coupled to guide plates 63a and 63b, and the guide plates 63a and 63b also define the groove which conveys the suspended work W. Synchronization plates 65a and 65b are provided adjacent to the guide plates 63a and 63b. The synchronization plates 65a and 65b also define the groove which conveys the suspended work W.

The synchronization plates 65a and 65b can be moved along the endless track 11 in synchronization with the clamp 10 which goes around the endless track 11 by a drive mechanism which is not shown. An air cylinder 66 is fixed to the guide plate 63b, and the air cylinder 66 pushes the work W suspended from the synchronization plates 65a and 65b into the clamp 10 via a pusher 68.

The suspension station ST3 has a fork 70 for carrying the work W from the entrance of the guide rails 60 to the synchronization plates 65a and 65b. The fork 70 can be inserted into the groove and can be moved along the groove by a drive mechanism which is not shown. One work W is conveyed by a first nail of the fork 70, and then conveyed by a second nail thereof.

Further, triangular upstream side stationary blades 72 which protrude upward from both sides of the groove are fixed to the guide rails 60, and triangular downstream side stationary blades 74 which protrude downward from both sides of the groove are fixed to the guide plates 63a and 63b.

Consequently, while the work W is conveyed along the groove, incision making is performed on the tip part of the work W, i.e., meat around the forearm bone by the upstream side stationary blades 72 and the downstream side stationary blades 74. At this point, in each of the upstream side stationary blades 72, the height of the cutting edge is gradually increased in the conveyance direction, and the incision making is performed by using the weight of the work W. The downstream side stationary blades 74 perform the incision making such that incisions are continuous with incisions made by the upstream side stationary blades 72.

Figure 26:
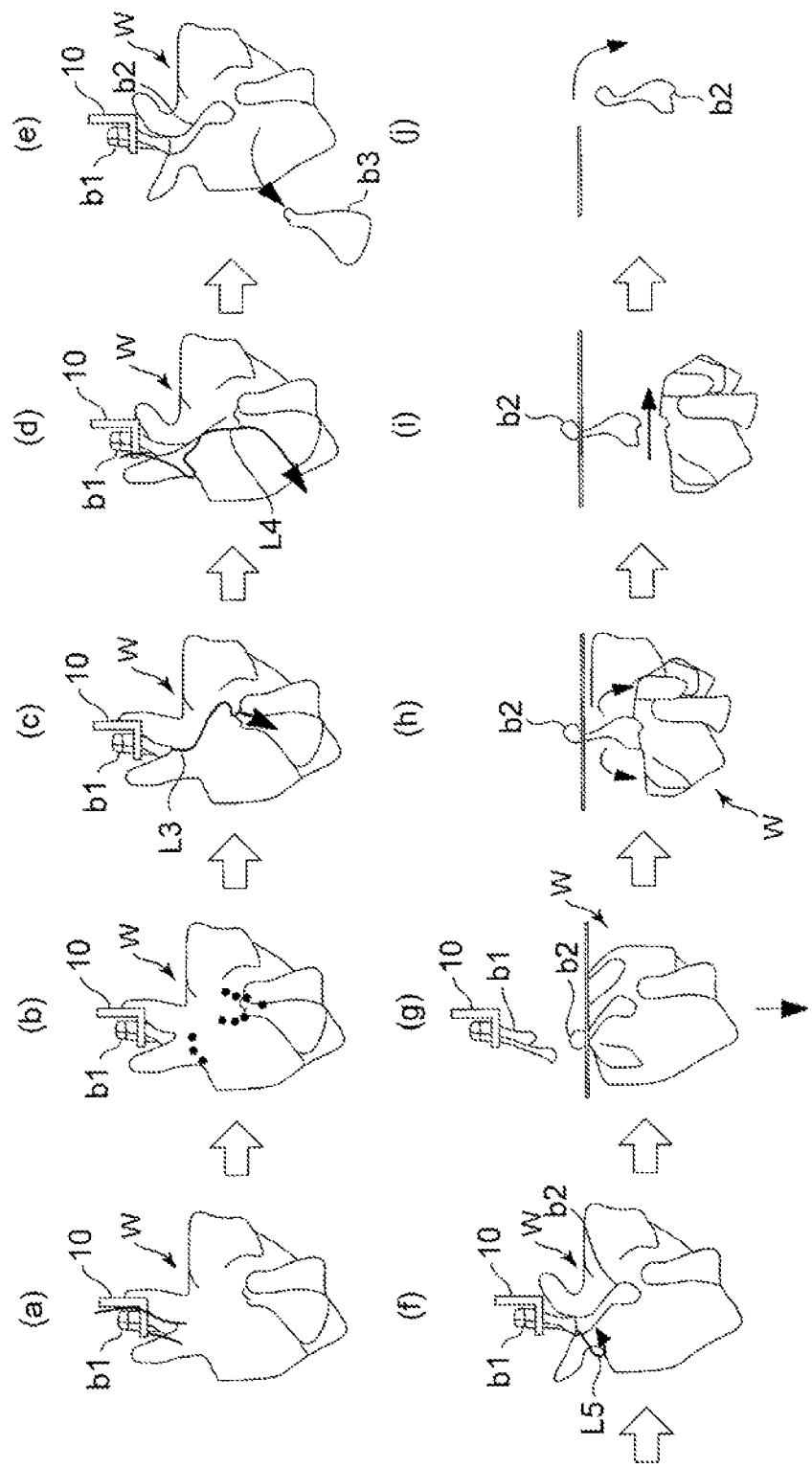
FIGS. 26(a), 26(b), 26(c), 26(d), 26(e), 26(f), 26(g), 26(h), 26(i), and 26(j) are views for explaining the deboning method executed by the deboning system.

That is, the upstream side stationary blade 72 and the downstream side stationary blade 74 execute the first forearm-bone incision making step S16. As the result of the first forearm-bone incision making step S16, as shown in FIG. 26(a), the wrist side of the forearm bone b1 is exposed, and the exposed wrist side of the forearm bone is held by the clamp 10.

[First to Fifth Clamp Rotation Steps/First to Fifth Clamp Rotation Devices]

Figure 27:
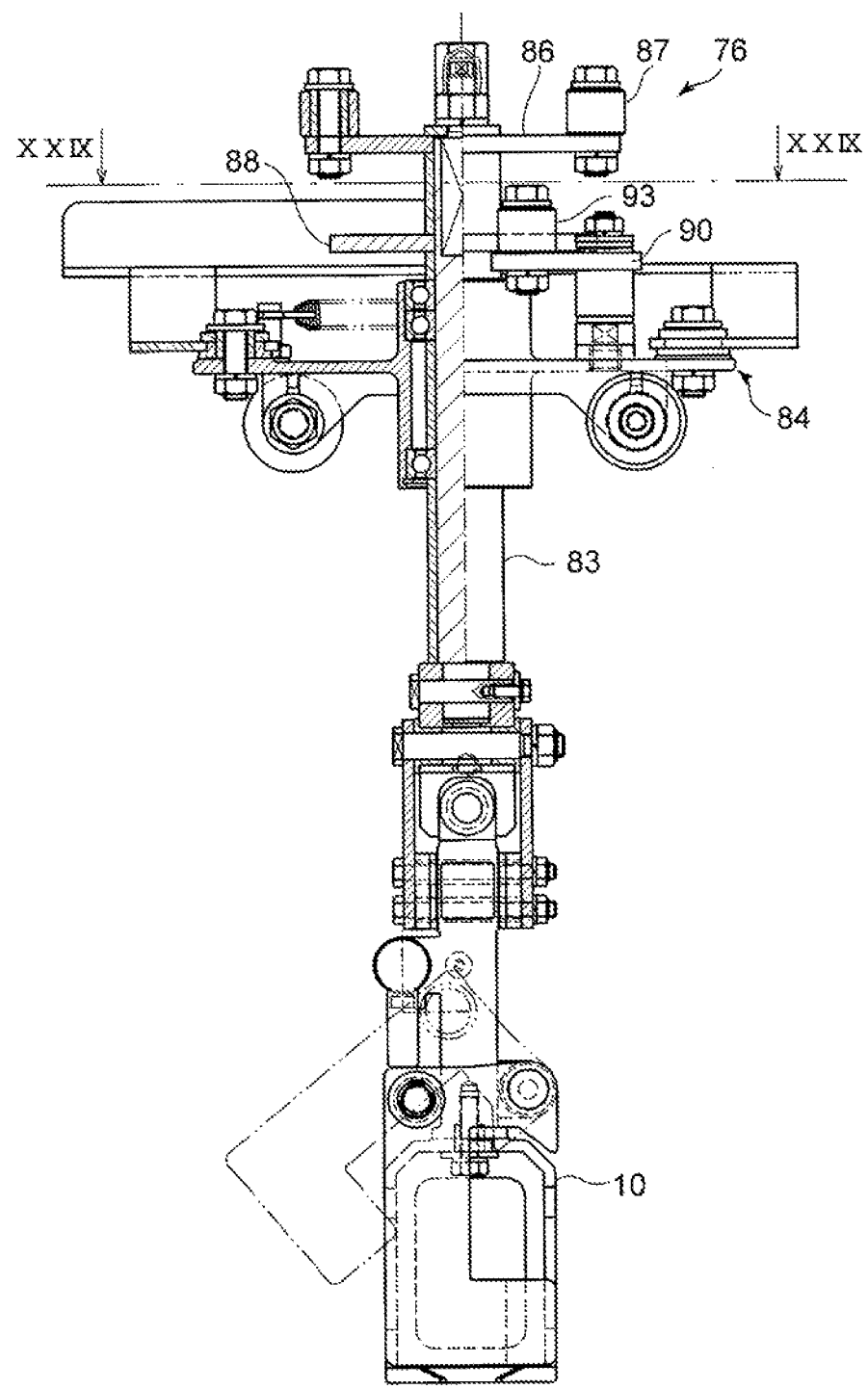
FIG. 27 is a half cross-sectional view schematically showing a clamp device for conveying the work.
Figure 28:
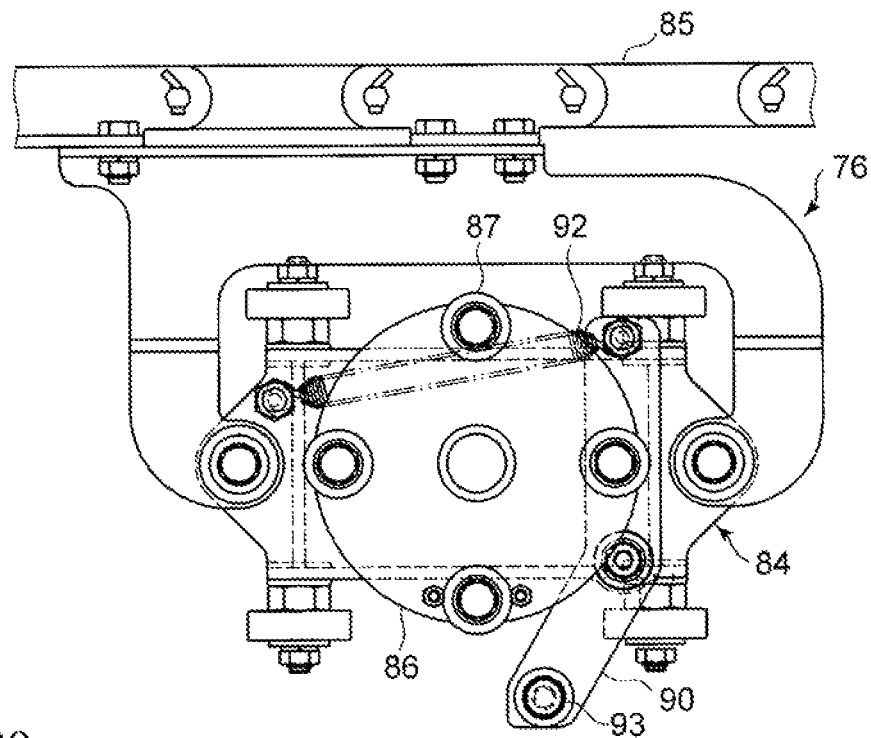
FIG. 28 is a top view schematically showing the clamp device of FIG. 27.
Figure 29:
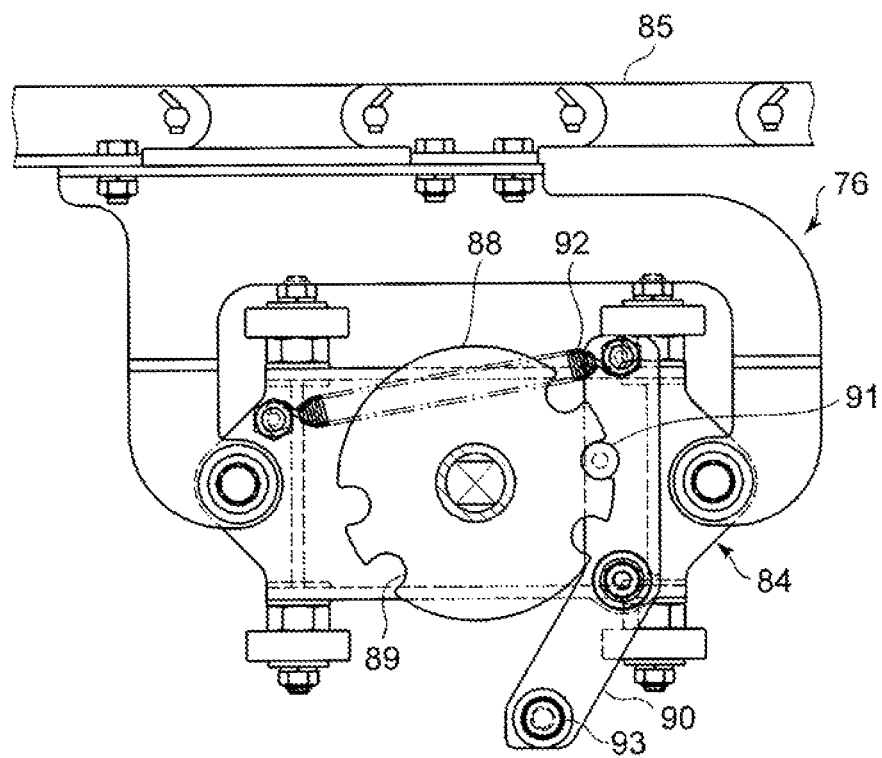
FIG. 29 is a cross-sectional view along an XXIX-XXIX line of FIG. 27.
Figure 30:
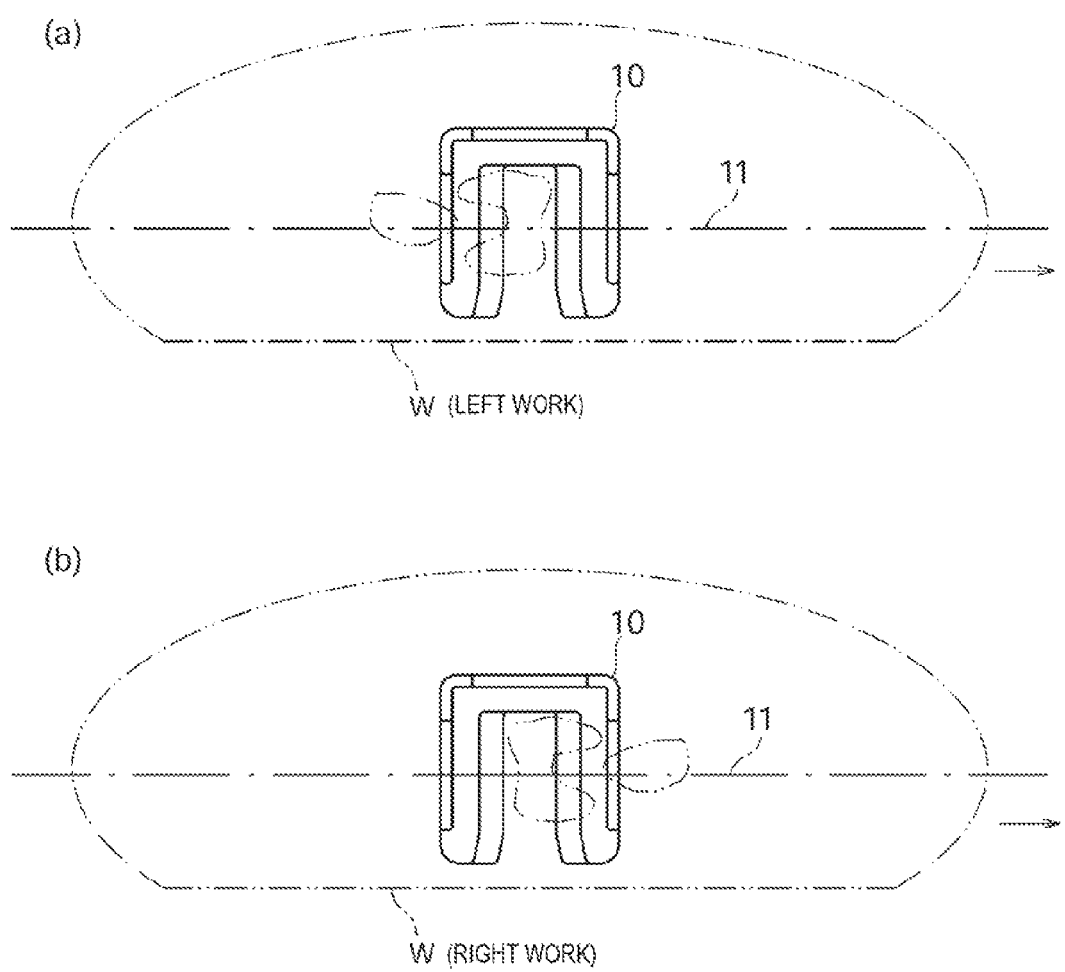
FIG. 30(a) is a plan view schematically showing a left work W and a clamp immediately after the work is suspended from the clamp.
FIG. 30(b) is a plan view schematically showing a right work W and the clamp immediately after the work is suspended from the clamp.
Figure 31:
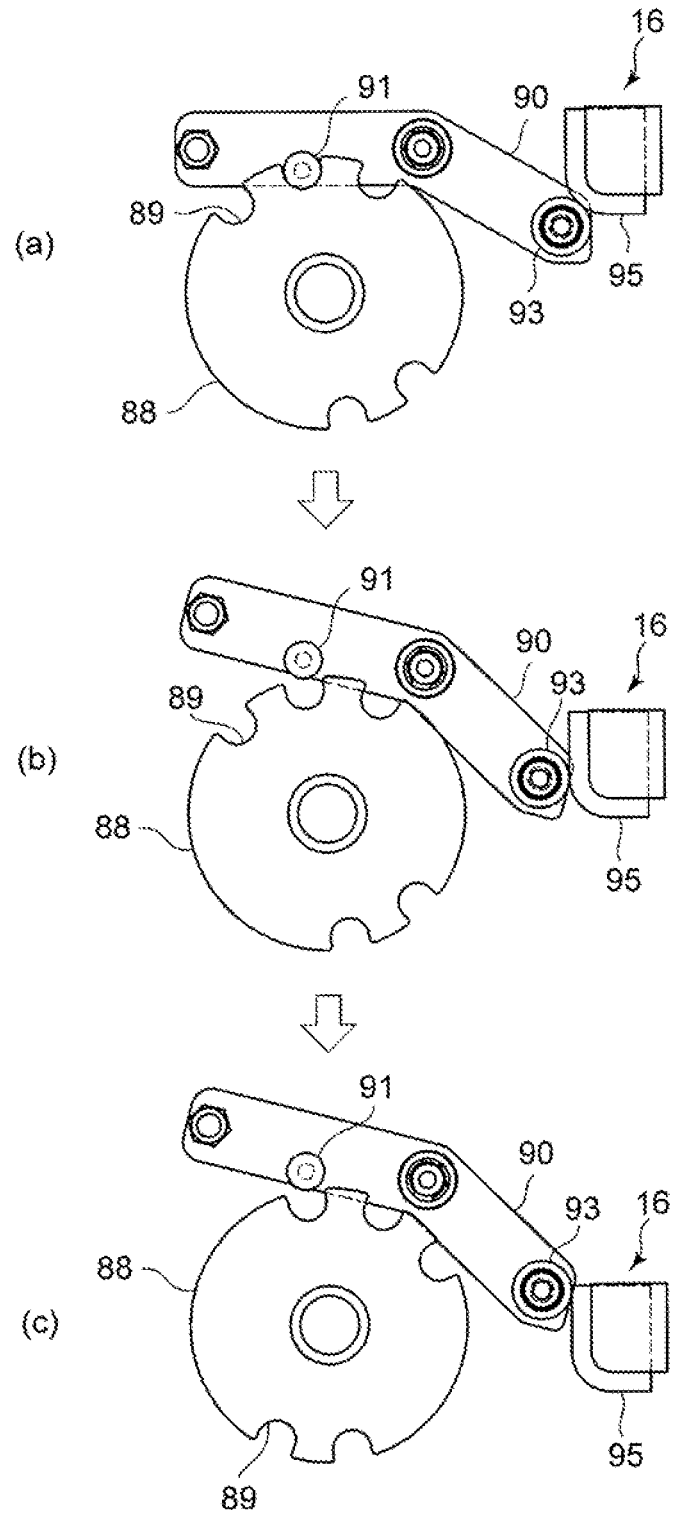
FIGS. 31(a), 31(b), and 31(c) are views for explaining the operation of a first clamp rotation device.
Figure 32:
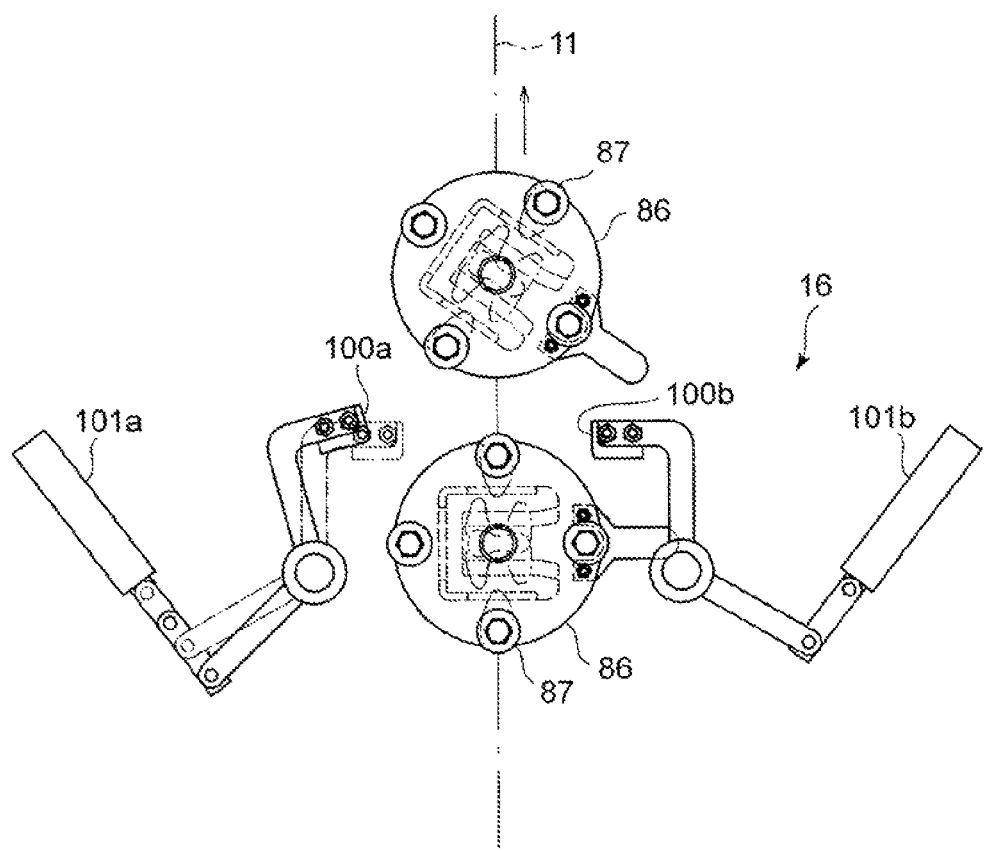
FIG. 32 is a view for explaining the operation of the first clamp rotation device.
Figure 33:
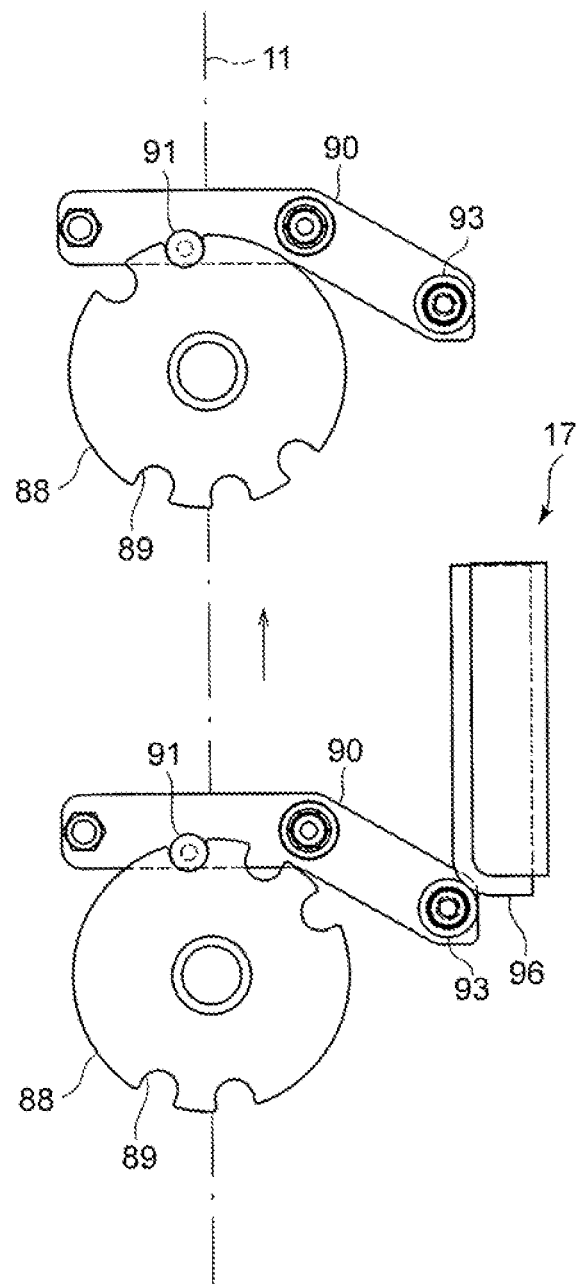
FIG. 33 is a view for explaining the operation of a second clamp rotation device.
Figure 34:
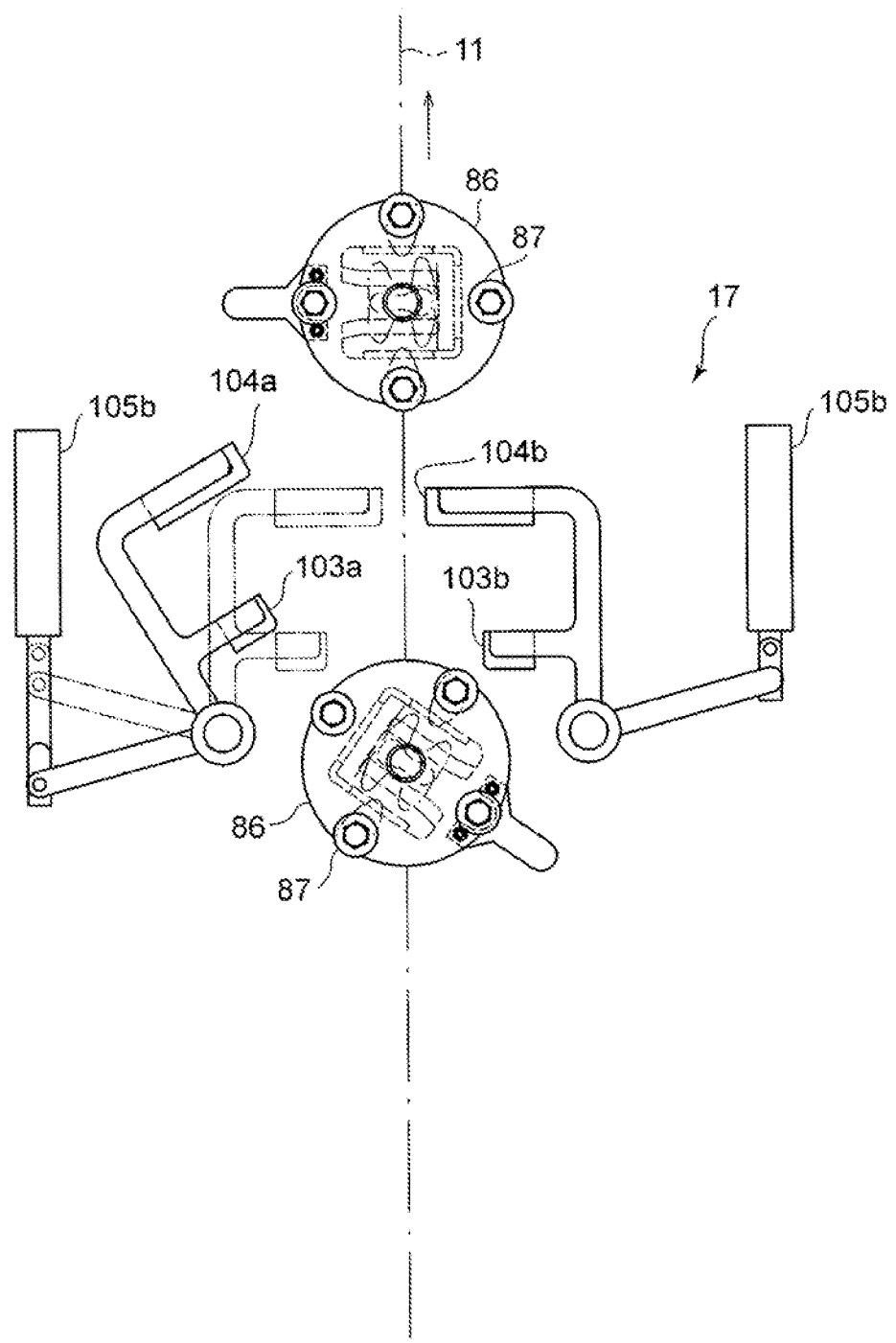
FIG. 34 is a view for explaining the operation of the second clamp rotation device.
Figure 35:
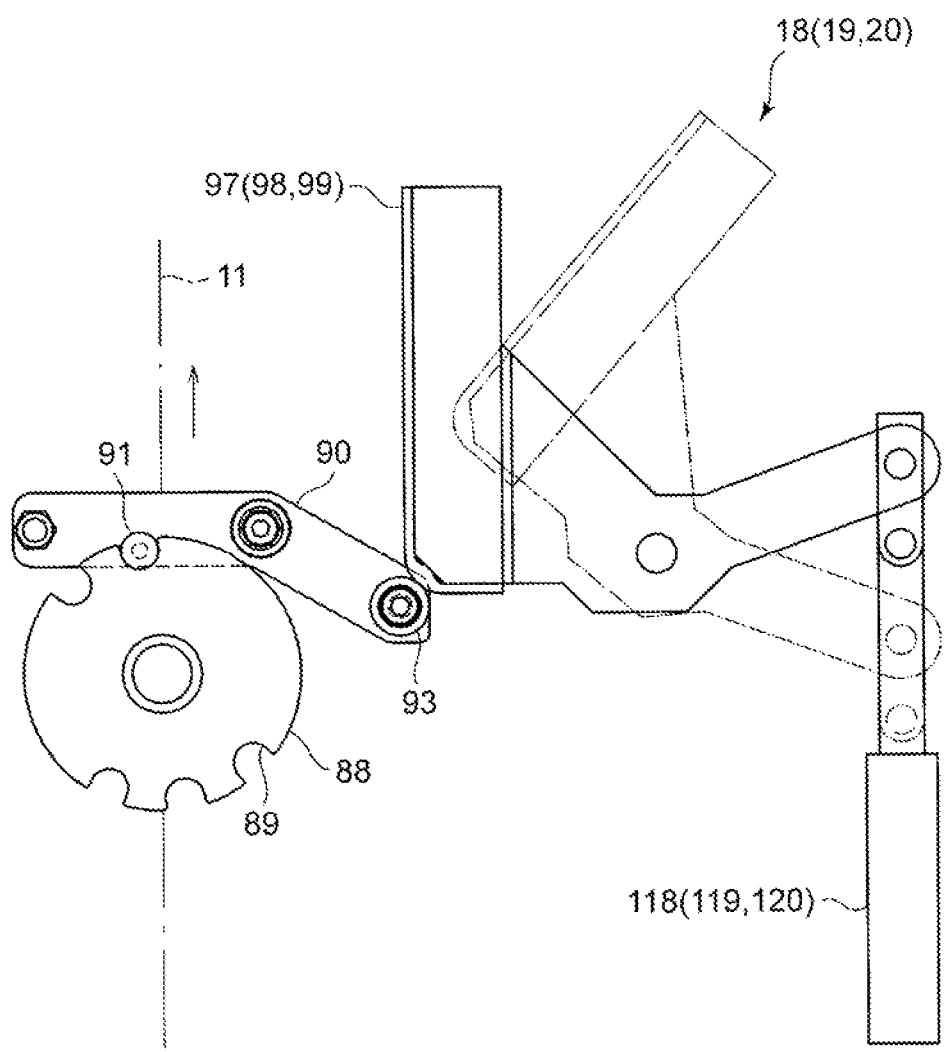
FIG. 35 is a view for explaining the operation of each of third to fifth clamp rotation devices.
Figure 36:
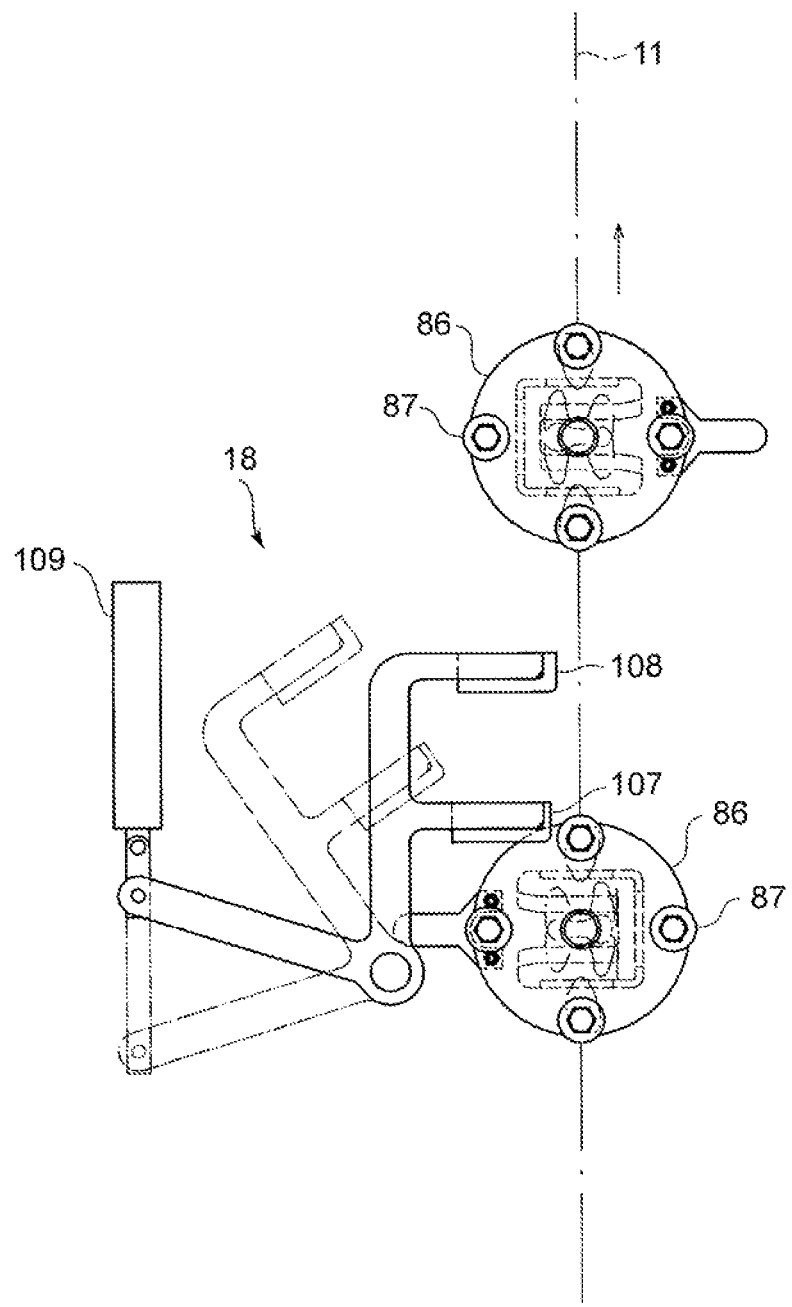
FIG. 36 is a view for explaining the operation of the third clamp rotation device.
Figure 37:
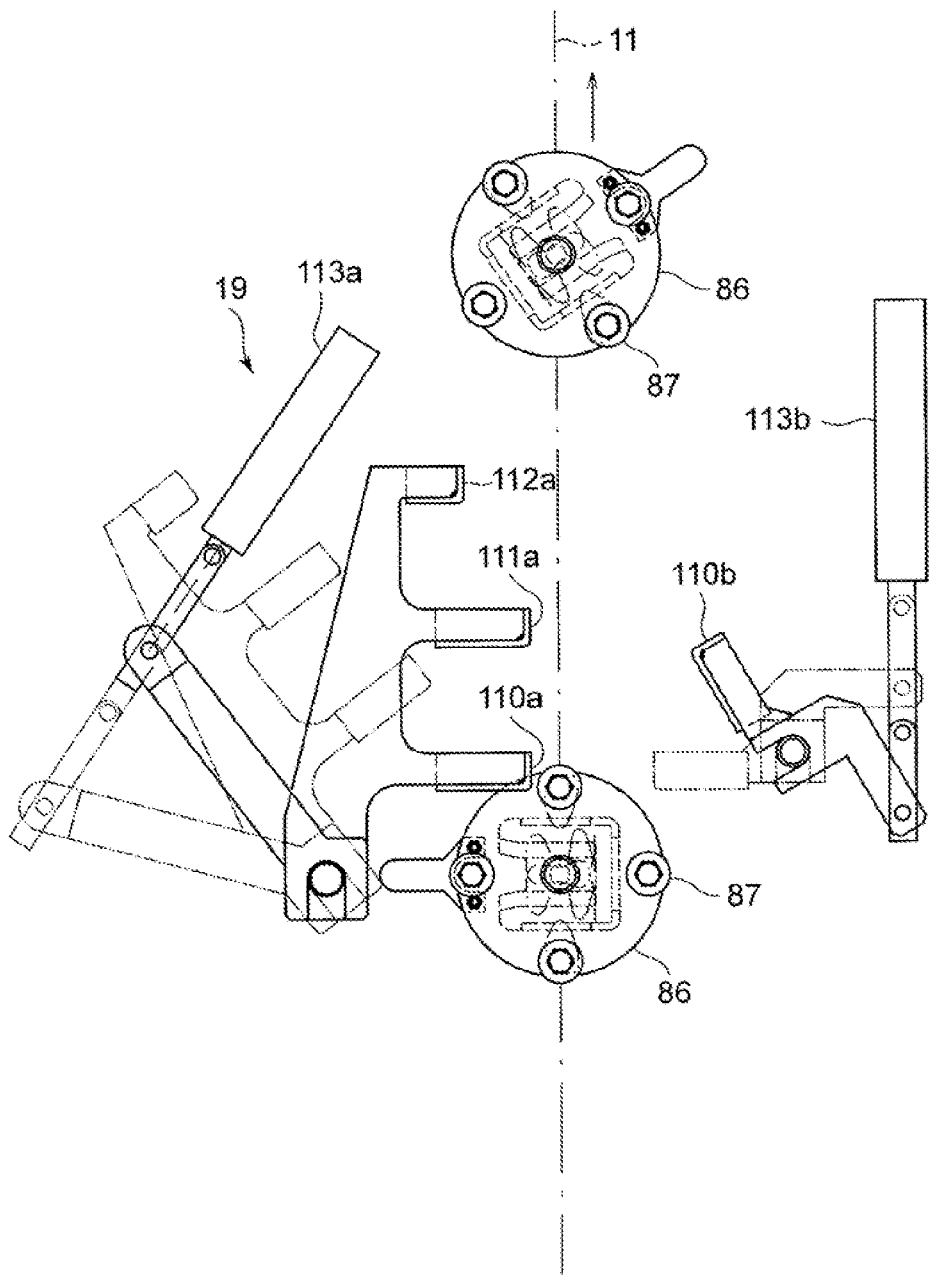
FIG. 37 is a view for explaining the operation of the fourth clamp rotation device.
Figure 38:
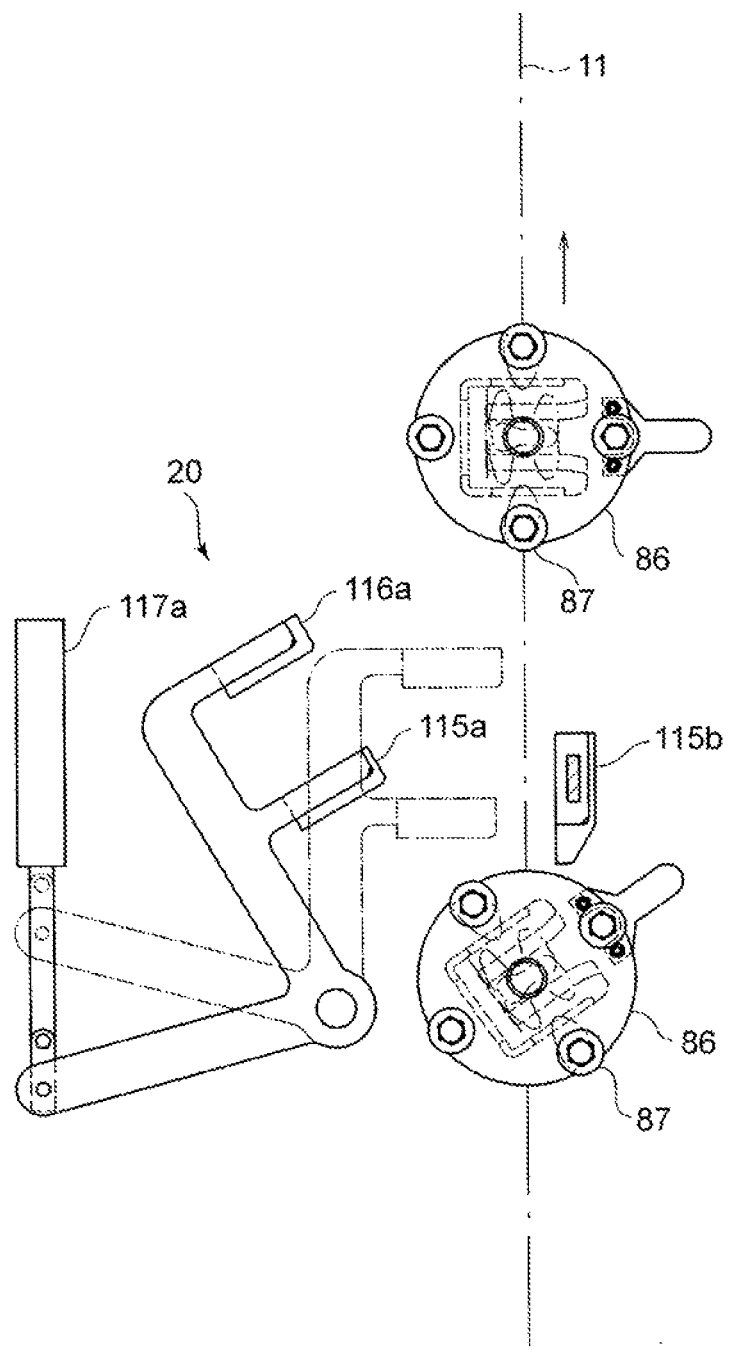
FIG. 38 is a view for explaining the operation of the fifth clamp rotation device.
Figure 39:
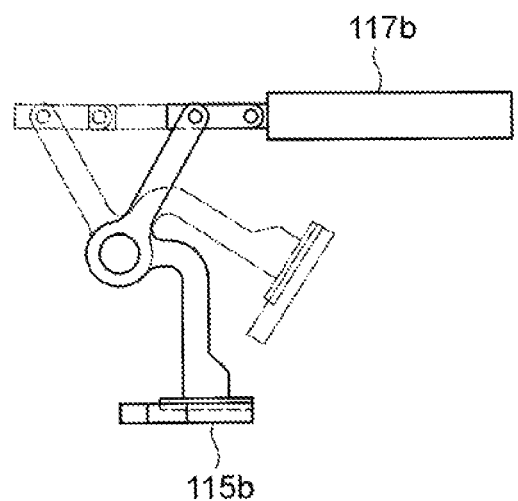
FIG. 39 is a view for explaining the operation of the fifth clamp rotation device.
Figure 40:
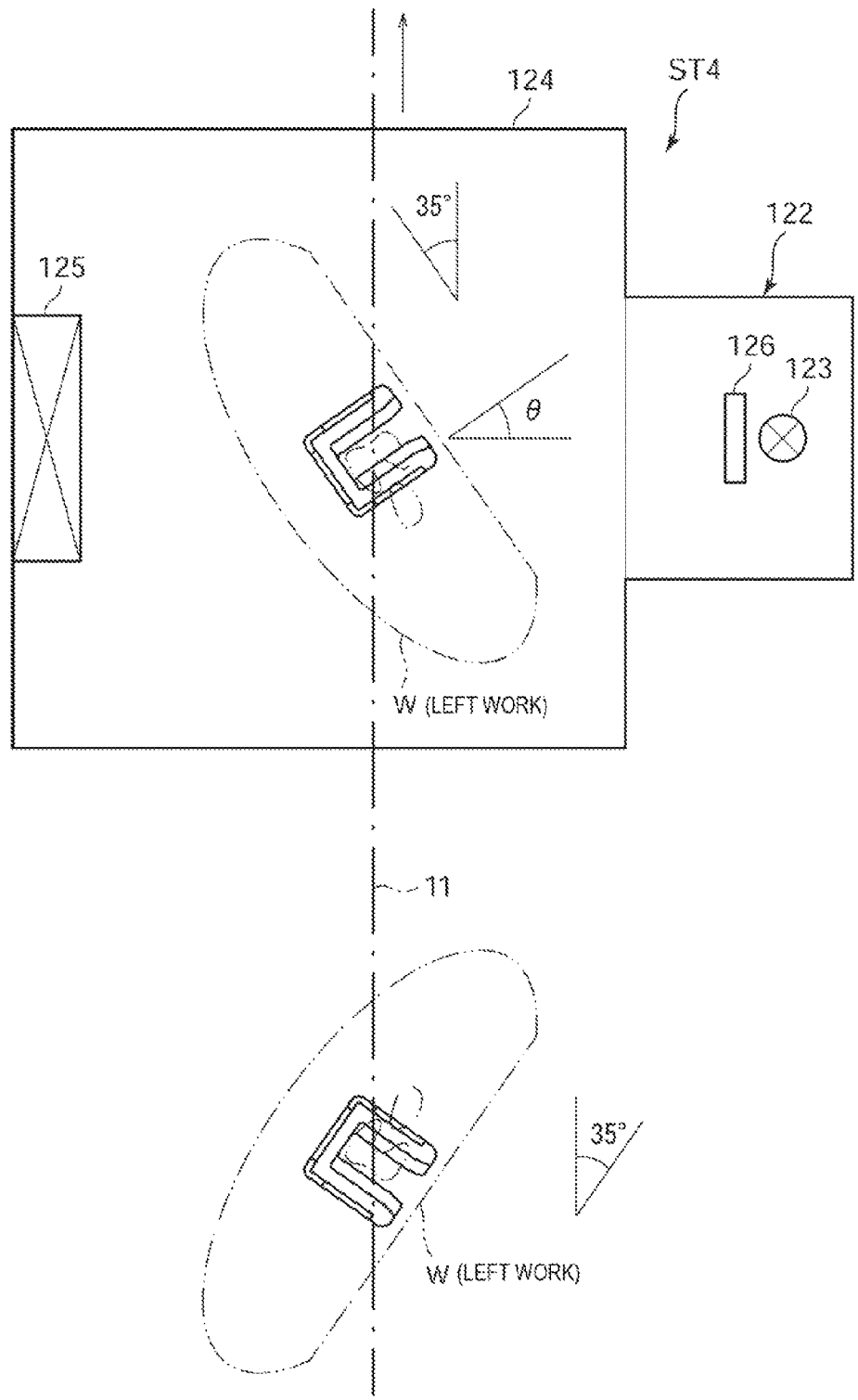
FIG. 40 is a view for explaining the configuration of an X-ray imaging station.
Figure 41:
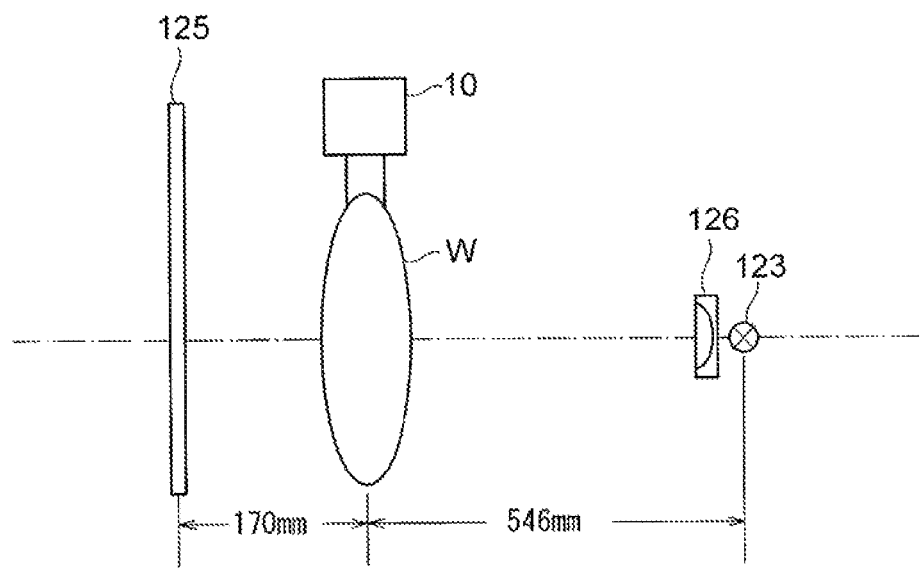
FIG. 41 is a view for explaining the configuration of the X-ray imaging station.
Figure 42:
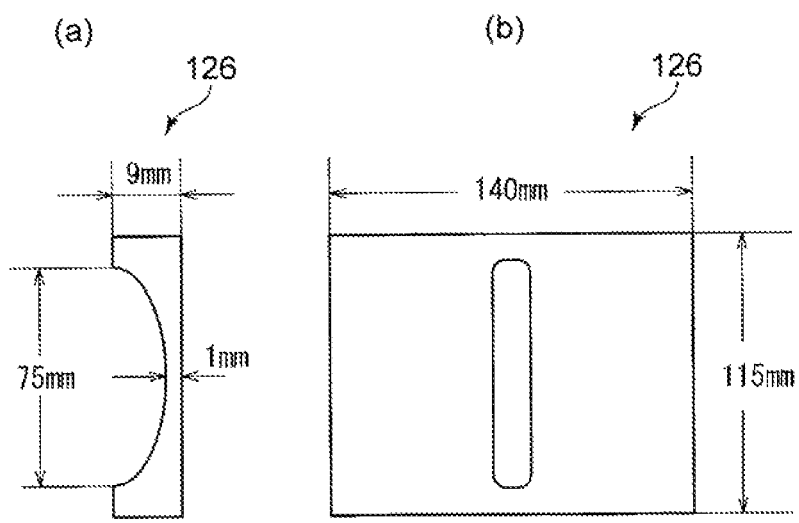
FIG. 42(a) is a side view of a filter.
FIG. 42(b) is a front view of the filter.
Figure 44:
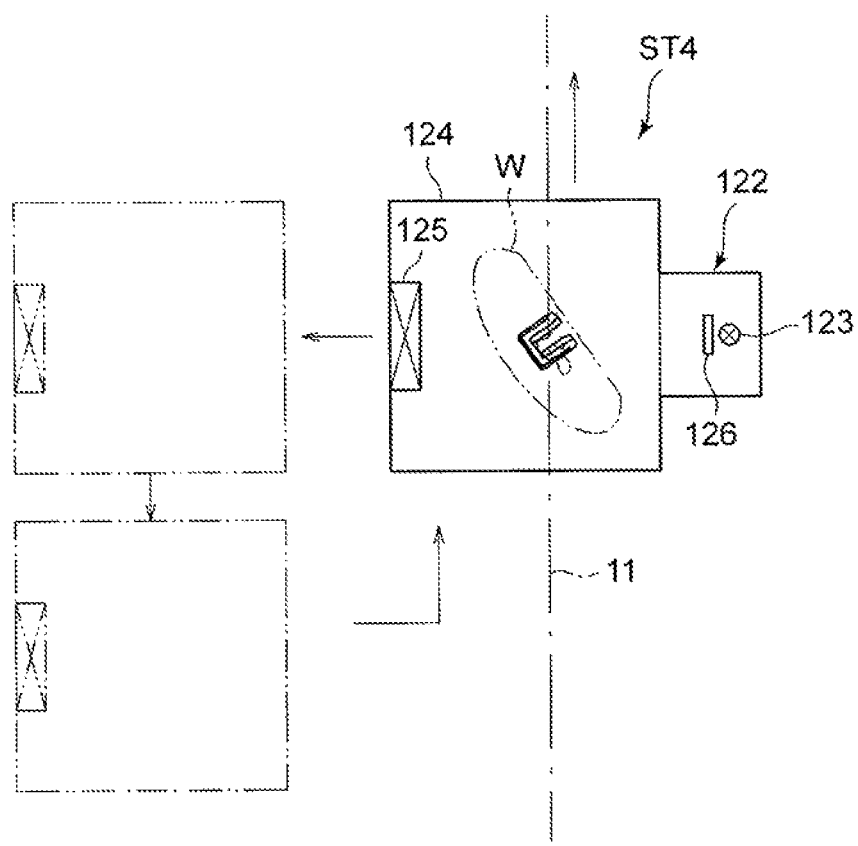
FIG. 44 is a view for explaining the movement of the shielding box.

FIGS. 27 to 29 show the schematic configuration of a clamp device 76 including the clamp 10, and FIG. 30 schematically shows the work W suspended from the clamp 10. In addition, FIGS. 31 to 39 schematically show the first to fifth clamp rotation devices 16, 17, 18, 19, and 20.

The clamp device 76 has a shaft 83 which extends from the clamp 10 in a vertical direction, and the shaft 83 extends through a boss of a carriage part 84 so as to be relatively rotatable. The carriage part 84 is coupled to a chain 85 which extends along the endless track 11, and runs on a rail extending along the endless track 11 with the rotation of the chain 85.

A first disk 86 is fixed to the upper end of the shaft 83, and four rollers 87 are attached to the first disk 86 as cam followers at intervals of 90°. In addition, a second disk 88 is attached to the shaft 83 below the first disk 86. The outer peripheral part of the second disk 88 is formed with semicircular notched parts 89 at predetermined positions.

On the other hand, a rotatable lever 90 is attached to the carriage part 84 in the vicinity of the second disk 88. An engagement pin 91 is attached to the lever 90, and the rotation of the shaft 83 is regulated when the engagement pin 91 is fitted in the notched part 89.

One end of the lever 90 is pulled by a helical tension spring 92, and the engagement between the engagement pin 91 and the notched part 89 is maintained by the tension. In addition, a roller 93 as the cam follower for releasing the engagement between the engagement pin 91 and the notched part 89 is attached to the other end of the lever 90.

FIG. 30 schematically shows the state of the work W immediately after the work W is suspended from the clamp 10. Immediately after the suspension, the work W is disposed such that the cut surface separated from the body is along the endless track 11 irrespective of the left or the right of the work W.

The notched part 89 is provided such that, when the rotation angle of the clamp 10 immediately after the suspension is 0°, the rotation angle of the clamp 10 can be fixed to any of 0°, +35°, −35°, +145°, and +180°. Note that + denotes rotation to the right side relative to the running direction of the clamp 10, while − denotes rotation to the left side.

The first to fifth clamp rotation devices 16, 17, 18, 19, and 20 have cam surfaces 95, 96, 97, 98, and 99 each for releasing the engagement between the engagement pin 91 and the notched part 89. While the roller 93 is in contact with one of the cam surfaces 95, 96, 97, 98, and 99, the lever 90 is rotated against the tension of the helical tension spring 92, and the engagement between the engagement pin 91 and the notched part 89 is released.

The first clamp rotation device 16 has cam surfaces 100a and 100b for rotating the shaft 83 while the engagement is released. The cam surface 100a comes in contact with the roller 87 to thereby rotate the shaft 83 to the left side by 35°, and the cam surface 100b comes in contact with the roller 87 to thereby rotate the shaft 83 to the right side by 35°.

Note that the cam surfaces 100a and 100b are coupled to air cylinders 101a and 101b via link mechanisms, and the control device 21 can cause each of the cam surfaces 100a and 100b to run between an operation position and a wait position by controlling the air cylinders 101a and 101b.

That is, in accordance with the determination result of the left/right determination step S12, it is possible to rotate the shaft to the right side when the work W is the right arm, and rotate the shaft to the left side when the work W is the left arm.

The second clamp rotation device 17 has cam surfaces 103a, 103b, 104a, and 104b for rotating the shaft 83 twice while the engagement is released. The cam surfaces 103a and 104a and the cam surfaces 103b and 104b come in contact with the roller 87 sequentially to thereby set the rotation angle of the shaft 83 to 180°.

Note that the cam surfaces 103a, 103b, 104a, and 104b are also coupled to air cylinders 105a and 105b via the link mechanisms, and the control device 21 can cause each of the cam surfaces 103a, 103b, 104a, and 104b to run between the operation position and the wait position by controlling the air cylinders 105a and 105b.

The third clamp rotation device 18 has cam surfaces 107 and 108 for rotating the shaft 83 by 180° only in the case where it is determined that any error has occurred in the error occurrence determination step S32. That is, the cam surfaces 107 and 108 can set the rotation angle of the shaft 83 to 0°. The cam surfaces 107 and 108 are also coupled to an air cylinder 109 via the link mechanism, and the control device 21 can cause each of the cam surfaces 107 and 108 to run between the operation position and the wait position by controlling the air cylinder 109.

The fourth clamp rotation device 18 has cam surfaces 110a, 111a, 112a, and 110b for rotating the shaft 83 in the case where the error does not occur. The cam surfaces 110a, 111a, 112a, and 110b are also coupled to air cylinders 113a and 113b via the link mechanisms, and the control device 21 can cause each of the cam surfaces 110a, 111a, 112a, and 110b to run between the operation position and the wait position by controlling the air cylinders 113a and 113b. The control device 21 sets the rotation angle of the shaft 83 to −35° when the work W is the left arm and sets the rotation angle of the shaft 83 to +35° when the work W is the right arm by rotating the shaft 83 by using the cam surfaces 110a, 111a, 112a, and 110b.

The fifth clamp rotation device 20 has cam surfaces 115a, 116a, and 115b for rotating the shaft 83 in the case where the error does not occur. The cam surfaces 115a, 116a, and 115b are also coupled to air cylinders 117a and 117b via the link mechanisms, and the control device 21 can cause each of the cam surfaces 115a, 116a, and 115b to run between the operation position and the wait position by controlling the air cylinders 117a and 117b. The control device 21 sets the rotation angle of the shaft 83 to 0° by rotating the shaft 83 by using the cam surfaces 115a, 116a, and 115b.

Note that the cam surfaces 97, 98, and 99 each for releasing the engagement between the engagement pin 91 and the notched part 89 are also coupled to air cylinders 118, 119, and 120 via the link mechanisms, and the control device 21 controls the air cylinders 118, 119, and 120 on an as needed basis to release the engagement.

[X-Ray Imaging Step/X-Ray Imaging Station]

FIGS. 40 to 45 schematically show the configuration of the X-ray imaging station ST4. The X-ray imaging station ST4 has an X-ray irradiation device 122, and the X-ray irradiation device 122 has an X-ray source 123. In addition, the X-ray imaging station ST4 has a shielding box 124 which accommodates the work W as an imaging target of an X-ray image, and a line sensor 125 as an X-ray detector is disposed in the shielding box 124. That is, the X-ray imaging station ST4 is an X-ray image capturing device of bone-in meat.

The X-ray source 123 and the line sensor 125 are spaced apart from each other in a horizontal direction orthogonal to the endless track 11. Consequently, an X-ray is applied to the suspended work W at an incident angle θ of about 35° relative to the cut surface separated from the body of the work W.

Note that the rotation angle of the work W, i.e., the rotation angle of the clamp 10 is most preferably 35° to the left side in the case of the left arm and 35° to the right side in the case of the right arm, but the rotation angle thereof may appropriately be more than 30° and less than 45°.

In addition, the X-ray irradiation device 122 further has an X-ray filter 126 placed in the vicinity of the X-ray source 123. The X-ray filter 126 absorbs part of the X-ray, and gives an appropriate intensity distribution to the X-ray applied to the work W.

Specifically, the X-ray filter 126 has a concave lens shape in which the center is depressed. The position of the thinnest part of the X-ray filter 126 is set to correspond to the position of the X-ray source 123 and the position of the thickest part of the work W in the vertical direction.

Note that the shielding box 124 can be brought close to or moved away from the endless track 11 by a motor 128 in the horizontal direction orthogonal to the endless track 11, and the shielding box 124 can be moved by a motor 129 in a direction along the endless track 11. The control device 21 can dispose the work W in the shielding box 124 without stopping the conveyance of the work W by controlling the motors 128 and 129. Consequently, it is possible to capture the X-ray image of the work W without stopping the conveyance of the work W.

Figure 45:
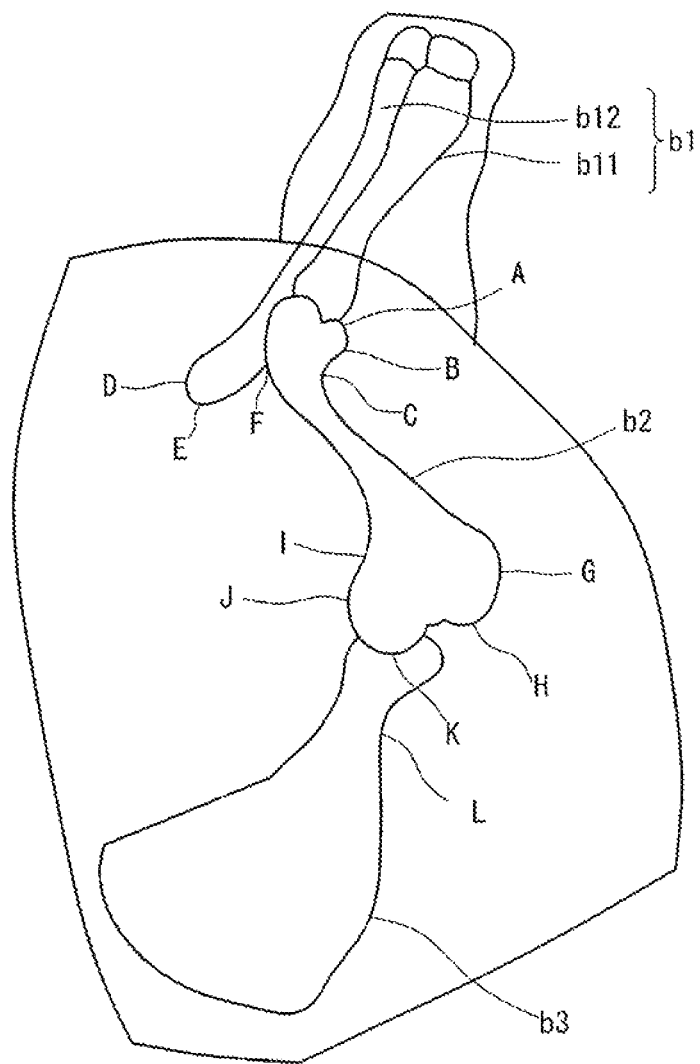
FIG. 45 is a view showing target positions A to L in the work of which coordinates are to be determined on the basis of an X-ray image.

When the X-ray image of the work W is picked up in the X-ray imaging station ST4, the control device 21 analyzes the X-ray image and, as shown in FIGS. 45 and 26(b), determines coordinates of a plurality of target positions A to L required for incision making. Note that the forearm bone b1 is formed of a radius b11 and a ulna b12.

[Second Forearm-Bone Incision Making Step/Round Blade Cutter Device]

Figure 46:
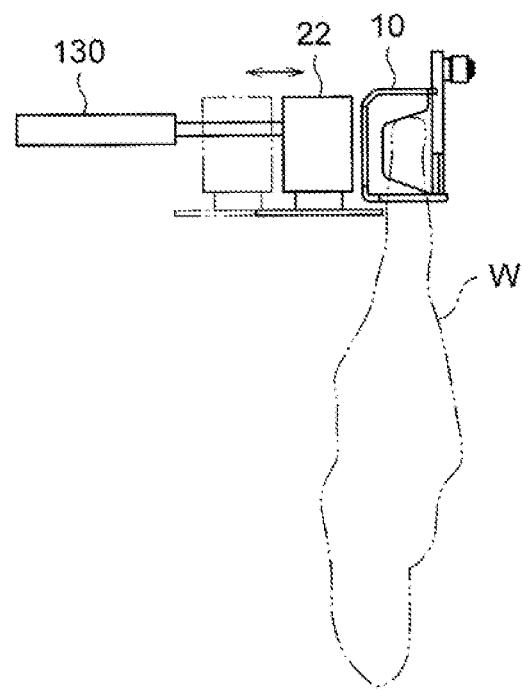
FIG. 46 is a view schematically showing a round blade cutter device which performs a second forearm-bone incision making step.
Figure 47:
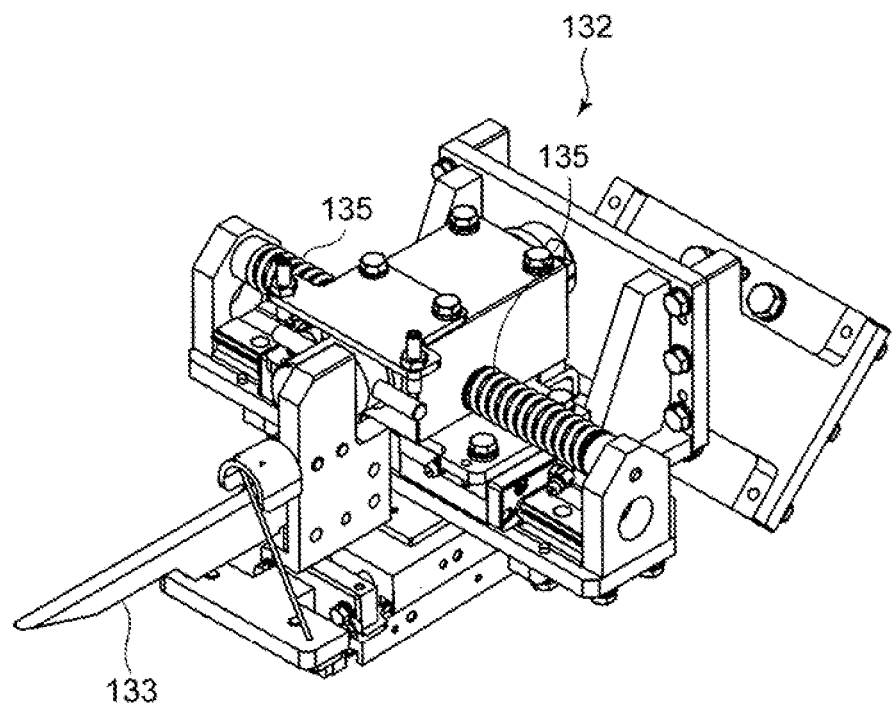
FIG. 47 is a perspective view schematically showing a cutter tool of a first incision making station.
Figure 48:
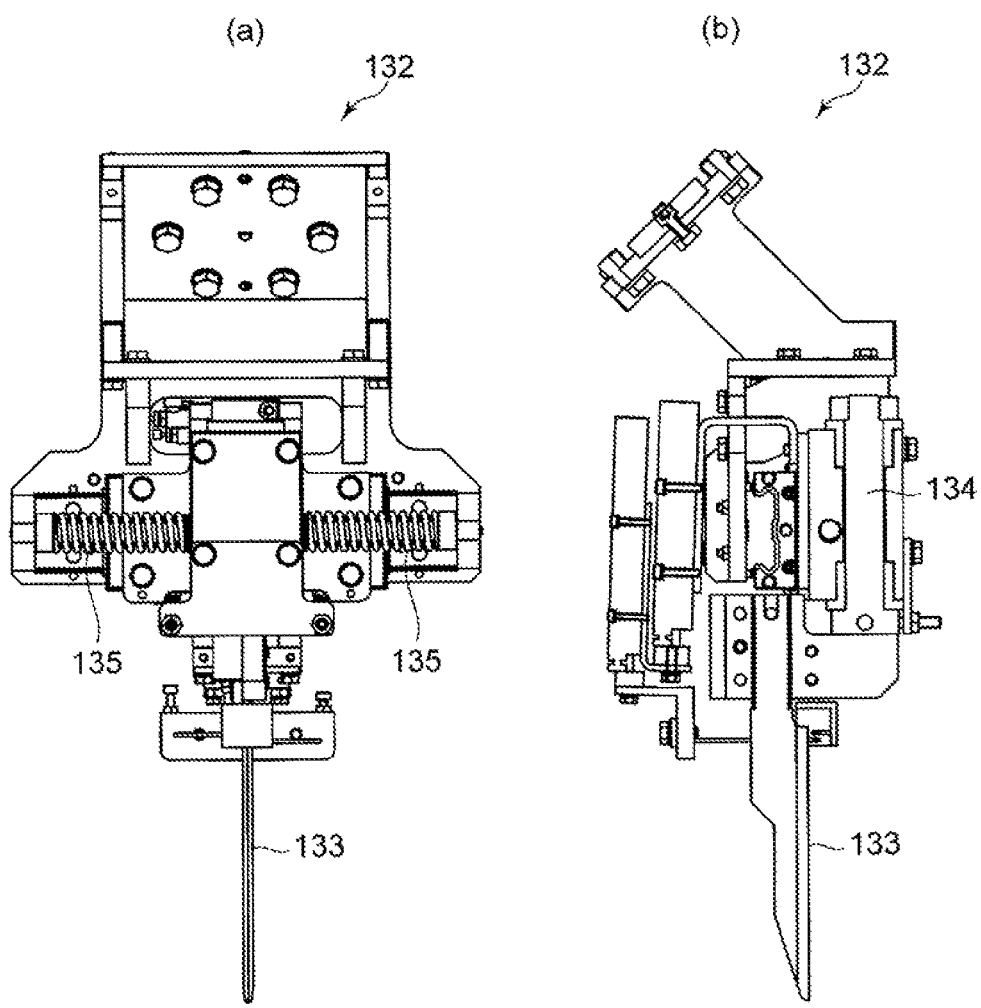
FIG. 48(a) is a plan view of the cutter tool.
FIG. 48(b) is a cross-sectional view of the cutter tool.
Figure 49:
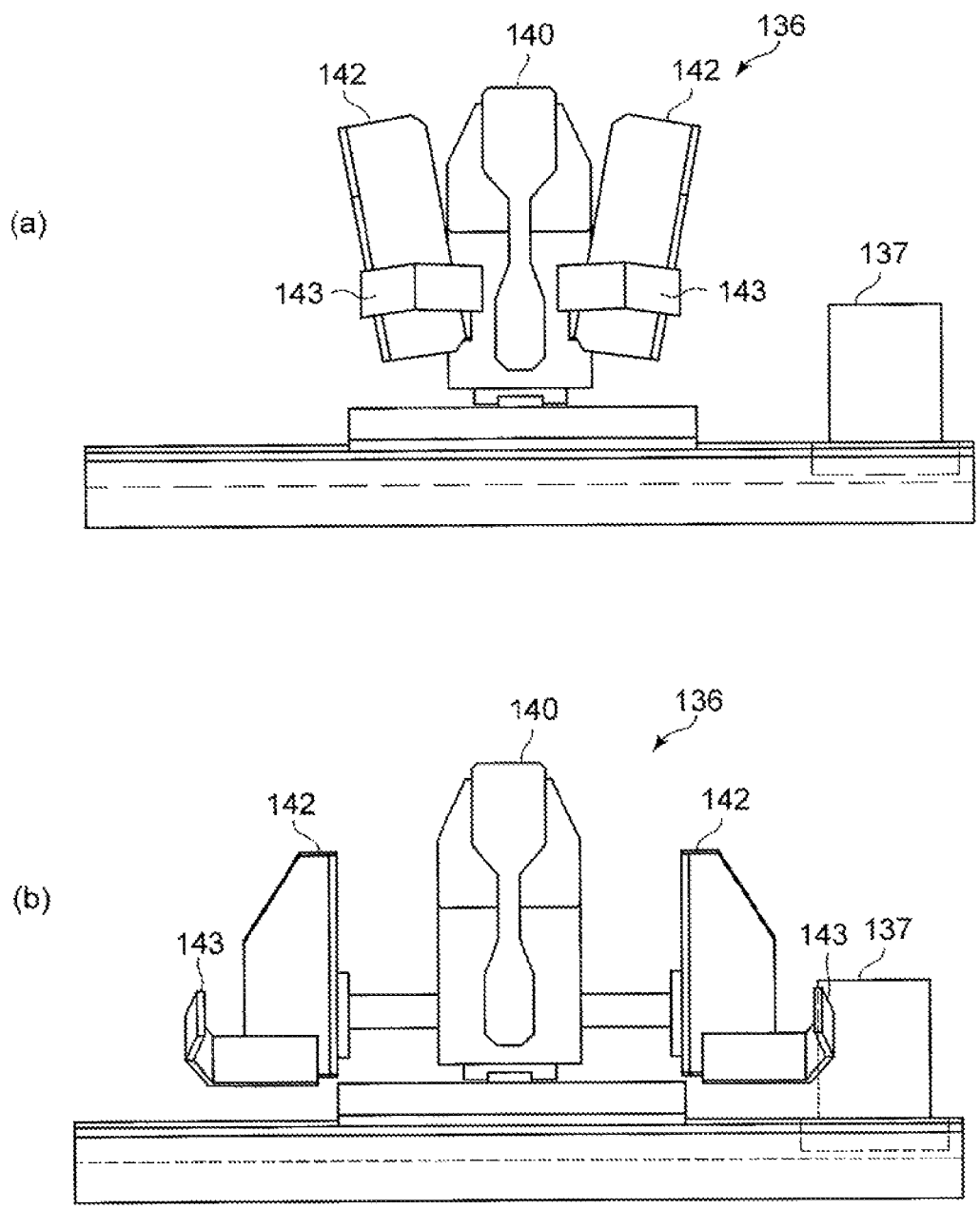
Figure 50:
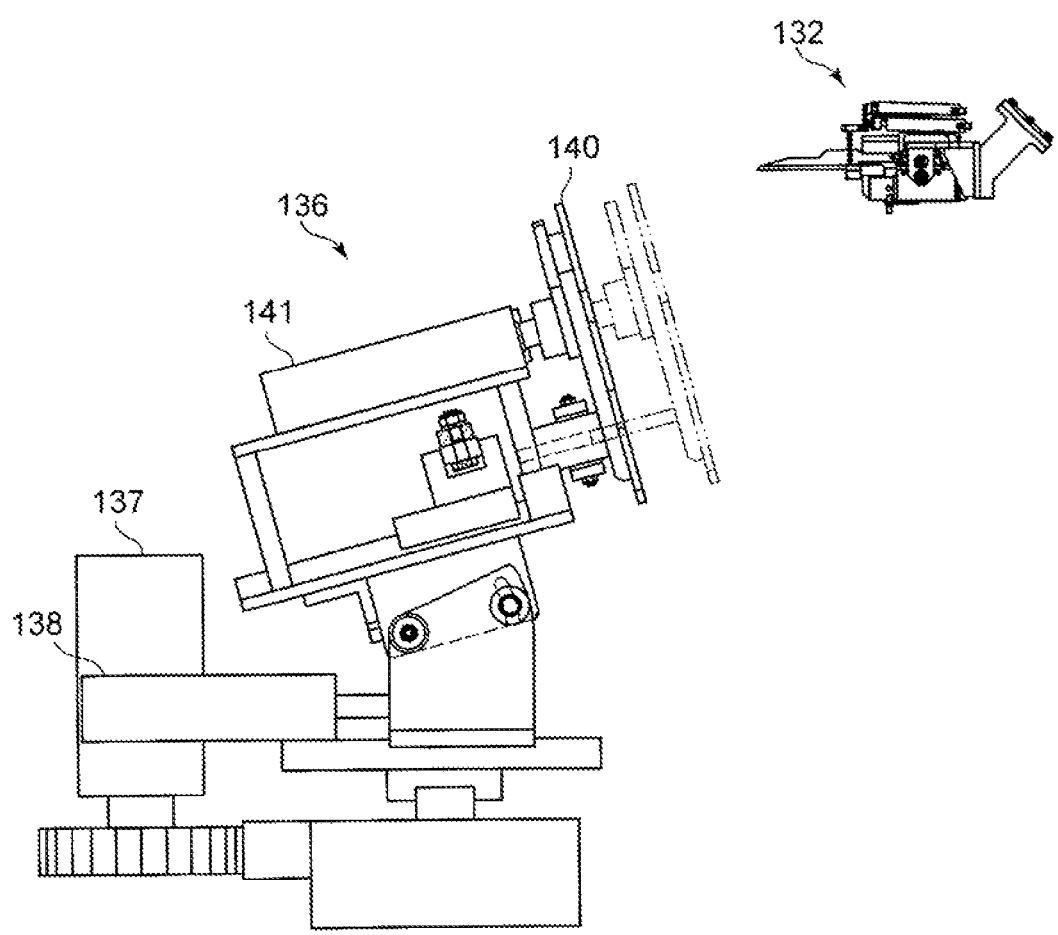
FIG. 50 is a side view schematically showing a part of the support device.
Figure 51:
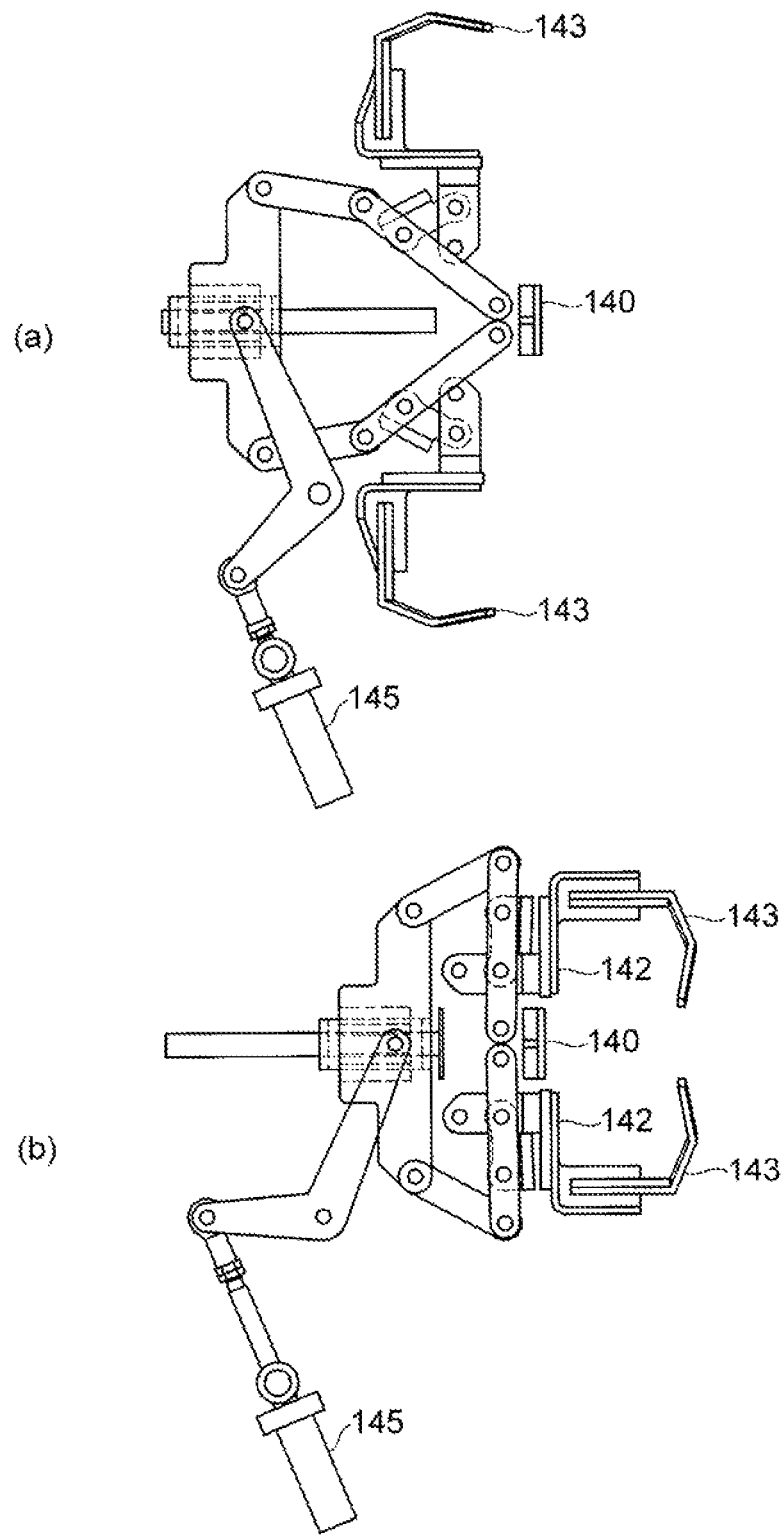
FIGS. 51(a) and 51(b) are plan views schematically showing a part of the support device.
Figure 52:
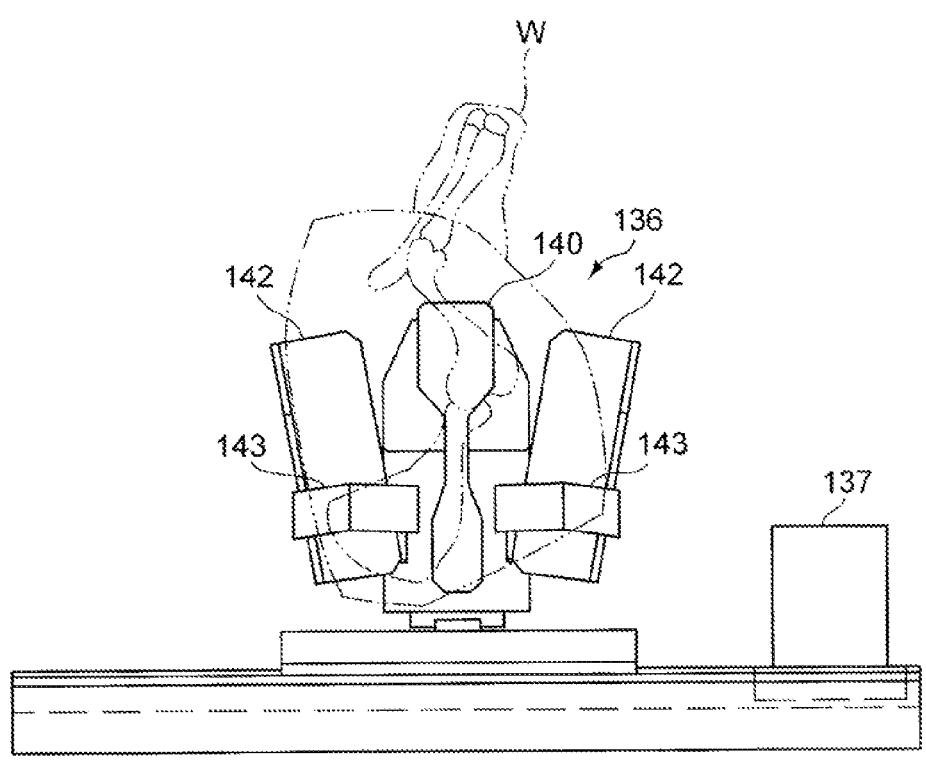
FIG. 52 is a front view schematically showing the support device in the operation state together with the work.
Figure 53:
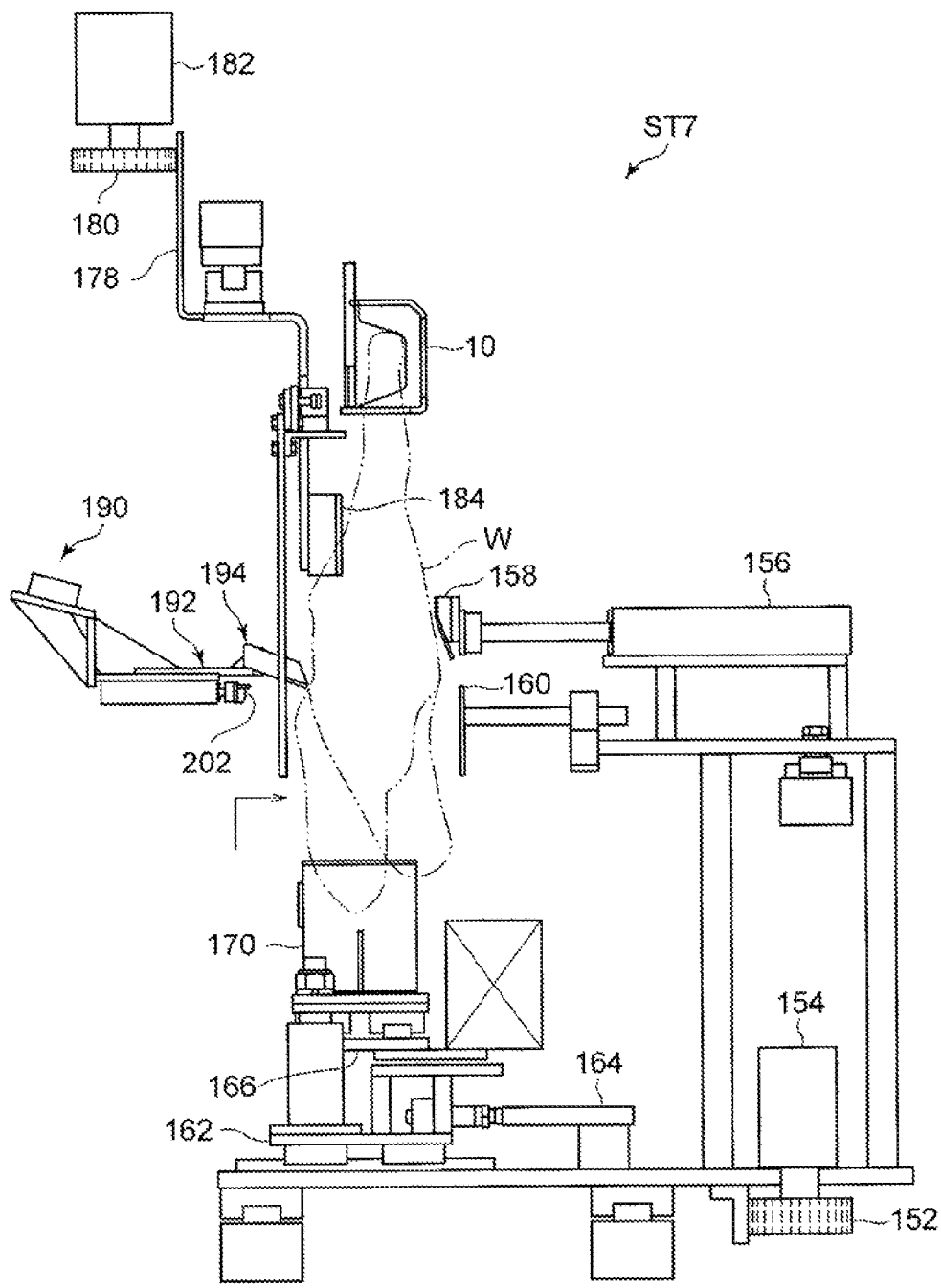
FIG. 53 is a side view schematically showing a shoulder blade removal station.
Figure 54:
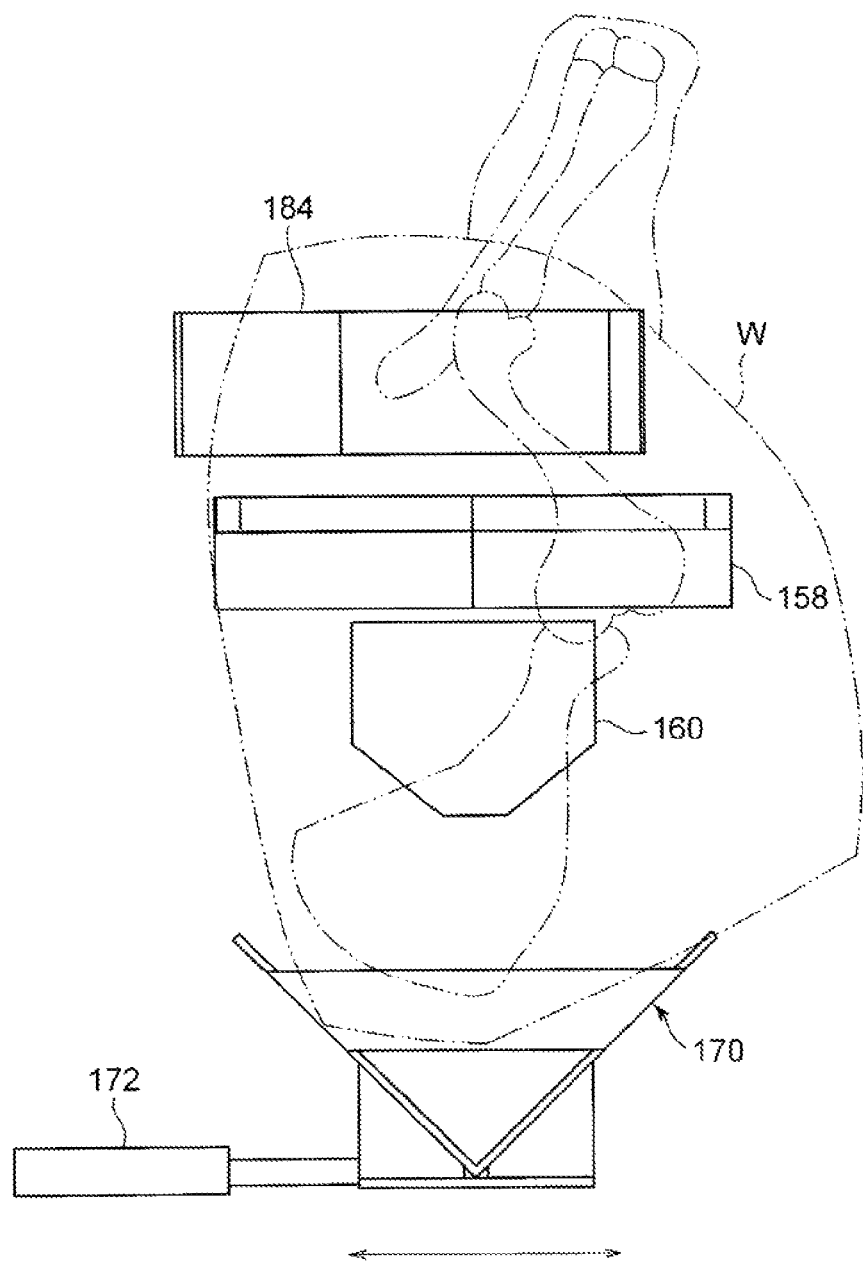
FIG. 54 is a front view schematically showing an upper side support member, a lower side support member, a bottom holder, and a guide plate together with the work, and is also a view for explaining the movement of the bottom holder.
Figure 56:
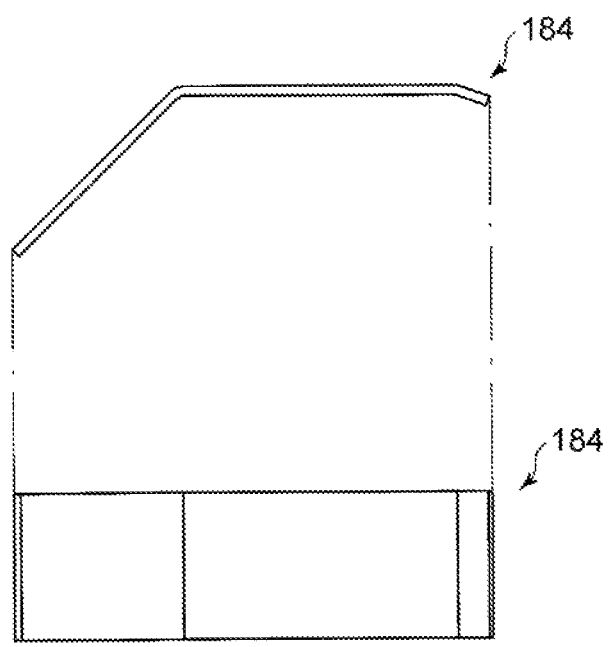
FIG. 56 includes a top view and a front view of the guide plate.
Figure 57:
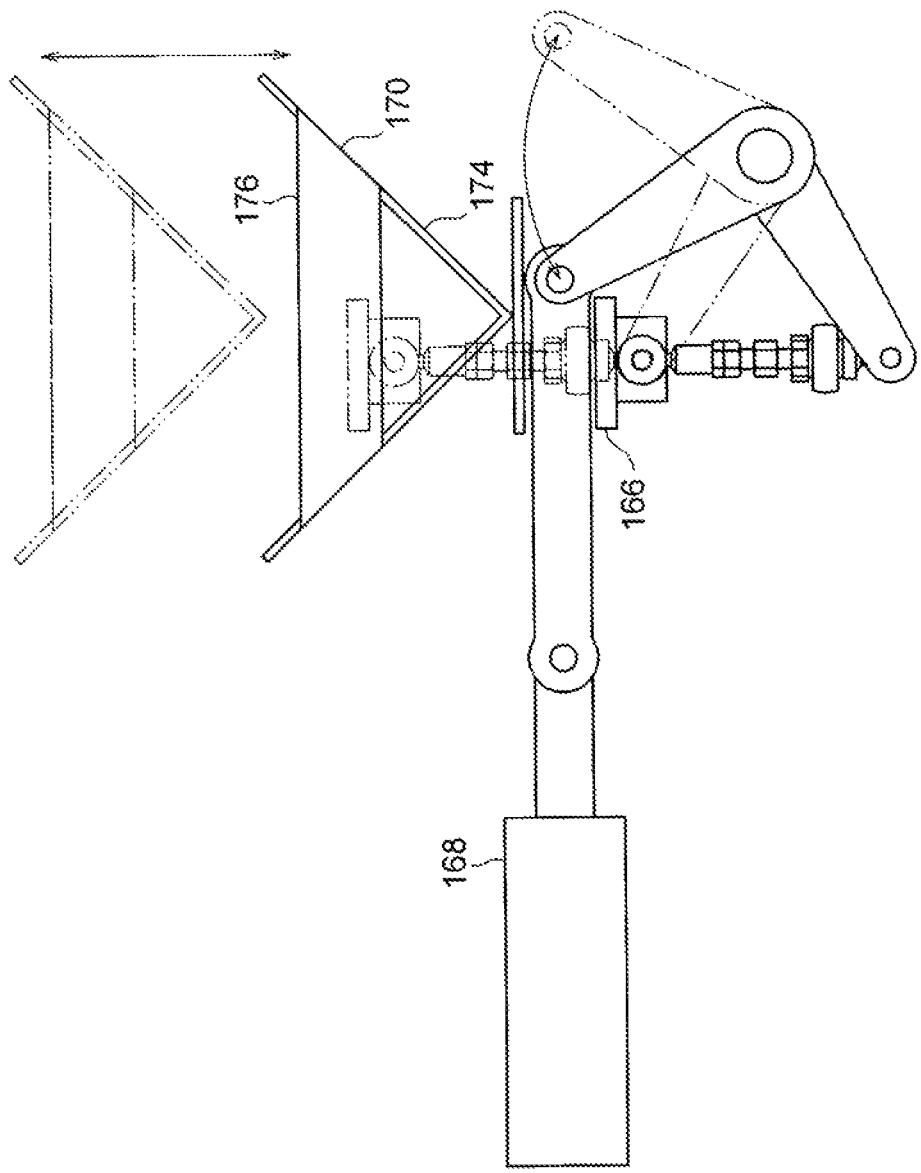
FIG. 57 is a view for explaining ascent and descent of the bottom holder.
Figure 58:
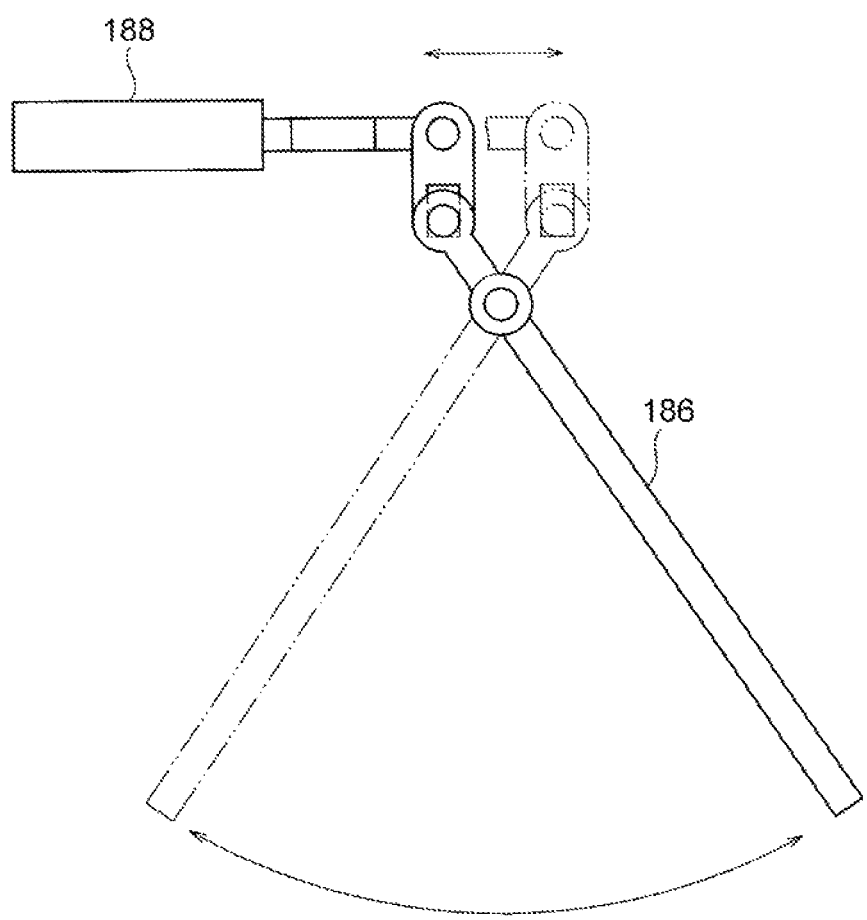
FIG. 58 is a view for explaining a swing of a wiper.
Figure 59:
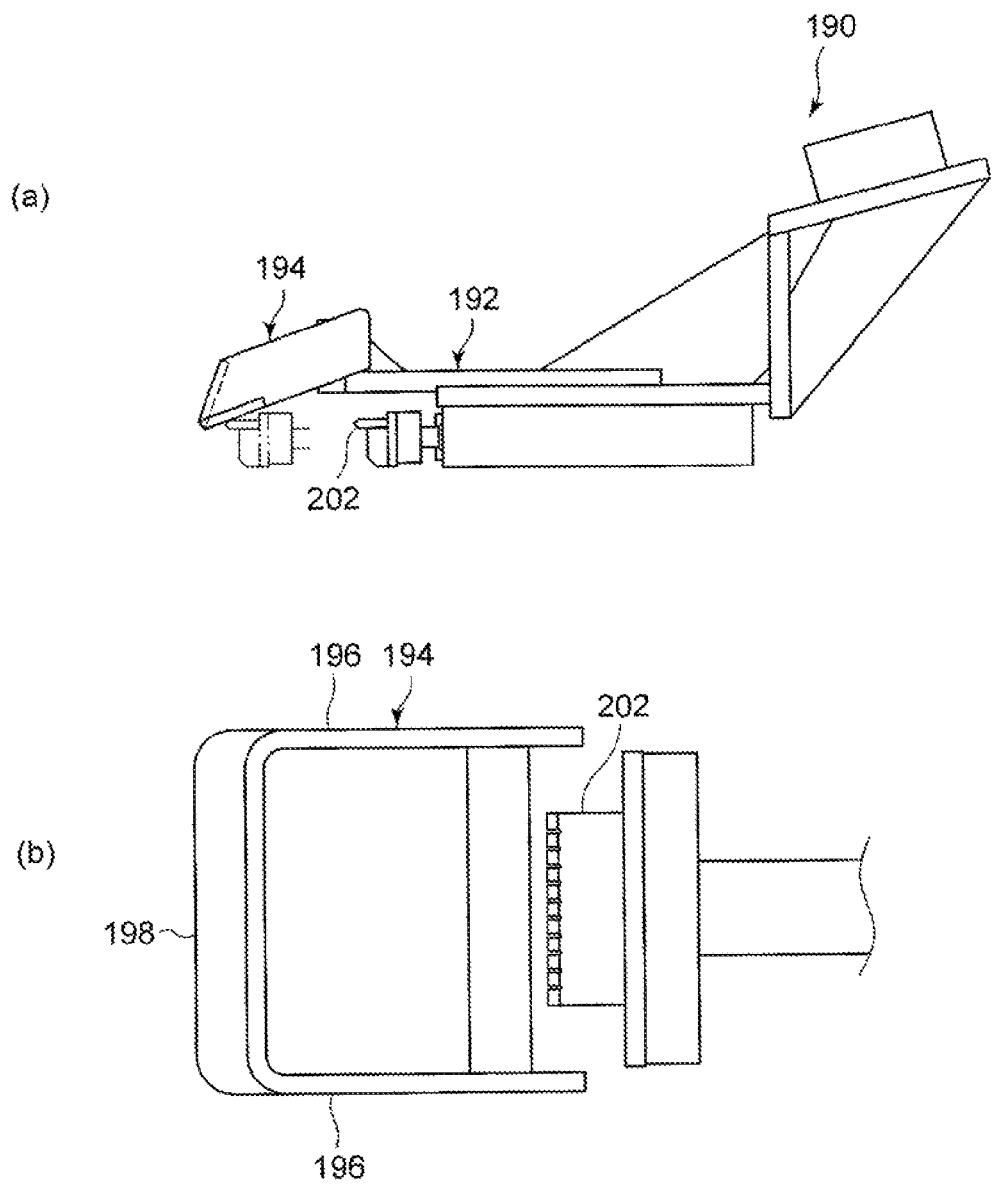
FIG. 59(a) is a side view schematically showing a chuck unit.
FIG. 59(b) is a plan view schematically showing a grip member and a lock member of the chuck unit.
Figure 60:
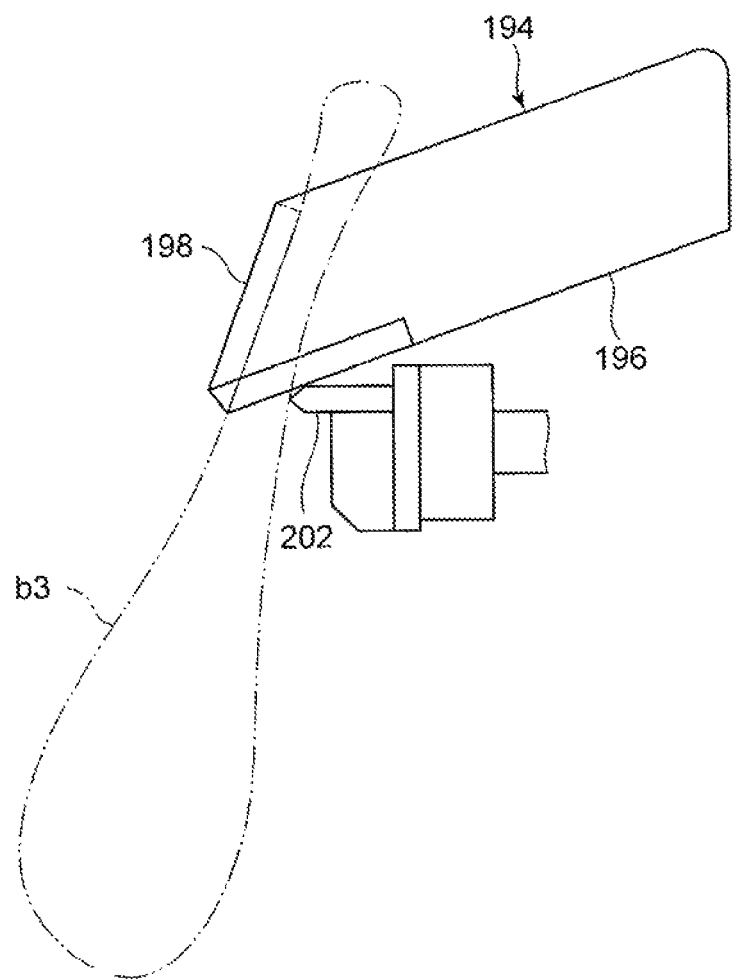
FIG. 60 is a view for explaining a state in which the grip member and the lock member grip the shoulder blade.

FIG. 46 schematically shows the configuration of the round blade cutter device 22. The round blade cutter device 22 is coupled to an air cylinder 130, and can elastically come in contact with the work W. The round blade cutter device 22 performs incision making on the back side of the forearm bone b1 as the second forearm-bone incision making step S22.

[First and Second Incision Making Steps/First and Second Incision Making Stations]

FIGS. 47 to 52 schematically show the configuration of the first incision making station ST5. Note that the configuration of the second incision making station ST6 is the same as the configuration of the first incision making station ST5, and hence the description thereof will be omitted.

The first incision making station ST5 has a cutter tool 132 as an attachment attached to the robot arm 40. A cutter 133 of the cutter tool 132 is swingably supported by a swing shaft 134. The swing shaft 134 is positioned in front of the cutter 133 in the direction of cutting of the cutter 133.

The swing shaft 134 is slidable in a direction orthogonal to itself, and compression coil springs 135 which bias the swing shaft 134 toward a neutral position are provided on both sides of the swing shaft 134. Consequently, the cutter 133 is swingable and elastically slidable in a direction intersecting the cutting direction.

In addition, the first incision making station ST5 has a support device 136 which elastically supports the work W. The support device 136 can be moved by a motor 137 along the endless track 11, and can be advanced or retracted by an air cylinder 138 in the horizontal direction orthogonal to the endless track 11. Consequently, the support device 136 can be moved in synchronization with the work W which is being conveyed, and the robot arm 40 can perform incision making on the work W which is being conveyed by using the cutter tool 132.

More specifically, the support device 136 has a center plate 140, and the center plate 140 is elastically supported by an air cylinder 141. Consequently, a difference in the size of the work W is absorbed by the pressure of air, and the work W is properly supported irrespective of the size of the work W.

In addition, the center plate 140 elastically supports the back surface of the work W in a direction orthogonal to the endless track 11 while the robot arm 40 performs incision making on the basis of the target positions A to L. The course of the cutter 133 is precisely determined on the basis of the target positions A to L, but the target positions A to L include errors in the direction orthogonal to the endless track 11 (depth direction). The center plate 140 elastically supports the work W in the depth direction, and the cutter 133 is thereby prevented from being stuck into a bone even when the cutter excessively advances.

In addition, the support device 136 has a pair of side plates 142 disposed on both sides of the center plate 140. A pair of swing arms 143 which pinch and support the lower side of the work W are attached to the side plates 142. The swing arms 143 pinch the work W, and the swing of the work W in the direction of conveyance of the work W is thereby prevented while the robot arm 40 performs incision making.

Particularly, the shoulder blade b3 is present in the lower side of the work W, and hence the swing arms 143 pinch the part around the shoulder blade b3 of the work W, and the swing of the work W is thereby prevented reliably. At this point, the positions of the swing arms 143 in the direction along the endless track 11 can be set to appropriate positions according to the left or the right of the work W.

Further, the swing arm 143 has a substantially L-shaped cross section, and can hold the robot arm 40 side of the work W. Consequently, the swing arms 143 also prevent the swing of the work W in a direction intersecting the endless track 11 in cooperation with the center plate 140.

Note that the swing arms 143 are coupled to an air cylinder 145 via the link mechanisms, and it is possible to cause each of the swing arms 143 to run between the operation position and the wait position by controlling the air cylinder 145.

Thus, with the execution of the first incision making step S24 by the first incision making station ST5, incision making is performed as indicated by a line L3 in FIG. 26(c).

In addition, with the execution of the second incision making step S26 by the second incision making station ST6, incision making is performed as indicated by a line L4 in FIG. 26(d).

[Shoulder Blade Removal Step/Shoulder Blade Removal Station]

FIGS. 53 to 60 show the schematic configuration of the shoulder blade removal station ST7. The shoulder blade removal station ST7 is a shoulder blade removal device of bone-in meat.

The shoulder blade removal station ST7 has a stage 150 which is movable along the endless track 11, and the stage 150 is driven by an endless belt 152 fixed to the stage 150 and a motor 154 which rotates the endless belt 152. The control device 21 controls the motor 154 to move the stage 150 in synchronization with the clamp 10.

An air cylinder 156 is fixed onto the stage 150, and an upper side support member 158 is fixed to the tip of the air cylinder 156. The upper side support member 158 comes in contact with the part of the work W immediately above the shoulder blade b3 in the horizontal direction orthogonal to the endless track 11, and elastically supports the work W. In addition, on the stage 150, a lower side support member 160 is provided below the upper side support member 158. The lower side support member 160 comes in contact with the part of the work W in the vicinity of the upper end of the shoulder blade b3 in the horizontal direction orthogonal to the endless track 11, and elastically supports the work W.

Further, on the stage 150, there is provided a horizontally movable stage 162 which is movable in the horizontal direction orthogonal to the endless track 11, and the horizontally movable stage 162 can be moved by an air cylinder 164. On the horizontally movable stage 162, there is provided a lift stage 166 which is movable in a vertical direction, and the lift stage 166 is coupled to an air cylinder 168 via the link mechanism. Consequently, it is possible to move the lift stage 166 vertically by controlling the air cylinder 168.

On the lift stage 166, there is provided a bottom holder 170 which is movable in the horizontal direction parallel with the endless track 11. The bottom holder 170 is coupled to an air cylinder 172, and it is possible to move the bottom holder 170 by controlling the air cylinder 172. The control device 21 controls the air cylinder 172 according to the left or the right of the work W to dispose the bottom holder 170 at the optimum position according to the left or the right of the work W.

The bottom holder 170 is formed of a V-shaped bottom plate 174 and a lateral plate 176 attached to a side edge 174 of the bottom plate 174 on the side of the robot arm 40. The bottom holder 170 is lifted upward from below the work W so as to accommodate the lower side of the work W, and is moved toward the upper side support member 158 after having accommodated the lower side of the work W. At this point, the lower side of the work W is pushed by the lateral plate 176. With this, the work W is bent in the vicinity of the upper end of the shoulder blade 3b, and the upper end of the shoulder blade b3 protrudes toward the robot arm 40.

Note that the upper side support member 158 has a recessed portion at a central part in a direction following the endless track 11 so that the central part of the upper side support member 158 is depressed away from the endless track 11, and the lower half of the upper side support member 158 is tilted away from the endless track 11 in a downward direction. The tilt of the lower half assists bending of the work W in the vicinity of the upper end of the shoulder blade 3b.

In addition, the shoulder blade removal station ST7 has a bracket 178 which is movable in the horizontal direction along the endless track 11, and an endless belt 180 is fixed to the bracket 178. The endless belt 180 is rotated by a motor 182, and the bracket 178 can be moved along the endless track 11 with the rotation of the endless belt 180. The control device 21 moves the bracket 178 in synchronization with the clamp 10 by controlling the motor 182.

A guide plate 184 is attached to the bracket 178, and the guide plate 184 comes in contact with the work W from a side opposite to the upper side support member 158 in the direction parallel with the endless track 11.

In addition, a wiper 186 is swingably attached to the bracket 178. The wiper 186 is coupled to an air cylinder 188 via the link mechanism, and it is possible to swing the wiper 186 by controlling the air cylinder 188. The control device 21 swings the wiper 186 first to sweep away the ribs w1 from above the shoulder blade b3 in the shoulder blade removal step S27.

On the other hand, the shoulder blade removal station ST7 has a chuck unit 190 as an attachment of the robot arm 40. The chuck unit 190 has a base member 192 attached to the robot arm 40, and a grip member 194 is attached to the tip of the base member 192. The grip member 194 is formed of two longitudinal plate parts 196 fixed to the base member 192 and a lateral plate part 198 continuous with the tips of the longitudinal plate parts 196, and has a U-shaped planar shape. One side edge on the tip side of the longitudinal plate part 196 and one side edge of the lateral plate part 198 are formed as blades.

In addition, the chuck unit 190 has an air cylinder 200 fixed to the base member 192, and a lock member 202 is attached to the tip of the air cylinder 180. The lock member 202 can be advanced or retracted toward or away from the lateral plate part 198, and the control device 21 causes the lateral plate part 198 and and the lock member 202 to grip the shoulder blade b3 therebetween by controlling the air cylinder 200. Note that a plurality of slits are formed in the tip of the lock member 202 to prevent sliding.

According to the chuck unit 190, the blades are formed in the grip member 194, and hence it is possible to reliably grip the shoulder blade b3 and remove the shoulder blade b3 as shown in FIG. 26(e).

[Third Forearm-Bone Incision Making Step/Forearm-Bone Incision Making Station]

Figure 61:
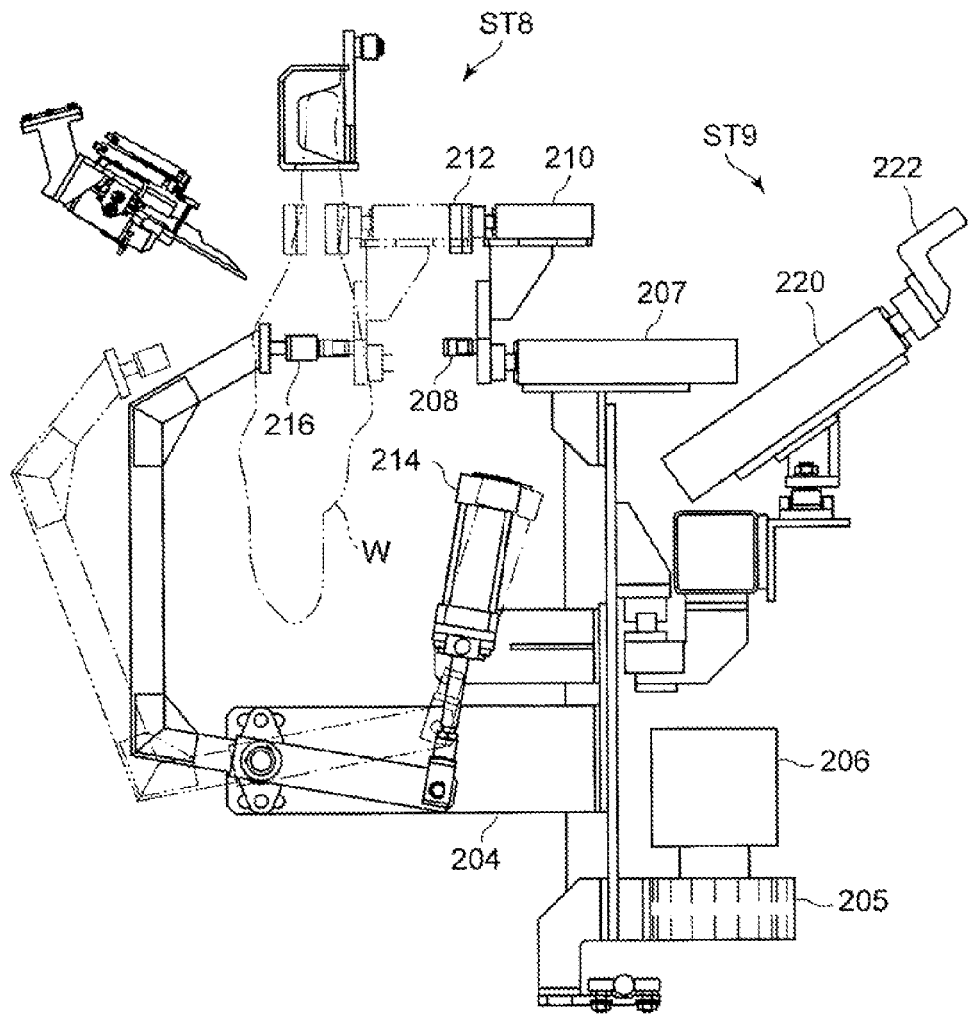
FIG. 61 is a side view schematically showing a third forearm-bone incision making station and a work discharge station.
Figure 62:
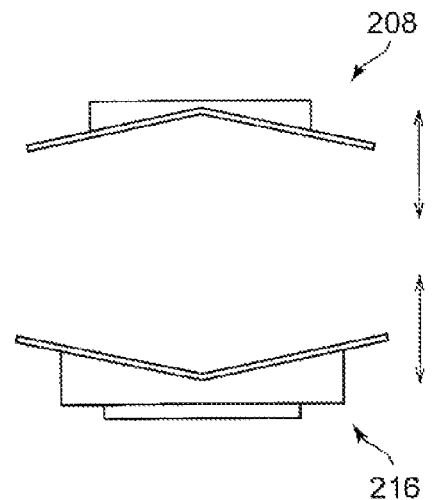
FIG. 62 is a plan view showing a lower side support member and a holding member.
Figure 63:
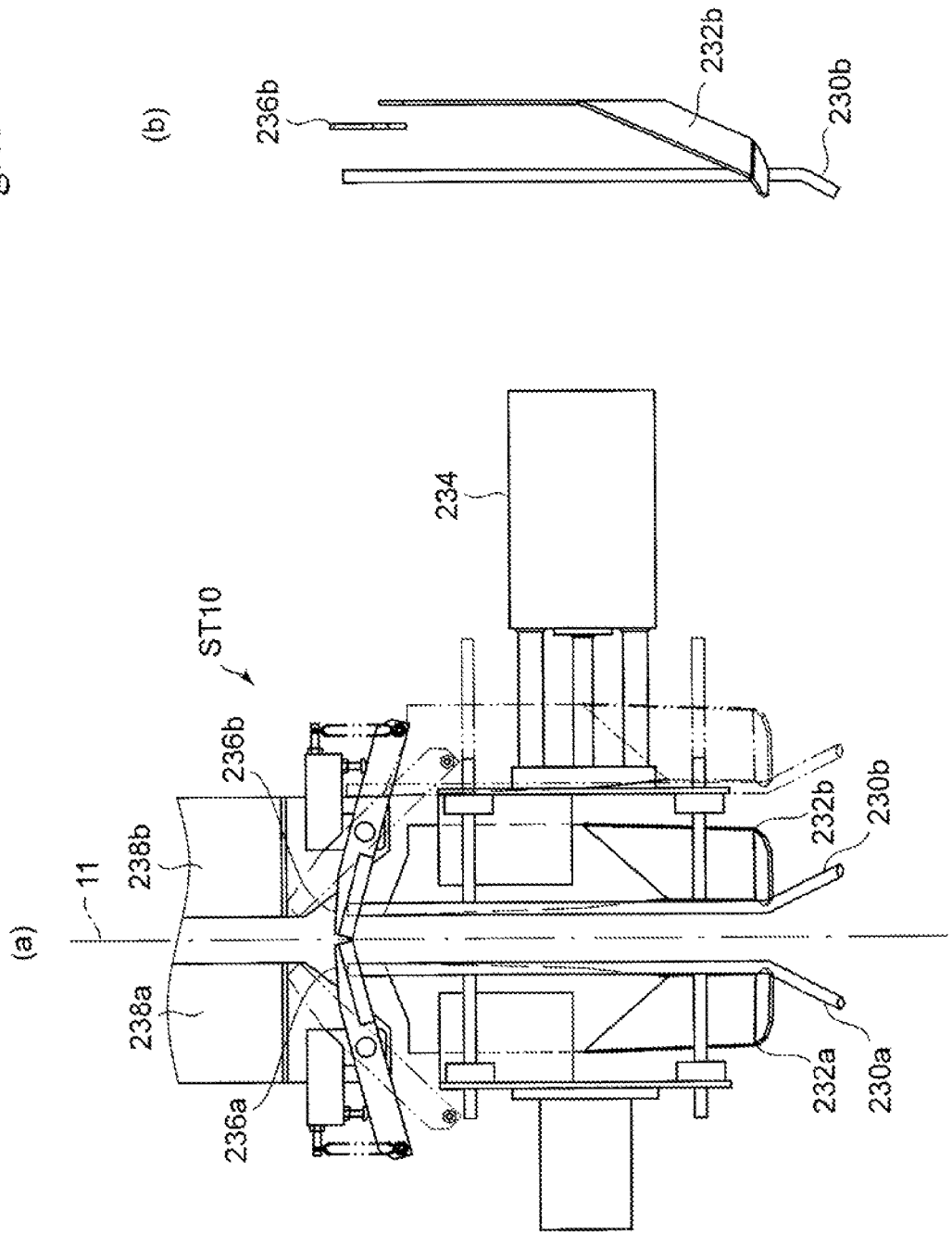
FIG. 63(a) is a plan view schematically showing the upstream side of a transfer separation station.
FIG. 63(b) is a side view schematically showing a guide bar, a guide plate, and a stationary blade of the transfer separation station.
Figure 64:
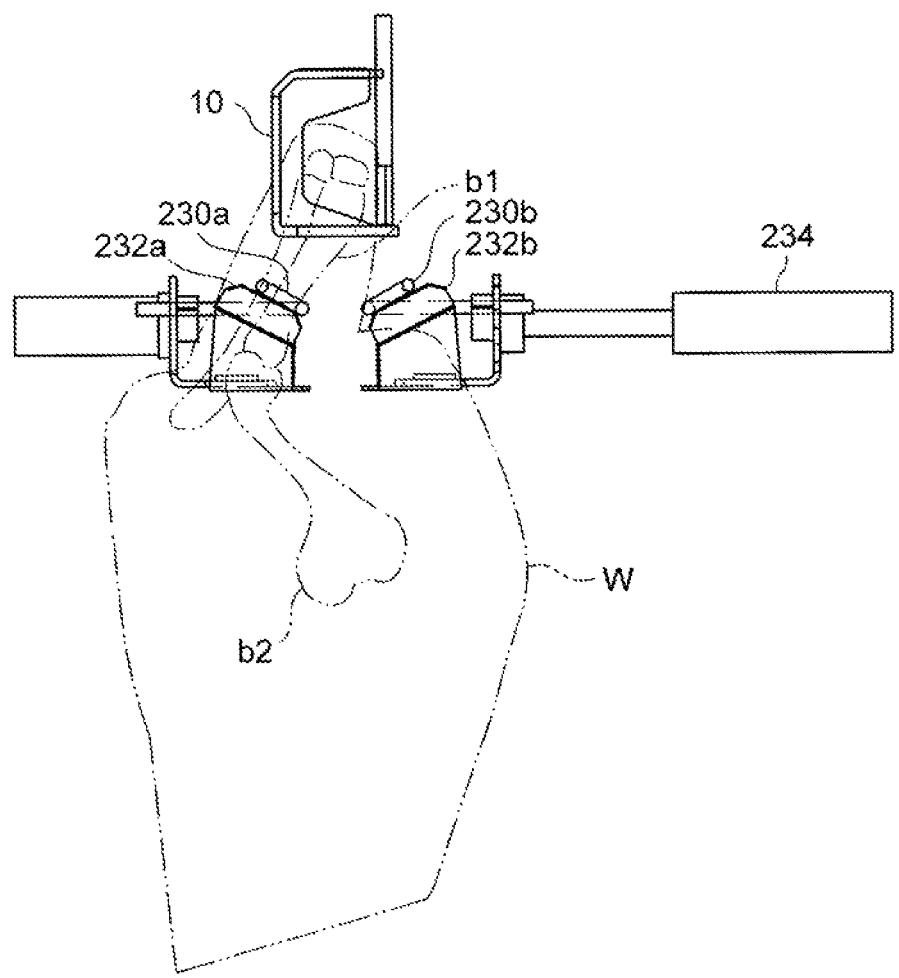
FIG. 64 is a front view schematically showing the upstream side of the transfer separation station together with the work.

FIGS. 61 and 62 schematically show the forearm-bone incision making station ST8 and the work discharge station ST9.

The forearm-bone incision making station ST8 has a frame 204 which is movable in a horizontal direction along the endless track 11, and the frame 204 is fixed to an endless belt 205. The endless belt 205 is rotated by a motor 206, and the frame 204 is moved with the rotation of the endless belt 205. The control device 21 moves the frame 204 in synchronization with the movement of the clamp 10 by controlling the motor 206.

An air cylinder 207 is fixed to the frame 204. A bracket is fixed to the tip of the air cylinder 207, and a lower side support member 208 is fixed to the bracket. In addition, an air cylinder 210 is fixed to the bracket, and an upper side support member 212 is fixed to the tip of the air cylinder 210. The direction of extension and contraction of each of the air cylinders 207 and 210 matches a horizontal direction vertical to the endless track 11.

In addition, an air cylinder 214 is tiltably attached to the frame 204, and the air cylinder 214 is coupled to a holding member 216 via the link mechanism. The holding member 216 can be moved by the air cylinder 214 in a substantially horizontal direction orthogonal to the endless track 11. The lower side support member 208 and the holding member 216 pinch and support the work W in cooperation with each other in the horizontal direction orthogonal to the endless track 11.

On the other hand, the forearm-bone incision making station ST8 has the cutter tool 132 as the attachment of the robot arm 40 similarly to the first incision making station ST5 and the second incision making station ST6.

The robot arm 40 of the forearm-bone incision making station ST8 performs incision making on the work W by using the cutter tool 132 as the third forearm-bone incision making step S30. That is, as indicated by a line L5 in FIG. 26(f), the robot arm 40 performs incision making on the part around the forearm bone b1 of the work W. At this point, the forearm bone b1 is elastically supported by the upper side support member 212.

[Error Occurrence Determination Step]

Information related to an operation is inputted to the control device 21 from various sensors. The control device 21 determines the occurrence of the error in the deboning system on the basis of the inputted information.

[Work Discharge Step/Work Discharge Station]

When the control device 21 determines that the error has occurred, the control device 21 discharges the work W from the deboning system. In order to discharge the work W, the work discharge station ST9 has an air cylinder 220 fixed to the frame 204 and a protrusion member 222 attached to the tip of the air cylinder 220. When the control device 21 determines that the error has occurred, the control device 21 moves the air cylinder 220 in synchronization with the clamp 10, and protrudes the protrusion member 222 toward the clamp 10. With this, the tip part of the work W is pushed out of the clamp 10 by the protrusion member 222, and the work W is detached from the clamp 10.

[Transfer Separation Step/Transfer Separation Station]

FIGS. 63 to 69 schematically show the configuration of the transfer separation station ST10. The transfer separation station ST10 has guide bars 230a and 230b which extend along the endless track 11 and pinch the forearm bone b1 of the work W. Guide plates 232a and 232b are provided below the guide bars 230a and 230b, and the guide plates 232a and 232b pinch the part of the work W in the vicinity of its elbow joint.

The positions of the guide plates 232a and 232b in the vertical direction are substantially the same as those of the guide bars 230a and 230b in the vicinity of the entrance of the guide plates 232a and 232b, but the positions thereof are gradually lowered in the downward direction along the endless track 11. Accordingly, as the work W advances in the downstream direction, meat around the forearm bone b1 is pushed downward by the guide plates 232a and 232b.

Note that the guide bar 230b and the guide plate 232b are coupled to an air cylinder 234, and the force of the guide bars 230a and 230b and the guide plates 232a and 232b for pinching the work W is adjusted by the air cylinder 234.

The transfer separation station ST10 has stationary blades 236a and 236b which are elastically positioned in the vicinity of the exit of the guide bars 230a and 230b and the guide plates 232a and 232b. The stationary blades 236a and 236b cut a muscle remaining in the vicinity of the forearm bone b1.

In addition, the transfer separation station ST10 has lift plates 238a and 238b continuous with the guide plates 232a and 232b and pinch the upper end of the forearm bone b2 of the work W. Round blade cutter devices 240a and 240b are disposed in the vicinity of the lift plates 238a and 238b, and the round blade cutter devices 240a and 240b cut the muscle of the joint between the forearm bone b1 and the upper arm bone b2. The round blade cutter devices 240a and 240b can be vertically moved, and the control device 21 causes the round blade cutter devices 240a and 240b to cut the muscle on the basis of coordinates of the target position A determined from the X-ray image.

Note that the round blade cutter devices 240a and 240b elastically come in contact with the joint by actions of air cylinders 242a and 242b.

After the muscle is cut by the round blade cutter devices 240a and 240b, the control device 21 controls a drive mechanism which is not shown, and the lift plates 238a and 238b are thereby moved downward together with the stationary blades 236a and 236b and the round blade cutter devices 240a and 240b. At this point, since the height of the clamp 10 is unchanged, as shown in FIG. 26(g), the forearm bone b1 and the upper arm bone b2 are separated from each other. After the separation, only the forearm bone b1 is suspended from the clamp 10. At this point, the forearm bone b1 is actually removed from the work W, and the work W is formed of the upper arm bone b2 suspended from the lift plates 238a and 238b and meat adhering to the upper arm bone b2.

Note that the lift plate 238b, the stationary blade 236b, and the round blade cutter device 240b are coupled to an air cylinder 244, and the force of the lift plates 238a and 238b for pinching the upper arm bone b2 is adjusted by the air cylinder 244.

In addition, the transfer separation station ST10 has a stopper 246 which prevents the upper arm bone b2 from returning to the upstream side when the lift plates 238a and 238b descend. Further, the transfer separation station ST10 has an opening/closing door 248 which prevents the upper arm bone b2 from advancing to the downstream side when the lift plates 238a and 238b descend.

On the other hand, the transfer separation station ST10 has an orientation adjustment bar 250 which forcibly aligns the orientation of the work W when the lift plates 238a and 238b descend. The orientation adjustment bar 250 is coupled to an air cylinder 252, and the control device 21 controls the air cylinder 252 to thereby swing the orientation adjustment bar 250.

In addition, the transfer separation station ST10 has a rotary arm 254 which sends the work W to the final separation station ST11 after the lift plates 238a and 238b descend. The opening/closing door 248 and the rotary arm 254 are coupled to an air cylinder 256 via the link mechanism. The control device 21 controls the air cylinder 256, whereby the opening/closing door 248 opens and, at the same time, the rotary arm 254 rotates, and the work W is sent to the final separation station ST11.

Figure 70:
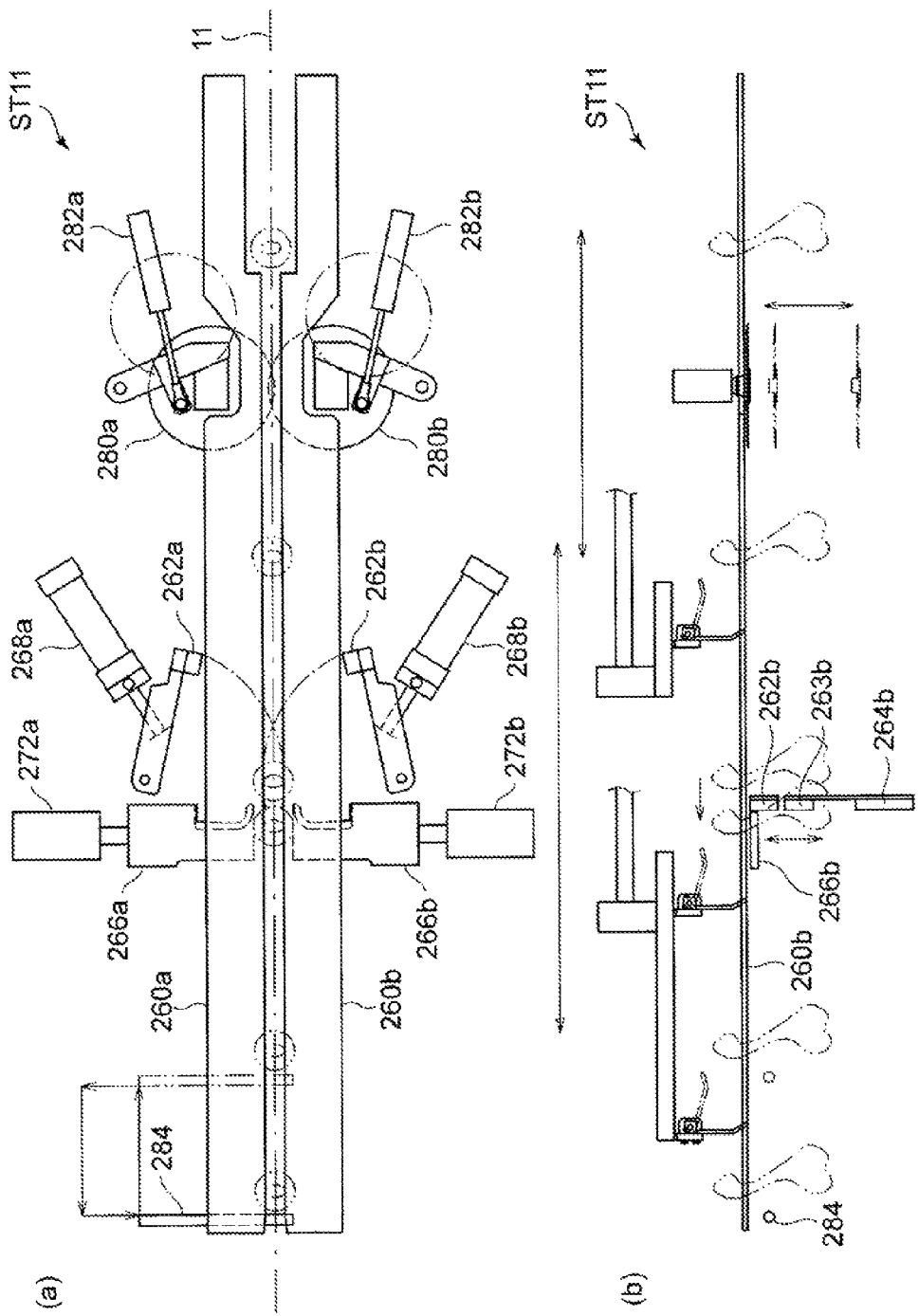
FIG. 70(a) is a plan view schematically showing a final separation station.
FIG. 70(b) is a side view schematically showing the final separation station.
Figure 71:
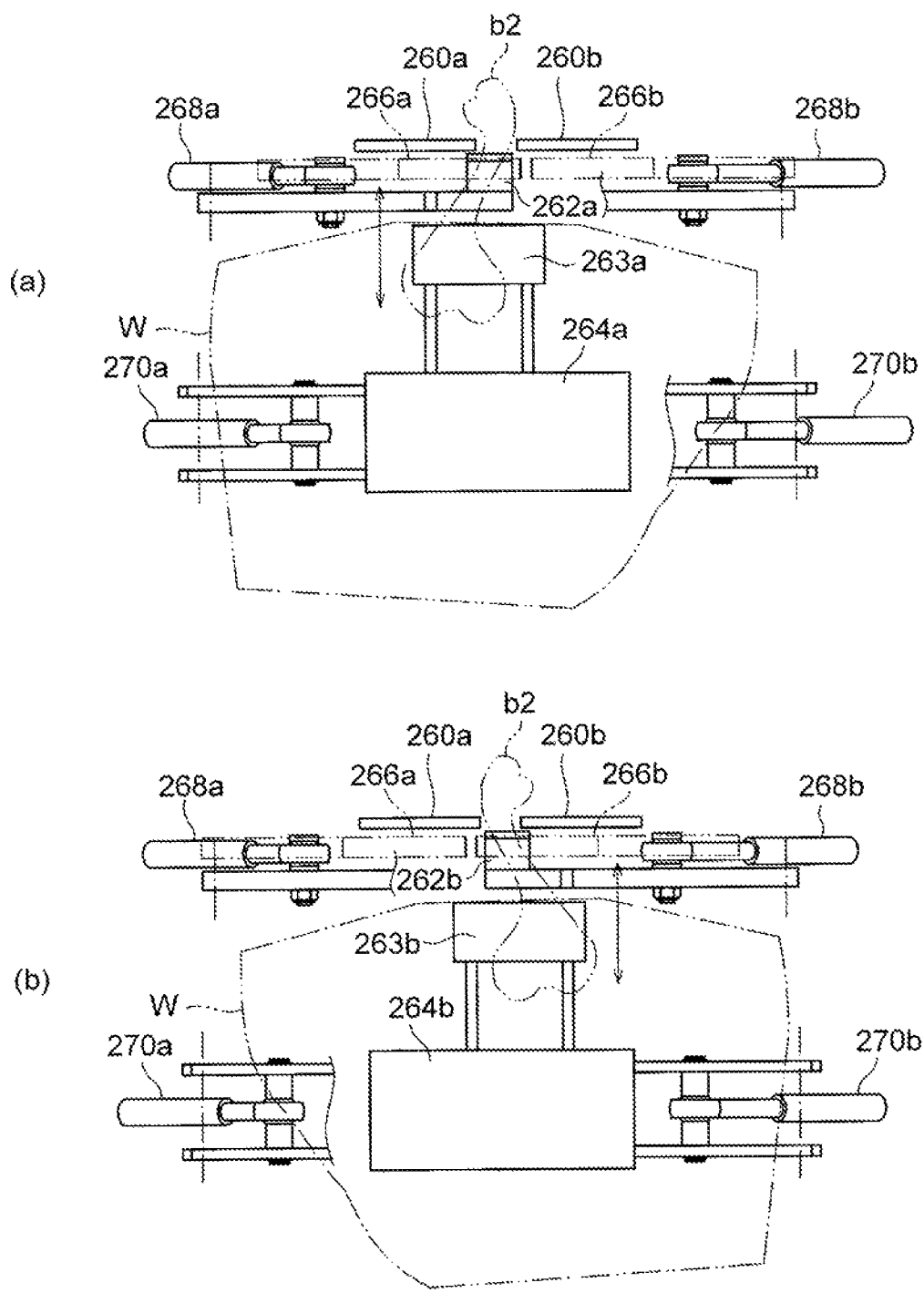
FIGS. 71(a) and 71(b) are front views schematically showing a separation device in the final separation station.
Figure 72:
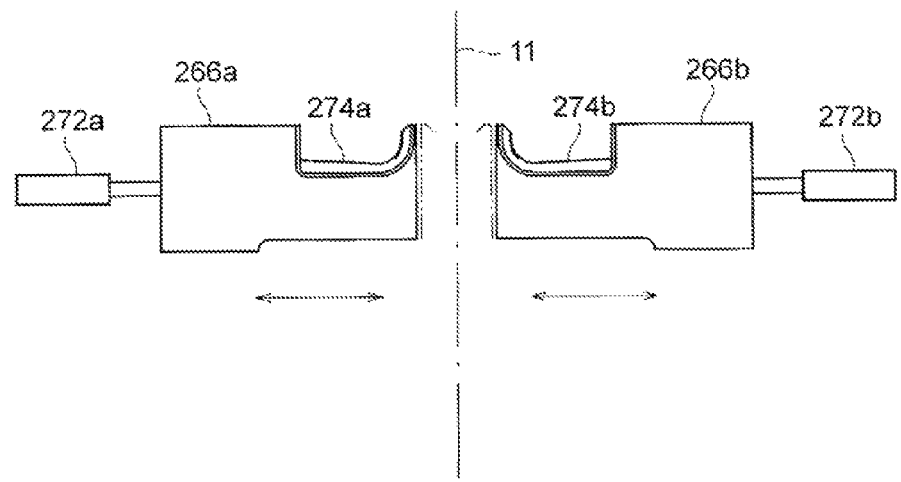
FIG. 72 is a plan view showing a meat separator together with an air cylinder.
Figure 73:
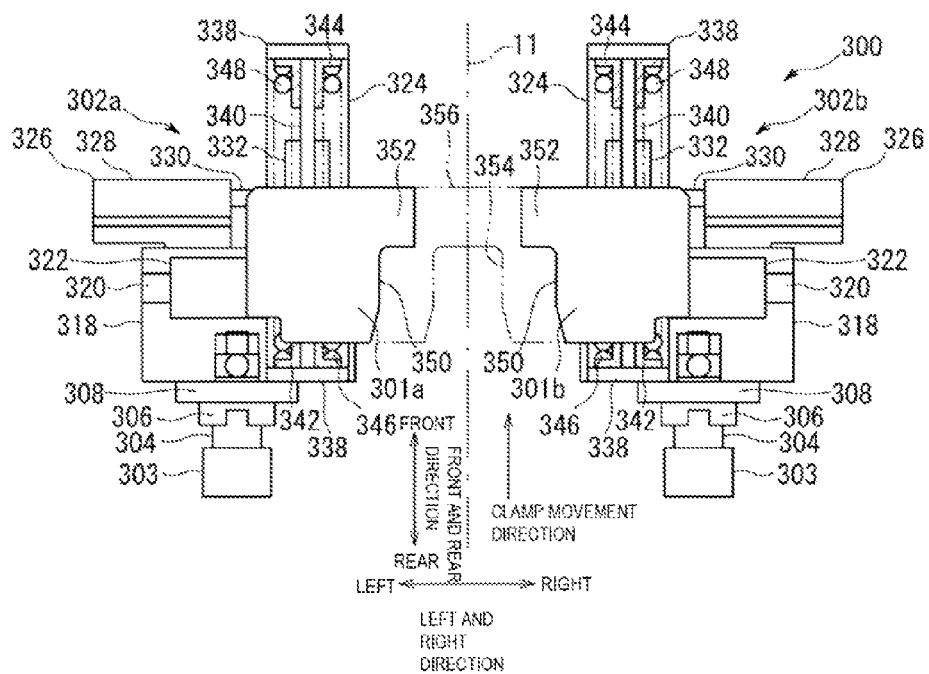
FIG. 73 is a plan view schematically showing a pressing device of the transfer separation station according to another embodiment of the present invention.
Figure 74:
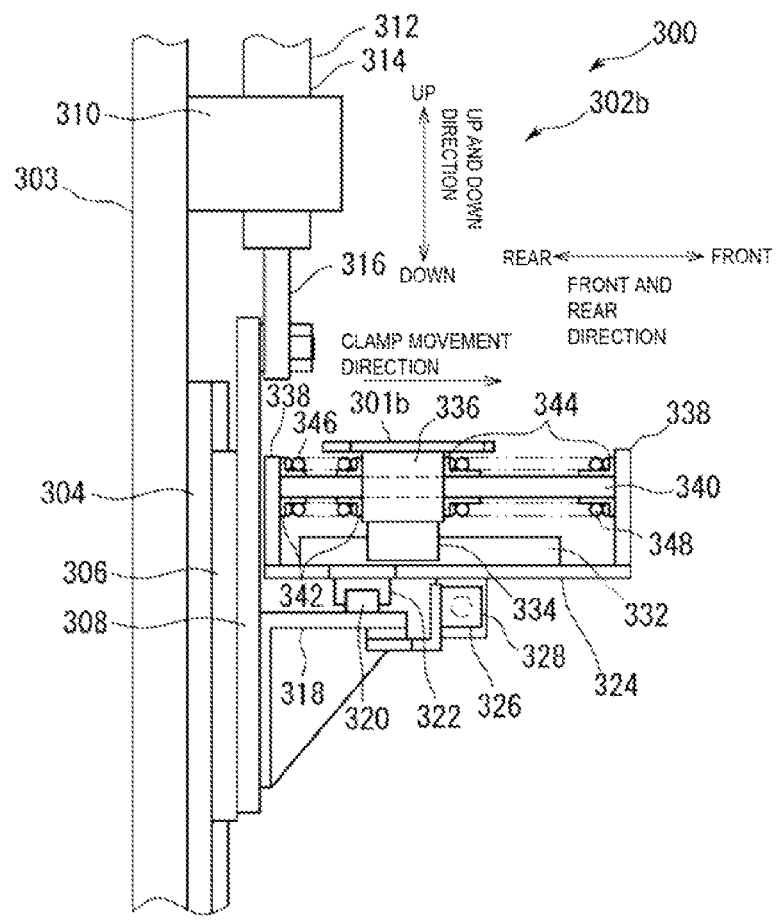
FIG. 74 is a side view schematically showing the pressing device of FIG. 73.
Figure 75:
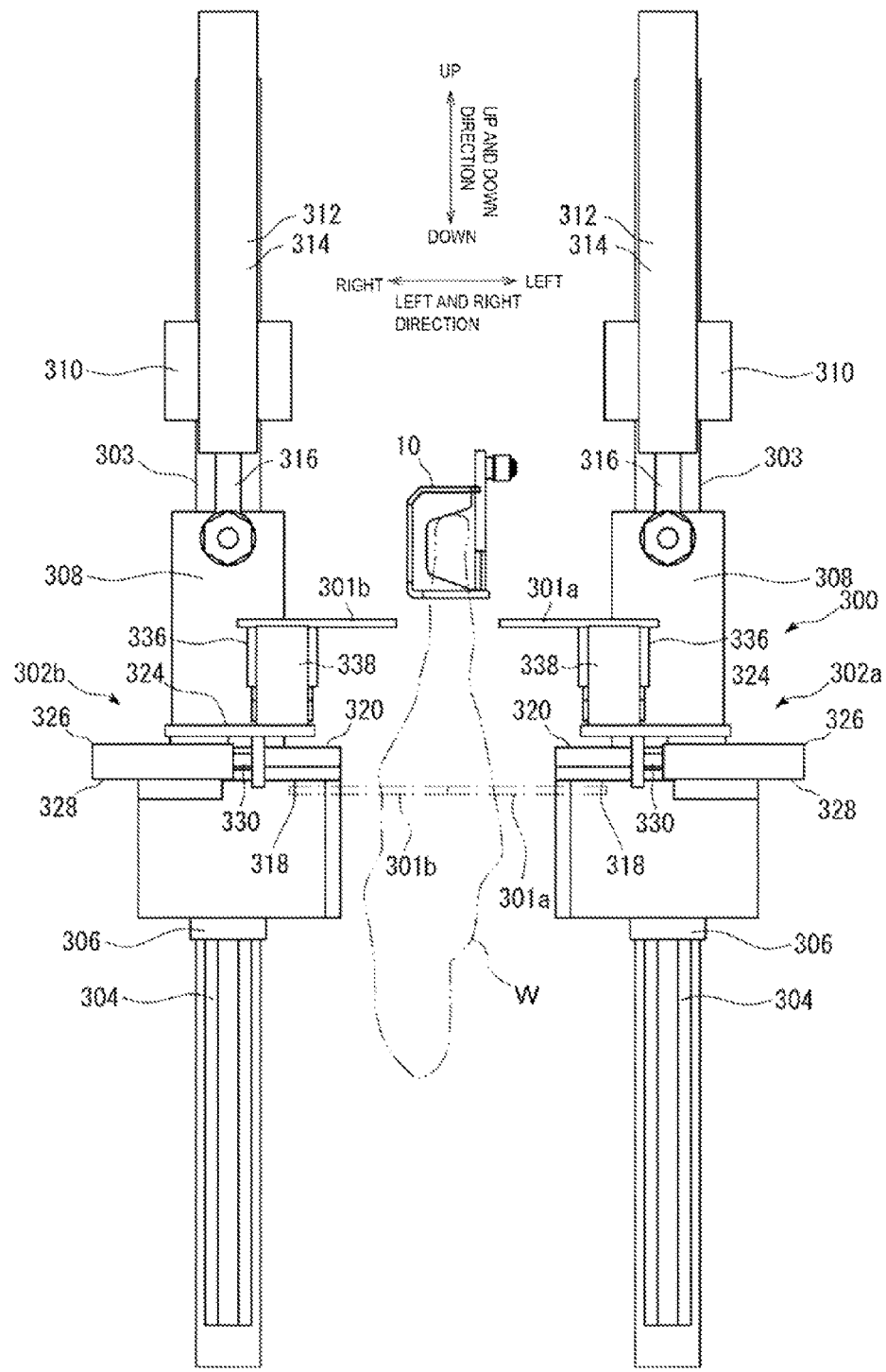
FIG. 75 is a front view schematically showing the pressing device of FIG. 73 together with the work.
Figure 76:
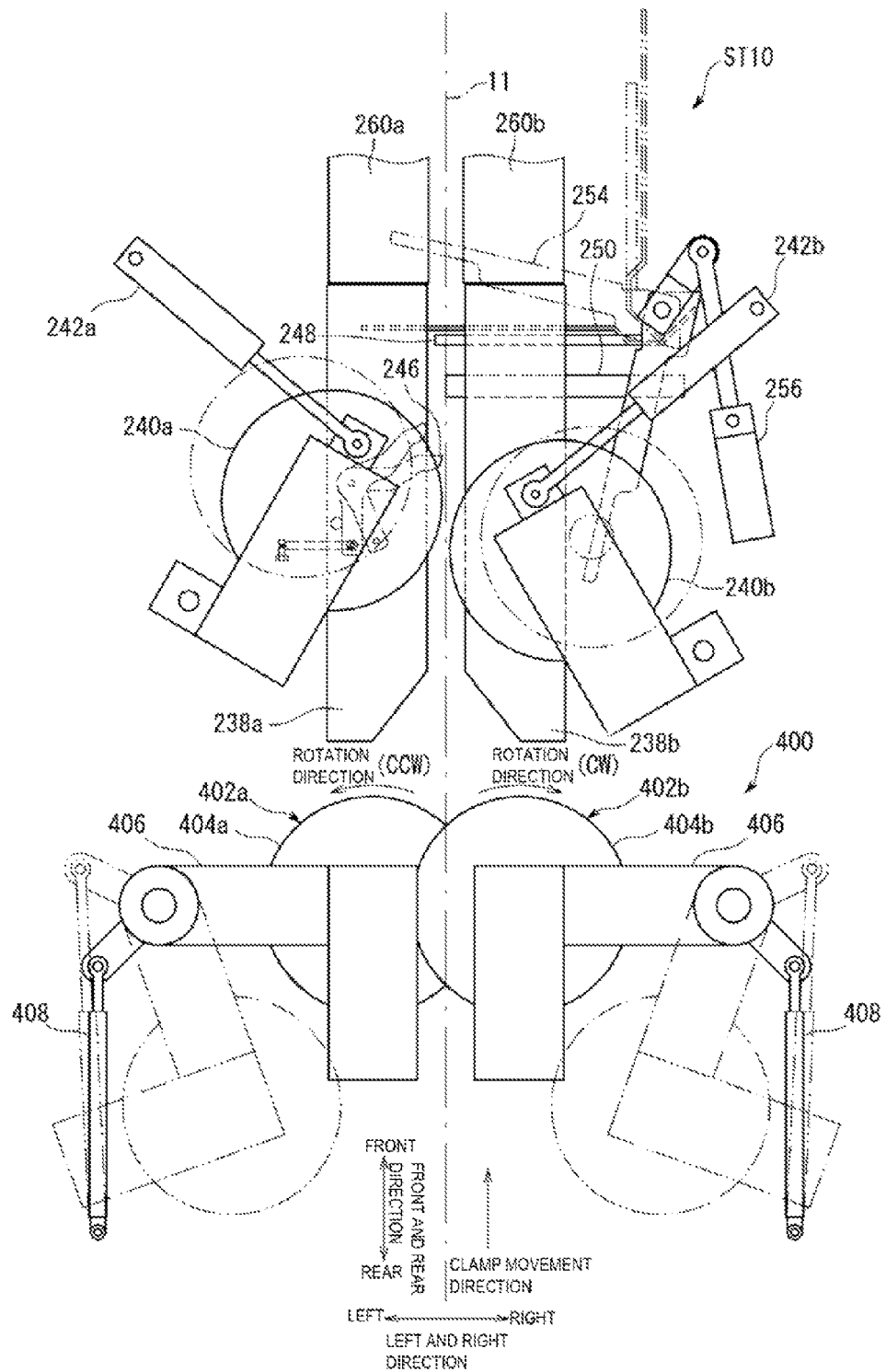
FIG. 76 is a plan view schematically showing the downstream side of the transfer separation station.

[Final Separation Step/Final Separation Station]FIGS. 70 to 72 schematically show the configuration of the final separation station ST11.

The final separation station ST11 has conveyance plates 260a and 260b which pinch the upper arm bone b2. The conveyance plates 260a and 260b are disposed to be continuous with the lift plates 238a and 238b at descent positions, and the work W is transferred from the lift plates 238a and 238b to the conveyance plates 260a and 260b by the rotary arm 254.

The final separation step S42 includes a meat separation step of tearing meat adhering to the upper arm bone b2 and a cutting step of cutting of meat adhering to the upper arm bone b2 after the meat separation step.

A separation device for performing the meat separation step is formed of bone holding members 262a and 262b, meat holding members 263a, 264a, 263b, and 264b, and meat separators 266a and 266b. The bone holding member 262a, the meat holding members 263a and 264a, the separator 266a are used when the work W is the left arm, while the bone holding member 262b, the meat holding members 263b and 264b, and the separator 266b are used when the work W is the right arm.

The bone holding members 262a and 262b are coupled to air cylinders 268a and 268b via the link mechanisms, and the control device 21 can cause each of the bone holding members 262a and 262b to run between the operation position and the wait position by controlling the air cylinders 268a and 268b. Similarly, the meat holding members 263a, 264a, 263b, and 264b are coupled to air cylinders 270a and 270b via the link mechanisms, and the control device 21 can cause each of the meat holding members 263a, 264a, 263b, and 264b to run between the operation position and the wait position by controlling the air cylinders 270a and 270b. The bone holding members 262a and 262b and the meat holding members 263a, 264a, 263b, and 264b are disposed so as to be orthogonal to the axial direction of a groove between the conveyance plates 260a and 260b when they are at the operation positions.

Further, the meat separators 266a and 266b are also coupled to air cylinders 272a and 270b, and the control device 21 can cause each of the meat separators 266a and 266b to run between an operation position which covers the groove between the conveyance plates 260a and 260b and a wait position which is away from the groove by controlling the air cylinders 272a and 272b.

In addition, the meat separators 266a and 266b can be moved in the vertical direction by an actuator which is not shown. The meat separators 266a and 266b have notched parts 274a and 274b on the side of the bone holding members 262a and 262b and the meat holding members 263a, 264a, 263b, and 264b, and the notched parts 274a and 274b pinch the work W in cooperation with the bone holding members 262a and 262b and the meat holding members 263a, 264a, 263b, and 264b. At this point, since the bone holding members 262a and 262b and the meat holding members 263a, 264a, 263b, and 264b are coupled to the air cylinders 270a, 270b, 272a, and 272b, a difference in the size of the work W can be absorbed by the pressure of air.

The control device 21 moves the meat separators 266a and 266b downward in a state in which the bone holding members 262a and 262b and the meat holding members 263a, 264a, 263b, and 264b hold the upper arm bone b2 and meat, and at this time, the meat is torn from the upper arm bone b2 using the edges of the notched parts 274a and 274b. FIG. 26(h) shows the work W from which the meat is torn by the meat separation step.

Note that each of the edges of the notched parts 274a and 274b has a shape obtained by combining an arc and an L. According to the shape of the edge of each of the notched parts 274a and 274b, the edge is moved along the surface of the bone when each of the meat separators 266a and 266b is moved downward, and the meat can be torn neatly.

A cutting device for performing the cutting step is formed of two round blade cutter devices 280a and 280b. The control device 21 determines the length of the upper arm bone 2b from the X-ray image, and controls an actuator which is not shown according to the determined length of the upper arm bone 2b to adjust the heights of the round blade cutter devices 280a and 280b.

In addition, the round blade cutter devices 280a and 280b are coupled to air cylinders 282a and 282b via the link mechanisms, and elastically come in contact with the upper arm bone 2b when meat is cut. Accordingly, the round blade cutter devices 280a and 280b are prevented from biting into the upper arm bone 2b.

As shown in FIG. 26(i), when the meat is separated by the cutting step, the meat is sent out of the deboning system by a belt conveyor which is not shown. On the other hand, as shown in FIG. 26(j), the upper arm bone b2 from which the meat is separated is detached from the conveyance plates 260a and 260b, and is discharged from the deboning system.

Herein, the conveyance mechanism of the work W in the conveyance plates 260a and 260b will be described. The work W having been transferred to the conveyance plates 260a and 260b is pushed by a predetermined distance by a rod 284 coupled to an air cylinder first.

On the groove between the conveyance plates 260a and 260b, there are provided a first slide member 286 and a second slide member 288 which reciprocate along the groove, and the first slide member 286 and the second slide member 288 are driven by air cylinders.

To the lower surface of each of the first slide member 286 and the second slide member 288, a contact plate 290 is coupled using a hinge. The contact plate 290 is hung from each of the first slide member 286 and the second slide member 288, and is configured to be tiltable only in one direction from this state. Specifically, the contact plate 290 is configured to be tiltable only when the contact plate 290 moves in the upstream direction, and does not push the work W when the contact plate 290 moves in the upstream direction. On the other hand, the tilt of the contact plate 290 is prevented when the contact plate 290 moves in the downstream direction, and the contact plate 290 can push the work W when the contact plate 290 moves in the downstream direction.

Thus, the work W is conveyed to the cutting device by the contact plate 290 and, thereafter, the upper arm bone 2b is conveyed by the contact plate 290. The groove between the conveyance plates 260a and 260b is widened on the downstream side and, as shown in FIG. 26(j), the upper arm bone 2b is detached from the groove on the downstream side and discharged from the deboning system.

On the other hand, the forearm bone b1 having been removed from the work W in the transfer separation step S40 is directly conveyed to the bone discharge station ST12 by the clamp 10. Subsequently, the forearm bone b1 is detached from the clamp 10 in the bone discharge station ST12, and is discharged from the deboning system.

Although not shown in the drawing, the bone discharge station ST12 has the same configuration as that of the work discharge station ST9. That is, the bone discharge station ST12 has an air cylinder movable in synchronization with the clamp 10 and a protrusion member attached to the tip of the air cylinder.

According to the above configuration of the embodiment described above, when the hooking members 43a and 43b are stuck into the tip part of the work W, the barbs 47a and 47b are engaged with the bone of the tip part and the extraction of the hooking members 43a and 43b from the tip part is thereby prevented. Consequently, the robot arm 40 can move the work W into which the hooking members 43a and 43b are stuck to the guide rails 60 without dropping the work W. When the work W is moved to the guide rails 60, since the rotation drive mechanism rotates the hooking members 43a and 43b to release the engagement between the barbs 47a and 47b and the bone, the work W is smoothly moved.

In the configuration, when the points 46a and 46b of the hooking members 43a and 43b are stuck into the tip part of the work W, the interval between the first sides of the main body parts 45a and 45b, i.e., the interval between the barbs 47a and 47b is narrower than the interval between the second sides of the main body parts 45a and 45b. Accordingly, after the points 46a and 46b of the hooking members 43a and 43b are stuck, the barbs 47a and 47b are reliably engaged with the bone. On the other hand, even in the case where the interval between the barbs 47a and 47b is narrow, since the interval between the hooking members 43a and 43b is temporarily widened elastically when the barbs 47a and 47b come in contact with the bone, it is possible to smoothly stick the points 46a and 46b of the hooking members 43a and 43b.

In the configuration, the rotation drive mechanism rotates the hooking members 43a and 43b such that the interval between the first sides of the main body parts 45a and 45b approaches the interval between the second sides thereof, and the interval between the barbs 47a and 47b is thereby widened. As a result, the engagement between the barbs 47a and 47b and the bone is reliably released, and it is possible to smoothly detach the work W from the hooking members 43a and 43b.

In the configuration, since the swing of the work W is regulated by the swing regulation mechanism, the detachment of the work W from the hooking members 43a and 43b by the swing is prevented.

In the configuration, while the work W is moved along the groove of the guide rails 60, the incision making of the forearm bone b1 is performed using the upstream side stationary blade 72 and the downstream side stationary blade 74. Consequently, it is possible to reduce manual pre-processing to increase the automation rate.

Particularly, the downstream side stationary blade 74 performs incision making on the elbow side of the forearm bone b1 after the upstream side stationary blade 72 performs incision making on the wrist side of the forearm bone b1, whereby meat is neatly torn from the forearm bone b1.

According to the above configuration, only by placing the work W having been subjected to the manual pre-processing at the upstream end of the belt conveyor 24, it is possible to automatically convey the work W to the clamp 10. Accordingly, it is possible to enhance the processing ability of the deboning system, and achieve the processing ability of, e.g., 600 pieces/hour.

According to the above configuration, by determining the left or the right on the basis of the posture of the work W on the belt conveyor 24, it is possible to reliably determine the left or the right with a simple configuration.

In addition, according to the above configuration of the embodiment described above, since the intensity distribution of the X-ray applied to the work W is adjusted using the filter, the clear X-ray image is obtained. Consequently, in the case where incision making is executed on the basis of the X-ray image, it is possible to cause the course of the incision making to precisely match the outline of the bone so that yields are improved, and application of an excessive load to the cutter 133 is prevented.

According to the above configuration, by rotating the work W about the vertical axis in the rotation direction corresponding to the right or the left of the work W, the X-ray image suitable for the determination of the course of incision making is obtained. Consequently, in the case where incision making is executed on the basis of the X-ray image, yields are further improved and the application of the excessive load to the cutter 133 is further prevented.

According to the above configuration, by rotating the clamp 10 such that the incident angle of the X-ray relative to the cut surface separated from the trunk of the work W is more than 30° and less than 45°, the X-ray image suitable for the determination of the course of incision making is reliably obtained.

According to the above configuration, it is possible to capture the X-ray image while moving the clamp 10. Consequently, it is possible to capture the X-ray image without lowering the processing ability of the deboning system.

Further, according to the above configuration of the embodiment described above, it is possible to remove the shoulder blade b3 from the suspended work W.

According to the above configuration, the motor 154 constitutes the movement mechanism which moves the bottom holder 170 and the upper side support member 158 in synchronization with the movement of the clamp 10, and it is possible to remove the shoulder blade b3 from the work W which is conveyed with the movement of the clamp 10. Consequently, in the deboning system of the bone-in meat to which the shoulder blade removal device of the bone-in meat is applied, it is possible to remove the shoulder blade b3 without lowering the processing ability.

In the configuration, the air cylinder 172 constitutes the left/right position adjustment mechanism which adjusts the position of the bottom holder 170 in the direction of movement of the clamp 10 according to the left or the right of the work W. According to the above configuration, the work W is properly bent according to the left or the right of the work W, and the end part of the shoulder blade b3 is exposed. As a result, the chuck unit 190 can reliably chuck and remove the shoulder blade b3.

In the configuration, the bottom holder 170 has the bottom plate 174 bent in the V-shape and the side plate 176 attached to one side edge of the bottom plate 174 along the endless track 11. According to the above configuration, the work W is properly bent and the end part of the shoulder blade b3 is exposed with a simple configuration. As a result, the chuck unit 190 can reliably chuck and remove the shoulder blade b3.

According to the above configuration, the wiper 186 sweeps away the ribs w1, and the end part of the shoulder blade b3 is thereby exposed. As a result, the chuck unit 190 can reliably chuck and remove the shoulder blade b3.

According to the above configuration, the grip member 194 is provided with the blade, and the grip member 194 can perform incision making on the part around the end part of the shoulder blade b3. As a result, the chuck unit 190 can reliably chuck and remove the shoulder blade b3.

The present invention is not limited to the embodiment described above, and includes an embodiment obtained by modifying the above-described embodiment.

For example, FIGS. 73 to 76 schematically show another configuration of the transfer separation station ST10 for performing the transfer separation step S40. The transfer separation station ST10 has a pressing device 300 and an olecranon incision making device 400 which are disposed along the endless track 11.

The pressing device 300 has a pair of pressing members 301a and 301b disposed on both sides of the endless track 11. The pressing members 301a and 301b can reciprocate back and forth along the direction of conveyance of the work W, i.e., the direction of movement of the clamp 10, can reciprocate from side to side along a left and right direction orthogonal to the direction of movement of the clamp 10, and can reciprocate vertically along an up and down direction orthogonal to the direction of movement of the clamp 10.

Specifically, the pressing device 300 has a pair of pressing units 302a and 302b which are disposed so as to oppose each other over the endless track 11. Each of the pressing units 302a and 302b has a column 303, and a straight guide 304 which extends along the up and down direction is fixed to the column 303. A slider 306 is attached to the straight guide 304 so as to be slidable along the up and down direction, and a movable wall 308 is fixed to the slider 306. Consequently, the movement of the movable wall 308 in the up and down direction is guided by the slider 306 and the straight guide 304.

On the other hand, a cylinder part 314 of an air cylinder 312 is fixed to the column 303 via a bracket 310. The tip of a rod part 316 of the air cylinder 312 is coupled to the movable wall 308. Consequently, the control device 21 can vertically move the movable wall 308 by controlling the air cylinder 312 as the actuator.

A bracket 318 is fixed to the movable wall 308, and a straight guide 320 which extends along the left and right direction is attached to the bracket 318. A slider 322 is attached to the straight guide 320 so as to be slidable along the left and right direction.

A movable stage 324 is fixed to the slider 322, and the movement of the movable stage 324 in the left and right direction is guided by the slider 322 and the straight guide 320.

On the other hand, a cylinder part 328 of an air cylinder 326 is fixed to the bracket 318. The tip of a rod part 330 of the air cylinder 326 is coupled to the movable stage 324. Consequently, the control device 21 can move the movable stage 324 from side to side by controlling the air cylinder 326 as the actuator.

A straight guide 332 which extends along the endless track 11, i.e., along the direction of movement of the clamp 10 is attached to the movable stage 324. A slider 334 is attached to the straight guide 332 so as to be slidable along the direction of movement of the clamp 10.

A movable stage 336 is fixed to the slider 334, and the movement of the movable stage 336 in the direction of movement of the clamp 10 is guided by the slider 334 and the straight guide 332.

On the other hand, end walls 338 are fixed to the movable stage 324 on both sides in the direction of movement of the clamp 10, and the movable stage 336 is disposed between the end walls 338. A rod 340 which extends along the direction of movement of the clamp 10 is provided between the end walls 338, and the rod 340 extends through the movable stage 324.

Compression coil springs 346 and 348 are disposed between the end walls 338 and the movable stage 336 via spring seats 342 and 344, and the rod 340 extends through the spring seats 342 and 344 and the compression coil springs 346 and 348. Consequently, the movable stage 336 is movable along the direction of movement of the clamp 10 while receiving biasing forces of the compression coil springs 346 and 348 as elastic members.

The pressing members 301a and 301b are fixed to the movable stages 336 which oppose each other over the endless track 11. The pressing members 301a and 301b have side edges 350 which are substantially in parallel with each other and extend along the endless track 11, and protrusion parts 352 which protrude further toward the endless track 11 than the side edges 350. The protrusion parts 352 are positioned on the downstream side of the side edges 350 in the direction of movement of the clamp 10. Accordingly, each of the pressing members 301a and 301b has the shape of a substantially L-shaped plate. As indicated by a two-dot chain line in FIG. 63, the control device 21 can dispose the pressing members 301a and 301b at first operation positions which bring the protrusion parts 352 into contact with each other by controlling the air cylinders 326.

When the pressing members 301a and 301b are at the first operation positions, the pressing members 301a and 301b are positioned slightly below the clamp 10 in the up and down direction and pinch the part in the vicinity of the upper end part of the forearm bone b1 with a space. In other words, when the pressing members 301a and 301b are at the first operation positions, the side edges 350 thereof form a groove 354 for pinching the part in the vicinity of the upper end part of the forearm bone b1. In addition, when the pressing members 301a and 301b are at the operation positions, the protrusion parts 352 thereof form an engagement part 356 which is engaged with the part in the vicinity of the upper end part of the forearm bone b1.

Figure 65:
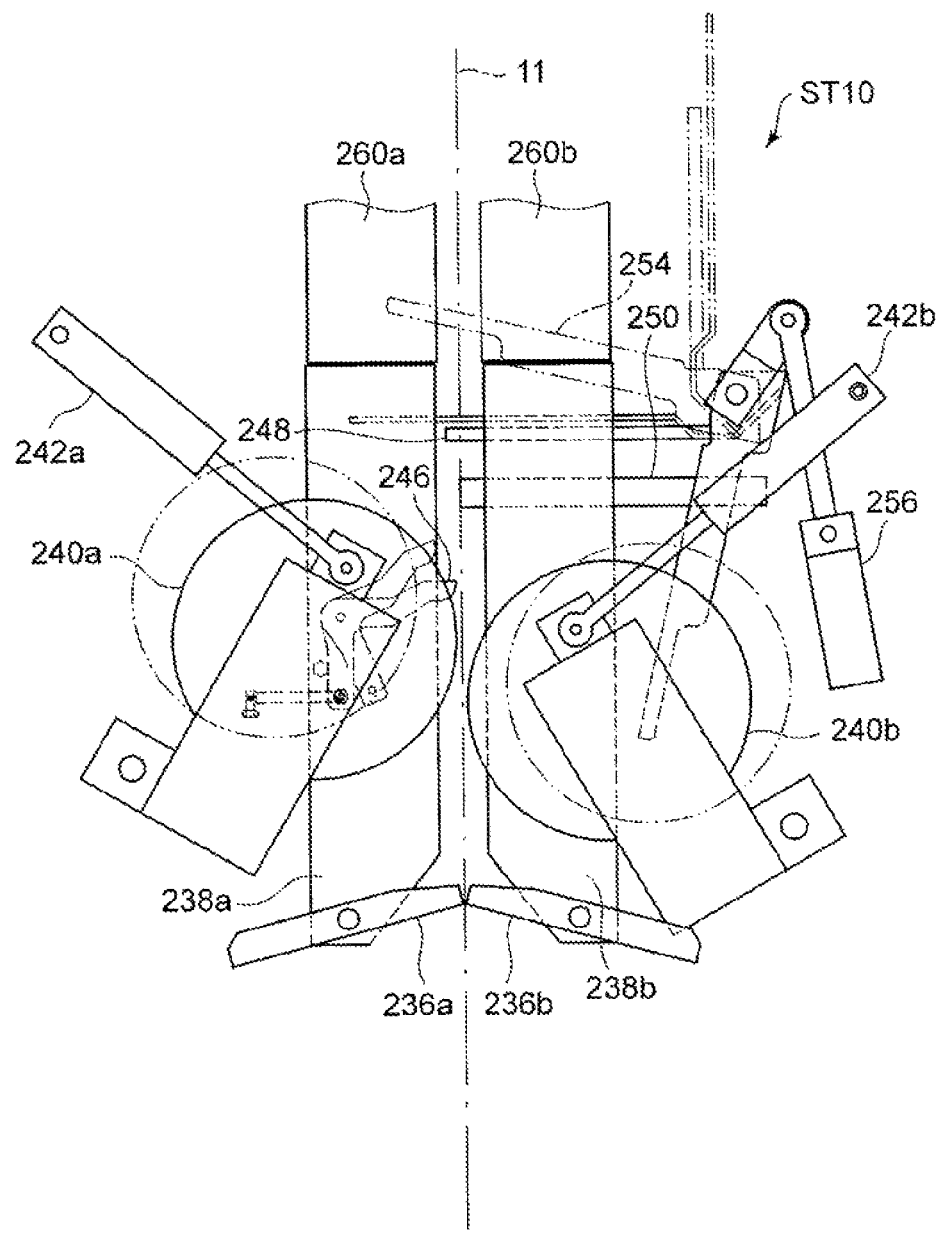
FIG. 65 is a plan view schematically showing the downstream side of the transfer separation station.
Figure 66:
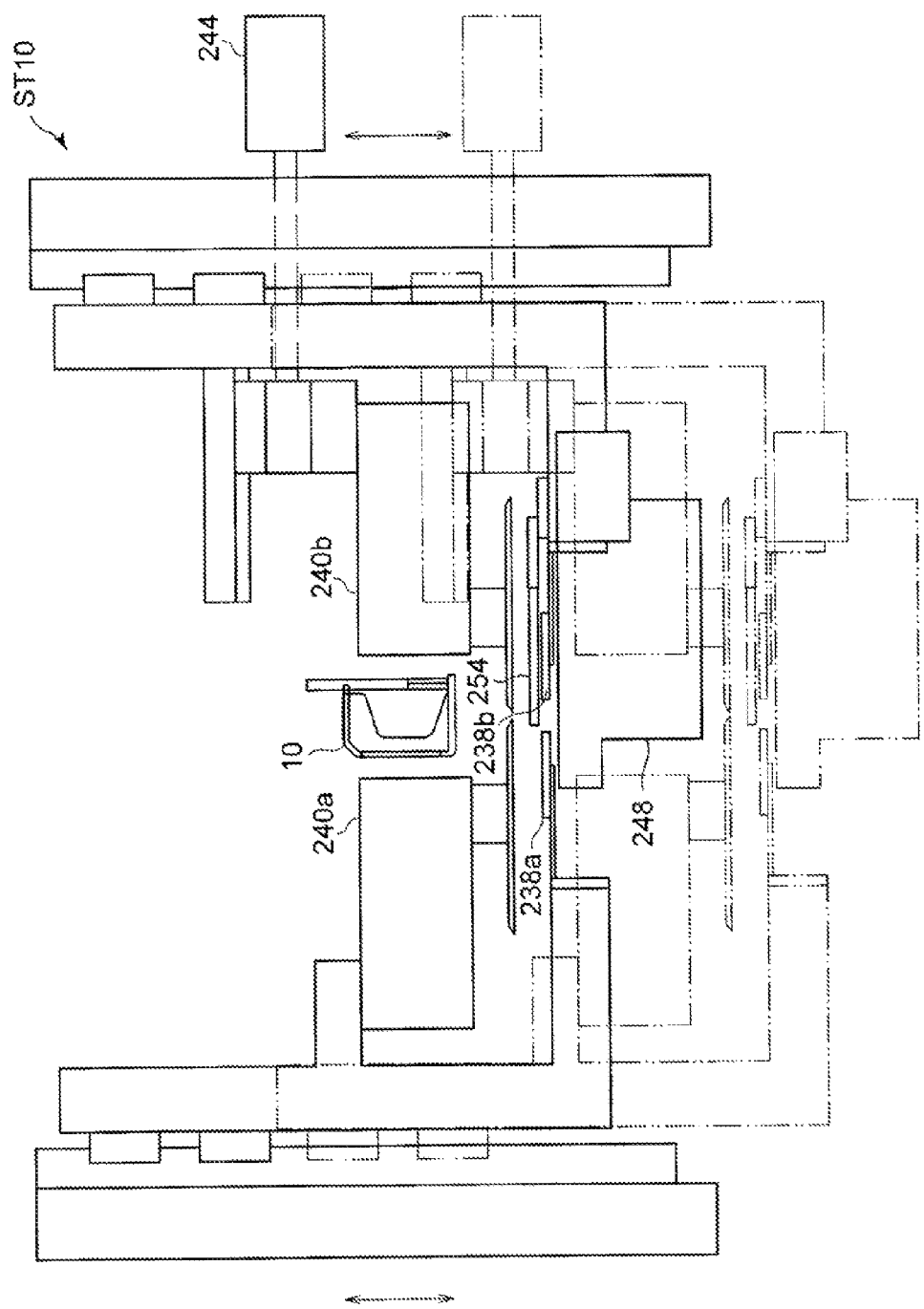
FIG. 66 is a front view schematically showing the downstream side of the transfer separation station.
Figure 67:
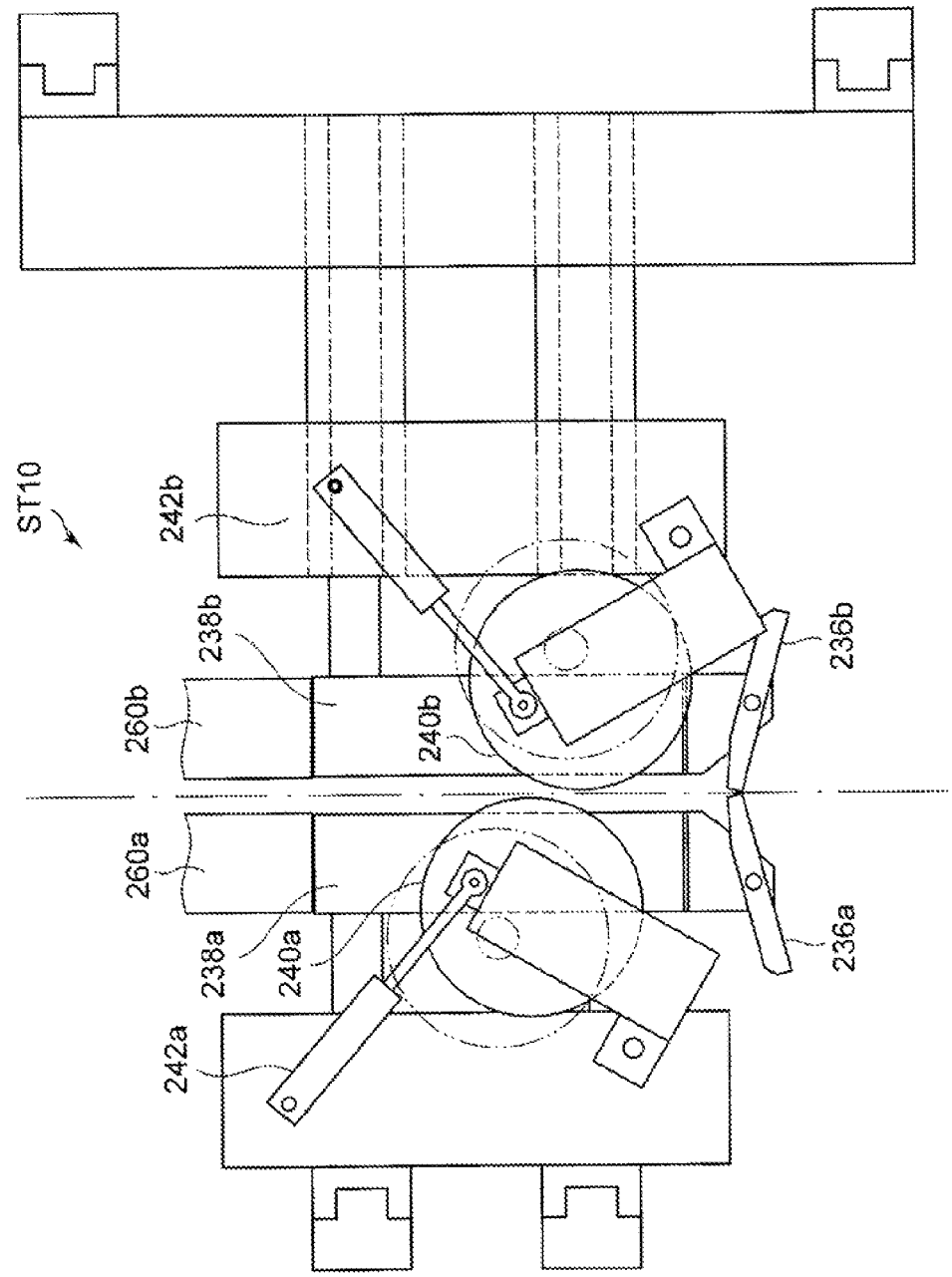
FIG. 67 is a plan view schematically showing the downstream side of the transfer separation station.
Figure 68:
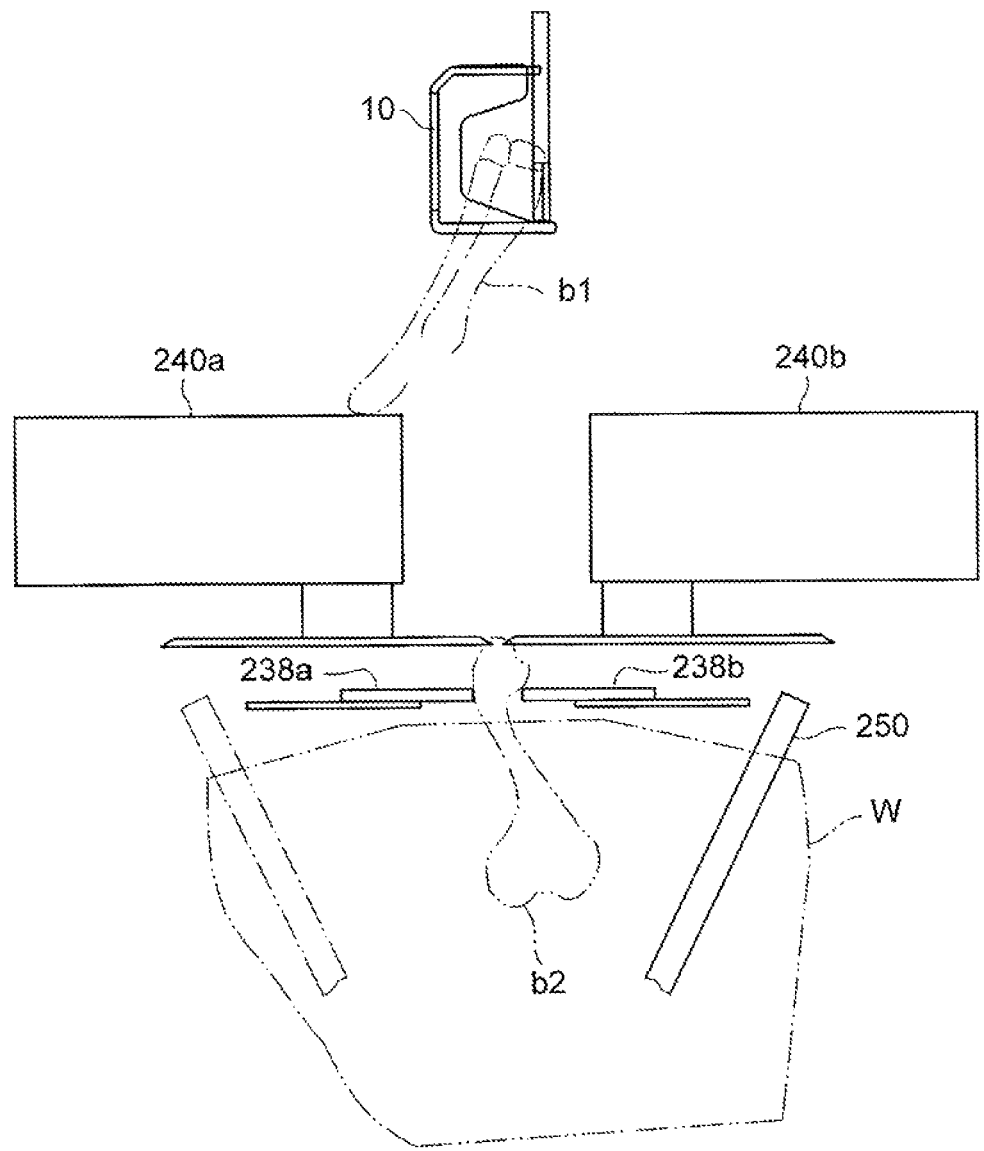
FIG. 68 is a view for explaining separation of the forearm bone from the work in the transfer separation station.
Figure 69:
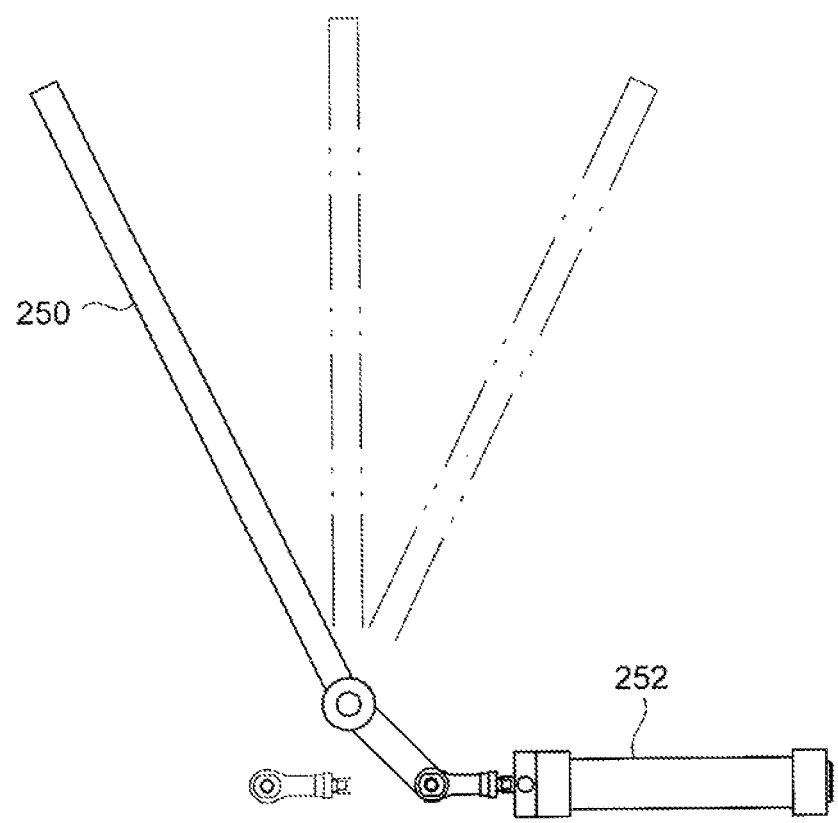
FIG. 69 is a view for explaining the operation of an orientation adjustment bar.
Figure 77:
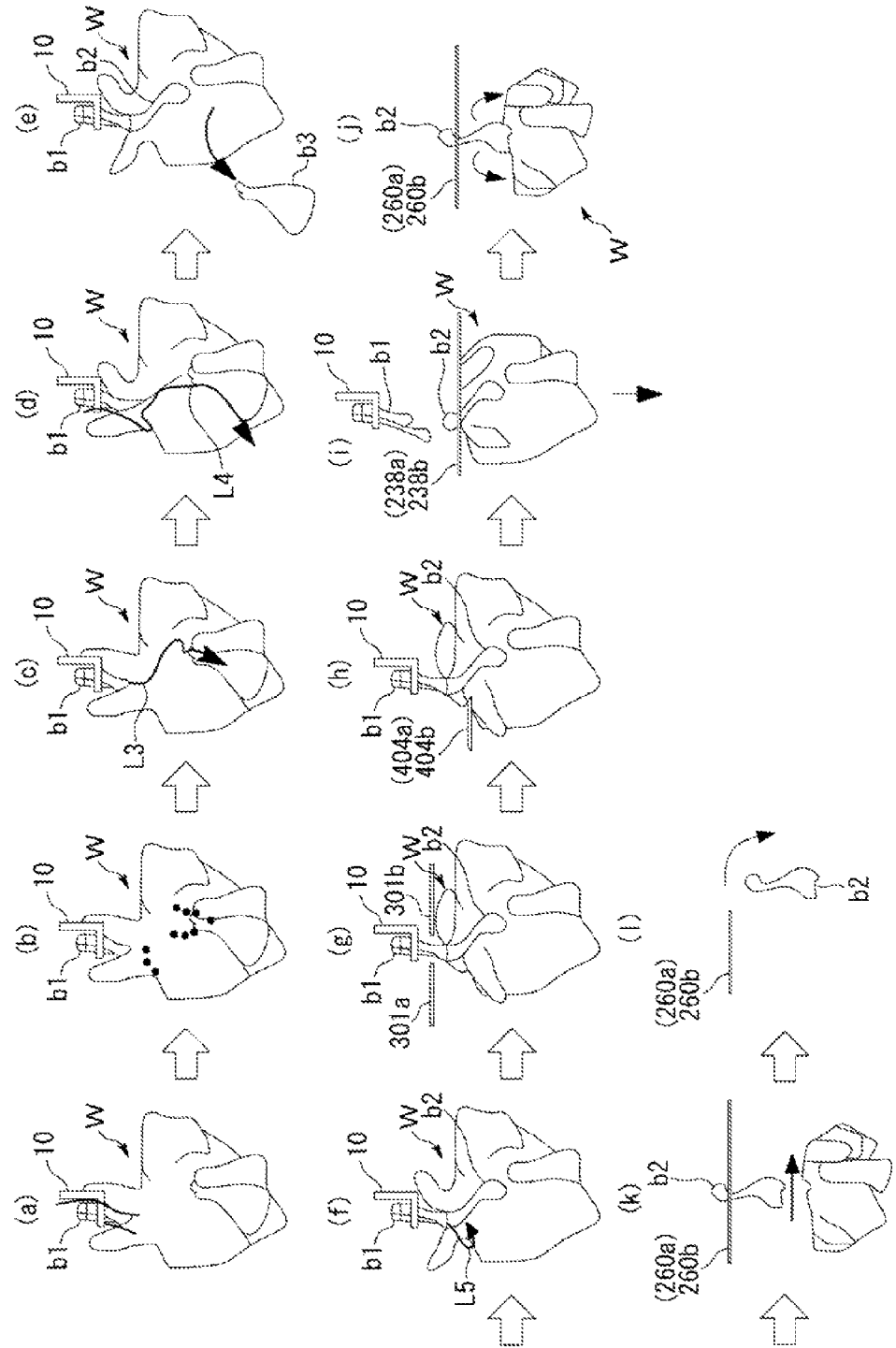
FIGS. 77(a), 77(b), 77(c), 77(d), 77(e), 77(f), 77(g), 77(h), 77(i), 77(j), 77(k), and 77(l) are views for explaining a deboning method executed by a deboning system of another embodiment.

When the pressing members 301a and 301b pinch the part in the vicinity of the upper end part of the forearm bone b1, the control device 21 can move the movable walls 308 downward by controlling the air cylinders 312 to dispose the pressing members 301a and 301b at second operation positions, as indicated by the two-dot chain line in FIG. 65. The second operation positions are positioned slightly below the joint (elbow joint) between the forearm bone b1 and the upper arm bone b2 in the up and down direction. Consequently, as shown in FIG. 77(g), the pressing members 301a and 301b can press down meat around the forearm bone b1 until the elbow joint is exposed during the movement from the first operation positions to the second operation positions (pressing step).

Subsequently, after the meat is pressed down, the control device 21 can dispose the pressing members 301a and 301b at non-operation positions which cause the pressing members 301a and 301b to be spaced apart from each other by controlling the air cylinders 326, and can move the movable walls 308 upward by controlling the air cylinders 312. When the pressing members 301a and 301b are disposed at the non-operation positions, the work W suspended from the clamp 10 can pass between the protrusion parts 352 of the pressing members 301a and 301b.

Note that, when the pressing members 301a and 301b are disposed at the first operation positions, the protrusion parts 352 are pushed by the work W which is conveyed by the clamp 10, and are moved downstream in the direction of movement of the clamp 10. The pressing members 301a and 301b can press down the meat around the forearm bone b1 by moving to the second operation positions during the movement. When the pressing members 301a and 301b are disposed at the non-operation positions, the pressing members 301a and 301b are moved upstream in the direction of movement of the clamp 10 by the biasing force of the compression coil spring 348, and can return to the original positions.

The olecranon incision making device 400 is disposed on the downstream side of the pressing device 300 in the direction of movement of the clamp 10. The olecranon incision making device 400 is a device for cutting meat around the olecranon of the work W suspended from the clamp 10, and has two olecranon cutter devices 402a and 402b which are disposed along the endless track 11.

The olecranon cutter devices 402a and 402b preferably have round blades 404a and 404b as olecranon cutters. The olecranon cutter devices 402a and 402b are swingably supported within a horizontal plane by arms 406, and are movable between operation positions at which the olecranon cutter devices 402a and 402b are in contact with the work W and non-operation positions at which the olecranon cutter devices 402a and 402b are apart from the work W by controlling air cylinders 408 as the actuators.

In addition, the olecranon cutter devices 402a and 402b are vertically movable, and the control device 21 can set the positions of the round blades 404a and 404b in the up and down direction to positions around the olecranon on the basis of coordinates of the target position E (see FIG. 45) determined from the X-ray image.

Consequently, the control device 21 can cut the meat around the olecranon as shown in FIG. 77(h) by controlling the positions of the olecranon cutter devices 402a and 402b to thereby bring the round blades 404a and 404b into contact with the part around the olecranon of the work W suspended from the clamp 10 (olecranon incision making step).

Note that the round blades 404a and 404b can elastically come in contact with the work W by actions of the air cylinders 408.

In the present embodiment, by bringing the round blades 404a and 404b into contact with the work W from the rear side in the direction of movement of the clamp 10, it is possible to cut the meat around the olecranon. Note that the clamp 10 is rotated by the fourth clamp rotation device 19 such that the olecranon of the work W is disposed on the rear side in the direction of movement of the clamp 10.

In addition, preferably, the olecranon cutter devices 402a and 402b are electric cutters, the round blades 404a and 404b come in contact with the work W while rotating, and it is thereby possible to reliably cut the meat around the olecranon. Preferably, the round blade 404a positioned on the left side in the direction of movement of the clamp 10 is rotated counterclockwise (CCW) as viewed from above, while the round blade 404b positioned on the right side is rotated clockwise (CW) as viewed from above.

According to the embodiment described above, there is provided the deboning system of the bone-in meat including the clamp 10 which is movable along the endless track 11 and used for suspending the bone-in meat by gripping the tip part of the forearm bone b1 of the bone-in meat, the forearm-bone incision making device which is disposed along the endless track 11 and used for cutting the meat around the forearm bone b1 of the bone-in meat suspended by the clamp 10, the olecranon incision making device 400 which is disposed along the endless track 11 and used for cutting the meat around the olecranon of the bone-in meat suspended by the clamp 10, and the lift plates 138a and 138b which are disposed along the endless track 11 and used for pulling the bone-in meat suspended by the clamp 10 such that the forearm bone b1 and the upper arm bone b2 of the bone-in meat are separated from each other in which the forearm-bone incision making device has the robot arm 40 disposed along the endless track 11 and the cutter tool (forearm cutter) 132 attached to the robot arm 40, and the olecranon incision making device 400 has the pair of the olecranon cutters disposed on both sides of the endless track 11.

According to the deboning system of the bone-in meat described above, the meat around the forearm bone b1 is cut using the cutter tool 132 of the forearm-bone incision making device, and the meat around the olecranon is cut using the pair of the olecranon cutters of the olecranon incision making device 400. Thus, by using the forearm-bone incision making device and the olecranon incision making device 400, it is possible to enhance the automation rate.

On the other hand, according to the deboning system of the bone-in meat described above, after the meat around the olecranon is cut using the pair of the olecranon cutters, the forearm bone b1 and the upper arm bone b2 can be separated from each other. In this case, as compared with the case where the meat around the olecranon is cut using the cutter tool 132 attached to the robot arm 40, meat adhering to the part around an olecranon fossa of the upper arm bone b2 is reduced and yields are improved.

Figure 78:
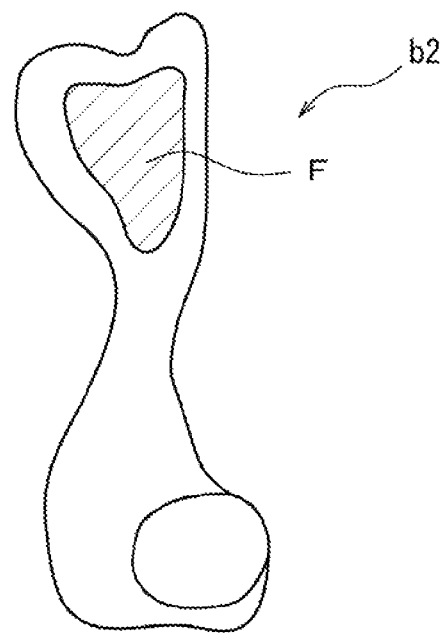
FIG. 78 is a schematic diagram for explaining an olecranon fossa of an upper arm bone.

Herein, FIG. 78 is a perspective view schematically showing the upper arm bone b2, and an olecranon fossa F corresponds to a hatched region in FIG. 78. In a state in which the bone-in meat is suspended from the clamp W, the olecranon fossa F is covered by the olecranon of the forearm bone b1, and hence it is not possible to directly cut meat present in a gap between the olecranon fossa F and the olecranon using the cutter tool 132.

To cope with this, after various studies conducted by the present inventors, it has been found that, when the forearm bone b1 and the upper arm bone b2 are separated from each other after the meat around the olecranon is cut using the olecranon incision making device 400, meat can be torn from the olecranon fossa F and yields are improved.

In addition, in the case where the pair of the olecranon cutters include the pair of the round blades 404a and 404b, it is possible to reliably cut the meat around the olecranon with a simple configuration.

Further, the deboning system of the bone-in meat of the embodiment described above includes the X-ray imaging station ST4 as the olecranon position measurement device for measuring the position of the olecranon of the bone-in meat, and the olecranon incision making device 400 operates according to the result of the measurement of the olecranon position measurement device.

According to the above configuration, the olecranon incision making device 400 operates according to the measurement result of the olecranon position measurement device, and yields are thereby further improved.

In addition, since the transfer separation station ST10 has the lift plates 238a and 238b as at least one pinching part which can be vertically moved while pinching the upper end part of the upper arm bone b2, it is possible to separate the forearm bone b1 and the upper arm bone b2 from each other with a simple configuration. Subsequently, after the forearm bone b1 and the upper arm bone b2 are separated from each other by using the configuration, if meat is cut off from the upper arm bone b2 while the upper end part of the upper arm bone b2 is gripped, it is possible to separate the meat from the upper arm bone b2 with a simple configuration without requiring an auxiliary clamp for preventing dislocation of the joint between the forearm bone b1 and the upper arm bone b2.

Further, the deboning system of the bone-in meat of the embodiment described above includes the pressing device 300 disposed along the endless track 11, and the pressing device 300 is disposed on the upstream side of the lift plates 138a and 138b in the direction of movement of the clamp 10, and presses down the meat around the forearm bone b1 such that the upper end part of the upper arm bone b2 of the bone-in meat is exposed.

According to the above configuration, since the upper end part of the upper arm bone b2 is exposed by the pressing device 300, the lift plates 138a and 138b can reliably grip the upper end part of the upper arm bone b2.

Furthermore, the deboning system of the bone-in meat of the embodiment described above includes the fourth clamp rotation device 19 which is disposed along the endless track 11 and rotates the clamp 10, the fourth clamp rotation device 19 is positioned on the upstream side of the olecranon incision making device 400 in the direction of movement of the clamp 10 and disposes the olecranon of the bone-in meat on the rear side in the direction of movement of the clamp 10, and the pair of the olecranon cutters approach and come in contact with the meat around the olecranon from the rear side in the direction of movement of the clamp 10.

According to the above configuration, it is possible to reliably cut the meat around the olecranon of the bone-in meat suspended from the clamp 10 without preventing the movement of the clamp 10 along the endless track 11.

Moreover, the deboning system of the bone-in meat of the embodiment described above includes the left/right determination station (left/right determination device) ST2 for determining the left or the right of the bone-in meat, and the fourth clamp rotation device 19 operates according to the result of the determination of the left/right determination station ST4.

According to the above configuration, even when the left and the right of the bone-in meat are confused and the bone-in meat is suspended from the clamp 10, the olecranon of the bone-in meat is disposed on the rear side in the direction of movement of the clamp 10 by the left/right determination station ST4 and the fourth clamp rotation device 19. Accordingly, it is possible to perform deboning of the right bone-in meat and the left bone-in meat with excellent yields.

Figure 79:
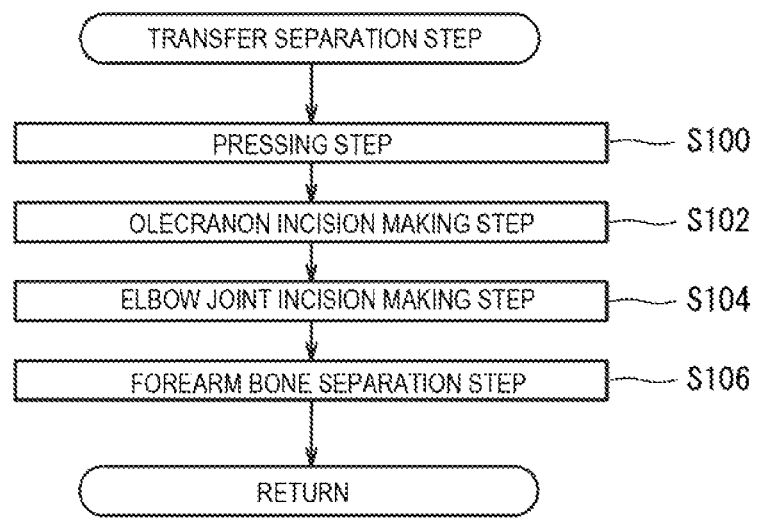
FIG. 79 is a flowchart schematically showing operation procedures in a transfer separation step.

Herein, FIG. 79 is a flowchart schematically showing procedures of the transfer separation step S40 performed in the transfer separation station ST10. According to the embodiment of the present invention described above, referring to FIGS. 2 and 78, there is provided the deboning method of the bone-in meat including the suspension step S14 of gripping the tip end part of the forearm bone b1 of the bone-in meat and suspending the bone-in meat using the clamp 10 which is movable along the endless track 11, the forearm-bone incision making steps S16, S22, and S30 of cutting the meat around the forearm bone b1 of the bone-in meat suspended by the clamp 10 using the forearm-bone incision making device which is disposed along the endless track 11 and has the robot arm 40 and the cutter tool (forearm cutter) 132 attached to the robot arm 40, the olecranon incision making step S100 of cutting the meat around the olecranon of the bone-in meat suspended by the clamp 10 using the olecranon incision making device 400 which has the pair of the olecranon cutters disposed on both sides of the endless track 11, and the forearm-bone separation step S106 of separating the forearm bone b1 and the upper arm bone b2 from each other using the lift plates 138a and 138b which are disposed along the endless track 11 and are used for pulling the bone-in meat suspended by the clamp 10 such that the forearm bone b1 and the upper arm bone b2 of the bone-in meat are separated from each other.

According to the deboning method of the bone-in meat described above, the meat around the forearm bone b1 is cut using the cutter tool 132 of the forearm-bone incision making device, and the meat around the olecranon is cut using the pair of the olecranon cutters of the olecranon incision making device 400. Thus, by using the forearm-bone incision making device and the olecranon incision making device 400, it is possible to enhance the automation rate.

On the other hand, according to the deboning method of the bone-in meat described above, after the meat around the olecranon is cut using the pair of the olecranon cutters, it is possible to separate the forearm bone b1 and the upper arm bone b2 from each other. In this case, as compared with the case where the meat around the olecranon is cut using the cutter tool 132 attached to the robot arm 40, the meat adhering to the part around the olecranon fossa F of the upper arm bone b2 is reduced and yields are improved.

In addition, according to the deboning method of the bone-in meat of the embodiment described above, by having the pressing step S100 of pressing down the meat around the forearm bone using the pressing device 300, the lift plates 138a and 138b can reliably pinch the upper end part of the upper arm bone b2.

Further, according to the deboning method of the bone-in meat of the embodiment described above, by having the elbow joint incision making step S104 of cutting a tendon around the elbow joint using the round blade cutter devices 240a and 240b, it is possible to smoothly separate the forearm bone b1 and the upper arm bone b2 from each other in the forearm-bone separation step S106.

The invention claimed is:

1. An X-ray image capturing device of bone-in meat for capturing an X-ray image of the bone-in meat that is from an arm part or a thigh part of a livestock carcass in a state where the bone-in meat is suspended, comprising:
   a clamp configured to suspend the bone-in meat and go around an endless track;
   an X-ray source configured to irradiate the bone-in meat with an X-ray;
   a shielding box configured to cover the bone-in meat while the X-ray image is captured;
   a sensor which is disposed in the shielding box and which detects the X-ray which passes through the bone-in meat;
   a filter which is disposed between the bone-in meat and the X-ray source and which adjusts an intensity distribution of the X-ray with which the bone-in meat is irradiated; and
   a rotation mechanism configured to rotate the clamp so that the bone-in meat rotates about a vertical axis in a rotation direction corresponding to whether the bone-in meat is from a right side or a left side of the livestock carcass in order to capture the X-ray image.

2. The X-ray image capturing device of bone-in meat according to claim 1, wherein
   the rotation mechanism rotates the clamp such that an incident angle of the X-ray relative to a cut surface of the bone-in meat separated from a trunk is more than 30° and less than 45°.

3. The X-ray image capturing device of bone-in meat according to claim 1, further comprising:
   a shielding-box movement mechanism which moves the shielding box in a direction along the endless track and a direction orthogonal to the endless track in synchronization with the clamp.

4. A deboning system for bone-in meat, comprising:
   an X-ray image capturing device of bone-in meat configured to capture an X-ray image of the bone-in meat that is from an arm part or a thigh part of a livestock carcass in a state where the bone-in meat is suspended, the X-ray image capturing device comprising:
   an X-ray source configured to irradiate a bone-in meat with an X-ray;
   a shielding box configured to cover the bone-in meat while an X-ray image is captured;
   a sensor which is disposed in the shielding box and which detects the X-ray which passes through the bone-in meat; and
   a filter which is disposed between the bone-in meat and the X-ray source and which adjusts an intensity distribution of the X-ray with which the bone-in meat is irradiated,
   wherein the X-ray image capturing device further comprises an incision making device configured to make an incision in the bone-in meat based on the X-ray image captured by the X-ray image capturing device.

5. An X-ray image capturing method for capturing an X-ray image of the bone-in meat from an arm part or a thigh part of a livestock carcass in a state where the bone-in meat is suspended, the method comprising:
   irradiating the bone-in meat with an X-ray from an X-ray source;
   covering the bone-in meat with a shielding box in which a sensor for detecting the X-ray passing through the bone-in meat is disposed;
   disposing a filter between the bone-in meat and the X-ray source, the filter being configured to adjust an intensity distribution of the X-ray with which the bone-in meat is irradiated;
   suspending the bone-in meat from a clamp configured to go around an endless track; and
   rotating the clamp so that the bone-in meat rotates about a vertical axis in a rotation direction corresponding to whether the bone-in meat is from a right side or a left side of the livestock carcass in order to capture the X-ray image.

\* \* \* \* \*